United States Patent [19]

Logan et al.

[11] Patent Number: 4,873,632
[45] Date of Patent: Oct. 10, 1989

[54] APPARATUS AND METHODS FOR SCATTER REDUCTION IN RADIATION IMAGING

[75] Inventors: K. William Logan; William D. McFarland, both of Boone County, Mo.

[73] Assignee: The Curators of the University of Missouri, Columbia, Mo.

[21] Appl. No.: 57,967

[22] Filed: Jun. 1, 1987

Related U.S. Application Data

[63] Continuation-in-part of Ser. No. 604,989, Apr. 27, 1984, Pat. No. 4,755,680.

[51] Int. Cl.$^4$ .............................................. G01T 1/20
[52] U.S. Cl. ......................... 364/413.13; 364/413.19; 364/413.22; 364/413.24; 250/363.02
[58] Field of Search ................... 364/413.19, 527, 581, 364/413.13, 413.22, 413.24; 250/358 R, 369, 363 S

[56] References Cited

U.S. PATENT DOCUMENTS

| | | | |
|---|---|---|---|
| 3,936,638 | 2/1976 | Gibbons | 250/358 R |
| 4,071,762 | 1/1978 | Lange et al. | 250/369 |
| 4,095,108 | 6/1978 | Inbar et al. | 250/369 |
| 4,258,428 | 3/1981 | Woronowicz | 364/527 |
| 4,415,982 | 11/1983 | Nishikawa | 364/527 |
| 4,546,255 | 10/1985 | Knoll et al. | 250/369 |
| 4,575,810 | 3/1986 | Stoub | 364/581 |
| 4,755,680 | 7/1988 | Logan | 250/363 R |
| 4,769,757 | 9/1988 | Horiba et al. | 364/413.13 |

OTHER PUBLICATIONS

Beck et al., "Effects of Scattered Radiation on Scintillation Detector Response", Med. Radioisotope Scintigraphy, Int'l. Atomic Energy Agency, Vienna, 1969, vol. 1; face sheet, tbl. of cont., pp. 595–616.
Johnston et al., "Inherent Problems in the Quantitation of Isotope Scan Data", Med. Radioisotope Scintigraphy, Int'l. Atomic Energy Agency, Vienna, 1969, vol. 1; pp. 617–631.
Genna et al., "Four-View Computer Scintiscanning", Med. Radioisotope Scint., 1972, vol. 1, Int'l. Atomic Energy Agency, Vienna, 1973; face sheet, tbl. of cont., pp. 133–154.
Bloch et al., "Reduction of the Effects of Scattered Radiation on a Sodium Iodide Imaging System", J. Nucl. Med., 14(2), pp. 67–72, 1973.
Inia, "Reduction of the Effects of Scattered Radiation"

(List continued on next page.)

Primary Examiner—Jerry Smith
Assistant Examiner—Charles B. Meyer
Attorney, Agent, or Firm—Senninger, Powers, Leavitt and Roedel

[57] ABSTRACT

The apparatus reduces scatter in radiation imaging and may be used with a detector of ionizing radiation that is partly unscattered and partly Compton scattered. The detector produces an energy signal representing values of energy of the radiation and produces coordinate position information for the radiation. Data storage means for holding numerical values and means for displaying an image based on the numerical values in the data storage means are also used with the inventive apparatus. The scatter reduction apparatus includes circuitry responsive to the energy signal from the detector for producing first and second signals which indicate whether each value of energy represented by the energy signal at a given time is in a first energy range or in a second energy range less than half as wide as the first energy range and having at least some energies in common with the first energy range. Further included is circuitry responsive to the first and second signals and the coordinate position information for generating numerical values for each coordinate position and storing them in the data storage means, the numerical values being a function of the difference of the number of occurrences of radiation in the first energy range at each coordinate position less a second number proportional to the number of occurrences of radiation in the second energy range at that coordinate position. Other apparatus and methods are also described.

82 Claims, 21 Drawing Sheets

OTHER PUBLICATIONS with The Authors' Reply, *J. Nucl. Med.,* 15 (4), pp. 316-317, 1974.

Atkins et al., "Effects of Scatter Subtraction on Image Contrast", *J. Nucl. Med., 16(1), pp. 102-104, 1975.*

Hoffer et al., "Measurement of Scatter Fraction in Liver and Brain Scans Performed with a Gamma Camera", *J. Nucl. Med.,* 16(6), p. 535, 1975.

Muehllehner et al., "Performance Parameters of a Positron Imaging Camera", *IEEE Trans. Nucl. Sci.,* NS-23(1), pp. 528-537, 1976.

Genna et al., "Analysis of an Arcuate Gamma Camera Design for Transaxial Reconstruction", *Med. Radionuclide Imaging,* Int'l Atomic Energy Agency, Vienna, 1977; face sheet, pp. 323-339.

Richardson, "Anger Scintillation Camera", *Nucl. Med. Physics,* Edit. F. D. Rollo, 1977, Contents and pp. 231-270.

Pang et al., "The Effect of Compton Scattered Photons on Emission Computerized Transaxial Tomography", *IEEE Trans. Nucl. Sci., NS-26(2), 1979, pp. 2772-2774.*

Pang et al., "The Effect of Compton Scattering on Emission Transaxial Tomography", *J. Nucl. Med., 20(6), 1979, p. 608.*

Atkins et al., "Analysis of the Scatter Response Function of Collimated Imaging Systems", *J. Nucl. Med., 20(6), 1979, p. 608.*

Ricci et al., "Investigation of a Technique for Providing a Pseudo-Continuous Detector Ring for Positron Tomography", *IEEE Trans. Nucl. Sci.,* NS-29(1), 1982, pp. 452-456.

Axelsson et al., "Subtraction of Compton-Scattered Photons in Single-Photon Emission Computerized Tomography", *J. Nucl. Med.,* 25(4), 1984, pp. 490-494.

Jaszczak et al., "Improved SPECT Quantification Using Compensation for Scattered Photons", *J. Nucl. Med.,* 25(8), 1984, pp. 893-900.

Harris et al., "TC-99m Attenuation Coefficients in Water-Filled Phantoms Determined with Gamma Cameras", *Med. Physics,* 11(5), 1984, pp. 681-685.

Jaszczak et al., "Scatter Compensation Techniques for Spect", *IEEE Trans. Nucl. Sci.,* vol. 32, Feb. 1985, 8 pp.

Jaszczak et al., "Estimating SPECT Count Densities, Scatter Fractions, and Statistical Noise", *IEEE Trans. Nucl. Sci.,* vol. 32, Feb. 1985, 7 pp.

Zeeberg et al., "An Efficient Algorithm for Reconstruction of SPECT Images in the Presence of Spatially Varying Attenuation", *IEEE Trans. Nucl. Sci.,* 32(2), Apr. 1985, 8 pp.

"Proceedings of the 33rd Annual Meeting", *J. Nucl. Med.,* 27(6), 1986, pp. 883-885, 898, 899 and 960.

Siegel et al., "Weighted Acquisition: A Method for Improving Bone and Gallium Images", for SNM Meeting, 6/86, 1 page.

DeVito et al., "Weighted Acquisition Using Finite Spatial Filters for Real-Time Scatter Removal", for SNM Meeting, 6/86, 1 page.

"Siemens Presents W.A.M. for Digitrac", undated, title page, pp. 1-15, 3 unnumbered pages (in Weighted Acquistion Module letter).

Haerten, "ECT Processor Software—Now with Volume Smooth, Attenuation Correction and Scatter Correction", Siemens Gammasonics, Inc., MB #205, 7 pp.

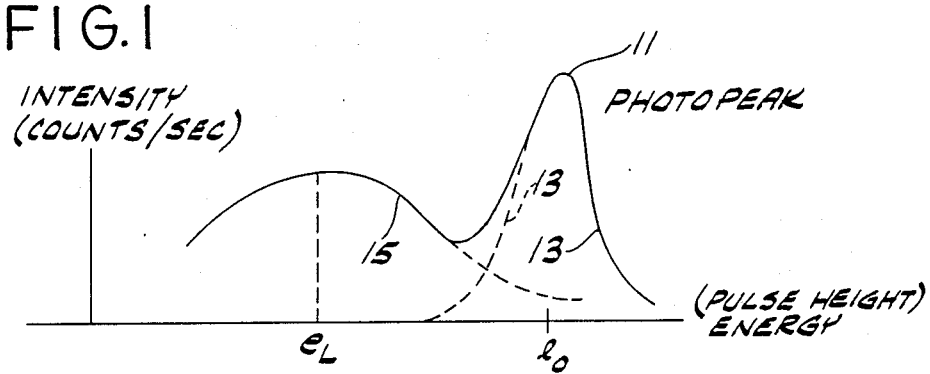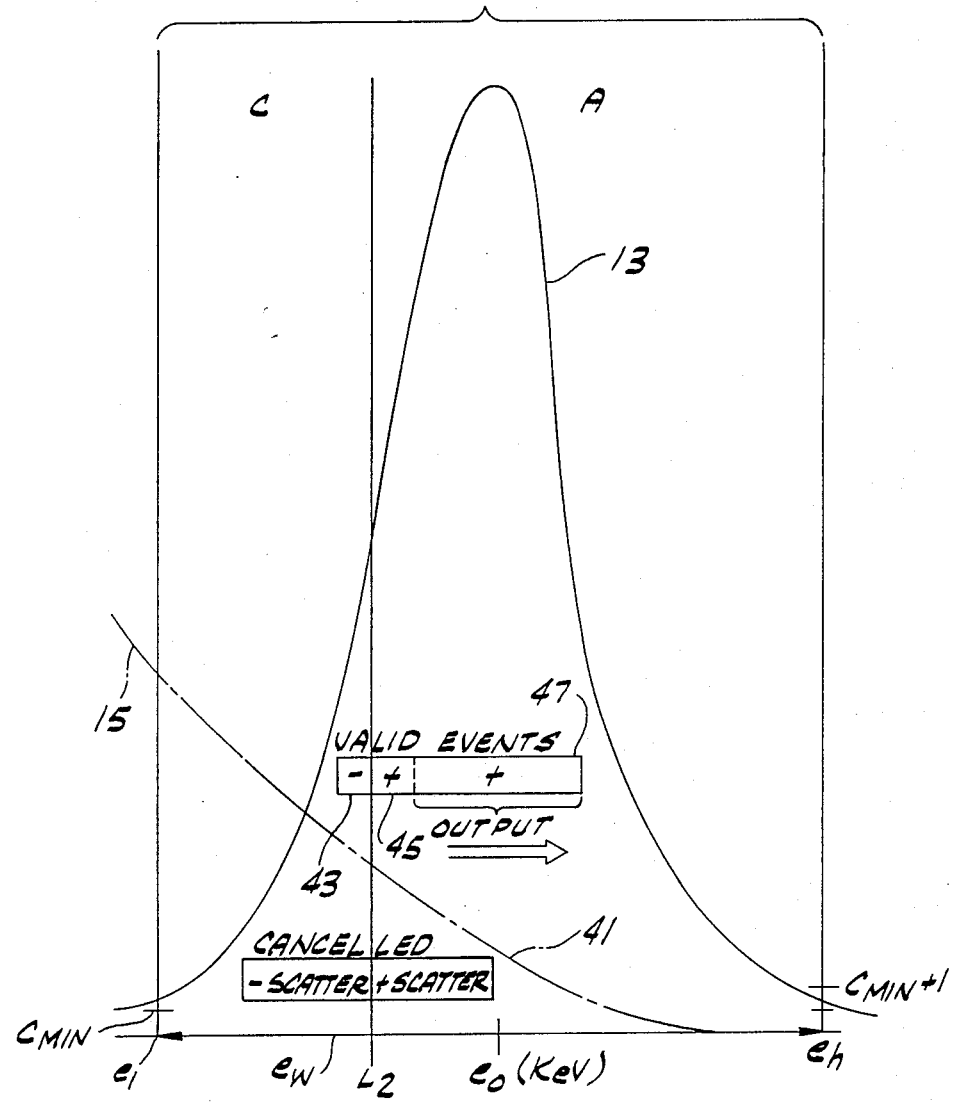

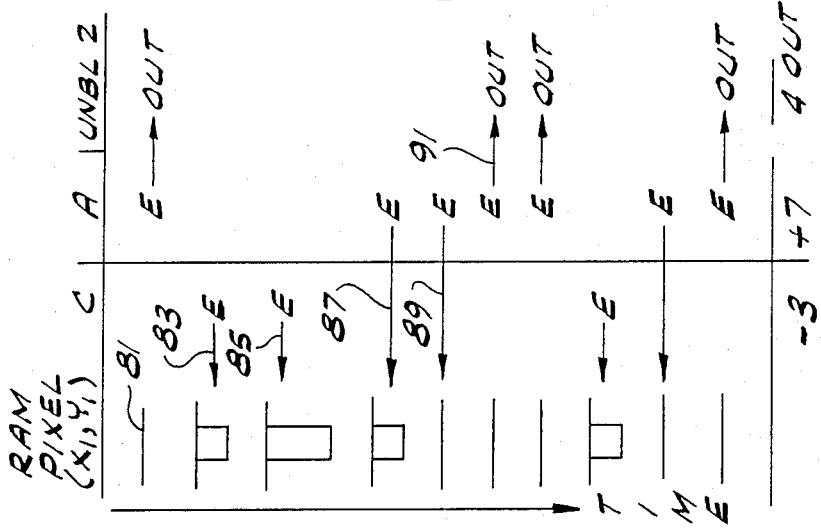

APPARATUS AND METHODS FOR SCATTER REDUCTION IN RADIATION IMAGING

CROSS REFERENCE TO RELATED APPLICATION

The present application is a continuation-in-part of coassigned application Ser. No. 604,989 "Radiation Imaging Apparatus and Methods" filed Apr. 27, 1984, now U.S. Pat. No. 4,755,680. The U.S. Pat. No. 4,755,680 is hereby incorporated herein by reference.

NOTICE

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

BACKGROUND OF THE INVENTION

The present invention relates to apparatus and methods of reducing scatter such as Compton scatter in radiation imaging systems such as gamma cameras and positron annihilation cameras. More particularly, the present invention relates to various apparatus and methods some of which reduce Compton scatter by subdividing the photopeak window into lower and upper portions and subtracting the lower portion from the upper portion for each of many regions of an image.

Radiation imaging apparatus such as scintillation cameras are well known devices used in nuclear medicine. A radiopharmaceutical (e.g. technetium 99m (Tc-99m), thallium 201 (Th-201), gallium 67 (Ga-67) or indium 111 (In-111)) is administered to the patient and temporarily accumulates in areas of the body where it is desired to image lesions. The radioactive isotope emits gamma rays (or positrons which decay into oppositely directed pairs of gamma rays) which then impinge on a scintillation detector such as sodium iodide adjacent to which is located one or more photomultiplier tubes or other means of converting scintillations to electrical pulses. Electronic apparatus is used to process the pulses and to determine coordinate position values of the source of each gamma ray which are used in forming an image.

The radioisotope source in other applications is located outside the patient and produces a fan beam or a cone beam that passes through the patient or specimen and impinges on an extended detector as in bone mineral densitometry for osteoporosis.

The prior art has recognized that gamma rays produced by radioactive decay may travel directly to the detector or may be scattered by mechanisms such as Compton scattering. When a gamma ray initially emitted in a particular direction is scattered, a gamma ray of somewhat different energy travels in another direction which then reaches the detector as information which interferes with or can be confused with gamma rays reaching the detector directly. Therefore, if the camera is designed to determine that the source of a particular gamma ray lies along a line coinciding with its direction of incidence on the detector, then Compton scatter photons will be misinterpreted as indicating a source distribution of the radionuclide in the patient which is actually different than its actual distribution. In practice the effect of Compton scattering is to provide fuzzy and indistinct images instead of desirable distinct images of the radionuclide distribution in the patient. For example, sodium iodide as a camera detector has a relatively poor energy resolution, and images obtained with conventional techniques employing a pulse height analyzer (PHA) window centered around the photopeak portion of the radiotracer spectrum will contain high (20-50%) fractions of scattered photon events.

As a result, devices designed to image the photon emissions from these radioactive materials are presented with a geometrically widespread mixture of scattered photons and non-scattered photons. There is no geometric method to separate scattered non-scattered photons since the usual source of radioactivity is distributed over a significant volume within the patient, and the emission of photons from radioactive decay is isotropic. The inclusion of scatter photons in the measurements obtained with imaging devices not only degrades the image contrast, but also the degradation is amplified by image reconstruction in emission computed tomographic imaging.

The physics of Compton scattering is well known and the energy of a scattered photon is given by the equation $$e_s = \frac{e_o}{1 + (1 - \cos A)e_o/mc^2} \quad (1)$$

where $e_s$ is the energy of the Compton scattered photon $e_o$ is the energy of the original emitted gamma ray, $mc^2$ is the equivalent energy of a particle such as an electron which scatters the original gamma ray ($mc^2$ for an electron is 511 KeV), and A is the Compton angle or angle between the direction of incidence of the original photon and the direction of travel of the scattered photon.

A scintillation camera typically has one or more pulse height analyzers (PHAs) by means of which the energy of radiation can be readily determined. Gating circuits detect incident photons upon the detector which have radiation energies within a predetermined band or "window" and all of the other radiation not within the window is excluded for imaging purposes. By inspection of the Compton scattering formula (1) it is apparent that a window which is set for a particular energy also determines the Compton angle of any scattered radiation that may enter. For example, a given radionuclide produces gamma rays having a particular energy $e_o$. Due to statistical factors the actual energy which is sensed at the detector will lie in a more or less peaked distribution centered on an energy called the photopeak energy and the distribution is conventionally called the photopeak. In a typical gamma camera a photopeak window or energy window is centered so as to have lower and upper energy boundaries bracketing the center of the photopeak $e_o$.

Unavoidably some Compton scattering produces radiation that is within the photopeak window which therefore is confused by the radiation imaging apparatus with gamma rays which have come directly from the radionuclide distribution in the patient. The boundaries of the photopeak window define the maximum angle of Compton scattering which can occur and still lie within the photopeak window and thus be confused with the true source distribution. The Compton angle is determined by solving the Compton formula (1) for Compton angle A after substituting the photopeak energy $e_0$ and the lower boundary of the photopeak window for $e_s$.

In one prior art approach a second entirely separate PHA window or energy range distinctly below the photopeak window is provided at lower energies where the Compton scattering is more numerous to acquire a scatter image. An empirically determined proportion of Compton events is subtracted from the number of detected incident gamma rays in the photopeak window as a rough means of estimating the actual Compton scattering in the photopeak and thus reducing its blurring effect on the image. In emission computed tomography (ECT), the scatter image may be used to construct a scatter ECT image which is subtracted from the regular ECT image at the same geometric position.

Unfortunately, the amount of Compton scattered radiation in a lower energy window in general bears little relationship to the actual amount of Compton scatter in the photopeak region itself. Compton scattering occurs due to radiation that originates in regions of the specimen adjacent to the region which is desired to be imaged and the distribution of the radionuclide in any given specimen is precisely the unknown which is to be imaged. As put by one worker "the contribution of adjacent regions over a particular site to the measured activity is almost entirely in the scatter region when collimated detector systems are used. Thus, the peak-to-scatter ratio would be diminished by the presence of appreciable amounts of radioactivity in adjacent structures. This localization must be determined in the course of mapping the peak-to-scatter ratio in and around the region(s) of interest, and the scatter contribution from the adjacent region(s) taken into account ... [I]t appears that a more comprehensive formalism is needed, since an almost infinite number of phantom configurations and calibrational studies would be needed ...

The suggestion that the scatter window be used as an index of the scatter contribution contained in the photopeak region seems destined to failure because of the phenomena described above. If all the scatter could be related to the activity distribution along the axis of the collimator, the procedure ... might be useful. Since, however, a variable but large fraction of scatter counts arise from surrounding regions, a single correction factor would not be very useful." R. E. Johnston et al., "Inherent Problems in the Quantitation of Isotope Scan Data" *Medical Radioisotope Scintigraphy*, Vol. I, IAEA, Vienna, 1969, pp. 617-631, at pp. 630-631.

A Compton scattering energy window approach is also discussed in "Four-View Computer Scintiscanning: Image Structuring Through Multi-Window Pulse-Height Analysis" by S. Genna et al. in *Medical Radioisotope Scintigraphy* 1972, IAEA, Vienna 1973, pps. 133-154 and R. J. Jaszczak "Scatter Compensation Techniques for SPECT", IEEE Trans. Nuclear Science, Vol. 32, February 1985.

In another approach to reducing Compton scatter a gamma camera has scintillation events displayed at X,Y coordinates on a cathode ray tube by unblanking the tube with z pulses applied to its control electrode. A Compton scattered radiation deemphasizer determines where the peaks of total energy pulses fall in a part of the energy spectrum or window which is the photopeak window for present purposes. The deemphasizer causes small Z pulses to be produced in the part of the spectrum where Compton scatter is most prevalant and causes increasingly larger Z pulses as the total energy increases up to the midpoint of the photopeak window where Compton scatter is less significant. Constant amplitude Z pulses are produced at and after the midpoint of the photopeak window. In FIG. 3 of this patent a distribution of energy at the photopeak window and the method of deemphasis is shown. A microprocessor implementation for accomplishing the deemphasis is shown in FIG. 6 of U.S. Pat. No. 4,258,428 to E. M. Woronowicz.

In U.S. Pat. No. 4,575,810 a "simplistic" and "completely synthetic" example (col. 4 lines 29-47) features three windows. The patent asks the reader to suppose that events in an upper section of the photopeak were known to provide twice as much image information as those in the lower section, and events in a region just below the photopeak could be subtracted to remove scatter. An upper window image would be added twice and the lower window image added once, while subtracting the below range window image. However, the patent states that it is likely that signal-to-noise ratios in the weighted image would not be larger than normal images, due to the simplistic nature of the example, and instead teaches an approach using a carefully constructed weighting function.

In U.S. Pat. No. 4,415,982 to M. Nishikawa a background suppression approach to improving the images is produced and no suggestion that scatter reduction is specifically intended is present. In the Nishikawa patent a scintillation camera has a memory with addresses corresponding to the elements of a matrix-like divided image of a scintigram and these addresses correspond to incident position signals of points of radiation determined by a position calculating circuit. A pulse height analyzer receives the radiation events registered by the camera head and issues an unblanking signal to control apparatus if the count rate is significantly higher than background noise. The content at the designated address in memory is compared with a predetermined minimum value of radiation in a comparator. When the content is less than the minimum value the control apparatus adds one to the content and restores the increased content to the designated address. When the content is at least equal to the minimum value, the control apparatus issues the unblanking signal to display apparatus to display the radiation at the designated address. In effect this apparatus accomplishes a kind of subtraction so that only those image positions which receive a number of events in excess of a predetermined number are displayed at all on the display apparatus.

The various approaches of the prior art evidently provide some reduction of the Compton scatter blurring of images and increase the contrast and distinctness of the images somewhat. However, the subtraction approach using a separate Compton window has been criticized in the cited literature because such approach is dependent on particular source distributions and is dismissed in the cited U.S. Pat. No. 4,575,810 as having low signal-to-noise ratio. A deemphasizer as described in U.S. Pat. No. 4,258,428 allows some Compton scatter to be detected because it passes all z pulses below the midpoint of the photopeak window except that these are deemphasized. The scintillation camera of Nishikawa in U.S. Pat. No. 4,415,982 does not purport to reduce Compton scattering. Compton scatter which is included in regions of the image which exceed the predetermined minimum of radiation which is blanked out by Nishikawa will not be reduced at all.

SUMMARY OF THE INVENTION

Among the objects of the present invention are to provide improved apparatus and methods to substantially reduce the blurring and distorting contribution of Compton scatter or other scatter to images produced by radiation imaging apparatus such as is used in nuclear medicine or other fields; to provide improved apparatus and methods to produce on-line real-time active removal of the scatter in nuclear medicine imaging signals and in other uses of radioactive tracers or radionuclides; to provide improved apparatus and methods which can be incorporated either in original equipment or can be retrofitted to radiation imaging apparatus presently in the field; to provide improved apparatus and methods which reduce Compton scatter and increase contrast in parts of the image in which the source intensity varies and already exceeds a predetermined minimum of radiation; to provide improved apparatus and methods which directly eliminate the scatter fraction normally included in images obtained with conventional pulse height analyzer (PHA) windows as normally utilized on Anger type gamma cameras, and other ionizing photon imaging systems; to provide improved apparatus and methods which receive total image signals (scatter plus non-scatter photons within PHA windows) from the imaging system electronics, remove the scatter portion and output substantially scatter-free image signals to typical image display and recording devices; to provide improved apparatus and methods for calibrating scatter reduction apparatus; to provide improved computerized processes for more effective scatter reduction in radiation imaging apparatus and methods; to provide improved scatter reduction apparatus and methods which can be used with radionuclides that have either a single photopeak or multiple photopeaks; to provide improved scatter reduction apparatus and methods which are calibrated conveniently, accurately and speedily; to provide improved scatter reduction apparatus and methods which will automatically adapt themselves to one or more energy windows established in radiation imaging apparatus such as a gamma camera with which the scatter reduction apparatus and methods are to be used; and to provide improved scatter reduction apparatus and methods which are more convenient, versatile, reliable, effective and economical.

Generally, one form of the invention is an apparatus for scatter reduction in radiation imaging for use with a detector of ionizing radiation that is partly unscattered and partly Compton scattered. The detector produces an energy signal representing values of energy of the radiation and produces coordinate position information for the radiation. Data storage means for holding numerical values and means for displaying an image based on the numerical values in the data storage means are also used with the inventive apparatus. The scatter reduction apparatus includes circuitry responsive to the energy signal from the detector for producing first and second signals which indicate whether each value of energy represented by the energy signal at a given time is in a first energy range or in a second energy range less than half as wide as the first energy range and having at least some energies in common with the first energy range. Further included is circuitry responsive to the first and second signals and the coordinate position information for generating numerical values for each coordinate position and storing them in the data storage means, the numerical values being a function of the difference of the number of occurrences of radiation in the first energy range at each coordinate position less a second number proportional to the number of occurrences of radiation in the second energy range at that coordinate position.

Generally, another form of the invention is an apparatus for scatter reduction in radiation imaging of ionizing radiation that has a photopeak in a first energy range and for use with data storage means for holding numerical values and means for displaying an image based on the numerical values in the data storage means. The apparatus includes means for detecting ionizing radiation that is partly unscattered and partly Compton scattered to produce an energy signal representing values of energy of the radiation in the first energy range and to produce coordinate position information for the radiation. The scatter reduction apparatus further includes circuitry responsive to the energy signal and the coordinate position information for generating numerical values for each coordinate position and storing them in the data storage means, the numerical values being a function of the difference of the number of occurrences of radiation in the first energy range at each coordinate position less a second number proportional to and at least two times the number of occurrences of radiation at that coordinate position in a second energy range.

In general, still another form of the invention is an apparatus for scatter reduction in radiation imaging for use with a detector of ionizing radiation that is partly unscattered and partly Compton scattered. The detector produces an energy signal representing values of energy of the radiation and produces coordinate position information for the radiation. The apparatus is further for use with data storage means for holding numerical values corresponding to each coordinate position, a circuit for incrementing each corresponding numerical value in response to an unblank signal and the coordinate position information, and means for then displaying an image based on the numerical values in the data storage means. The inventive scatter reduction apparatus includes memory means for storing tabular values corresponding to each coordinate position combined with means for incrementing or decrementing the tabular value for a particular coordinate position depending on whether the energy signal produced by an occurrence of the radiation at that coordinate position satisfies a first or a second predetermined energy condition respectively, and if the tabular value at that coordinate position has reached a preset value then instead producing an unblank signal to actuate the incrementing circuit, whereby that circuit increments the numerical value for that coordinate position in producing numerical values over a period of time for display purposes.

Generally, a further form of the invention is an apparatus for scatter reduction in radiation imaging for use with a detector of ionizing radiation that is partly unscattered and partly Compton scattered, the detector producing an energy signal representing values of energy of the radiation in a first energy range around a photopeak for the radiation and producing coordinate position information for the radiation. The apparatus includes memory means for holding a spectrum of intensity values representing a scatter spectrum combined with means for supplying an electrical reference level representing a predetermined energy in the first energy range of the radiation by premeasuring the scatter spectrum in the first energy range and predetermining the energy at which the total scatter in the first energy range below said energy is substantially equal to a predetermined fraction of the scatter in the first energy range, and means for producing a signal indicating when the energy signal is below or above the electrical reference level.

Generally, still another form of the invention is an apparatus for scatter reduction in radiation imaging for use with a detector of ionizing radiation that is partly unscattered and partly Compton scattered, the detector producing an energy signal representing values of energy of the radiation in a first energy range around a photopeak for the radiation and producing coordinate position information for the radiation. The apparatus includes memory means for holding a spectrum of intensity values representing a scatter spectrum, and means for premeasuring the scatter spectrum in the first energy range and producing an electrical signal representing a characteristic number from the scatter spectrum as a function of the ratio of the scatter in the first energy range to the total of the scatter in a predetermined lower energy fraction of the first energy range.

Other apparatus and method forms of the invention for achieving the above-stated and other objects of the invention are also disclosed and claimed herein.

Other objects and features will be in part apparent and in part pointed out hereinafter.

BRIEF DESCRIPTION OF THE DRAWINGS

FIG. 1 is a graph of a typical energy spectrum of a radionuclide which graph shows radiation intensity in counts per unit time on the ordinate versus energy (or camera energy pulse height) on the abscissa;

FIG. 3 is a detail of FIG. 1 showing a bell-shaped photopeak spectrum and a sloping Compton scatter spectrum, with division of a first energy range S into upper part A and lower part C for purposes of some embodiments of the inventive apparatus and methods;

FIG. 5 is a pictorial diagram of a memory of the Compton Scatter Filter of FIG. 4, the memory holding tabular values according to a method of the invention;

FIG. 6 is a chart showing a hypothetical series of operations on one memory cell of the memory of FIG. 5 corresponding to one pixel $X_1$, $Y_1$ where events E occur in either the C or A window of FIG. 3 and produce outputs OUT according to a method of the invention;

FIG. 7 is a number line further illustrating a method of the invention of FIG. 6;

FIG. 8 is a number line further illustrating an alternative method of the invention for computing tabular values in opposite sense to that shown in FIGS. 6 and 7;

FIGS. 10, 11 and 12 together are a schematic diagram of an embodiment of the inventive Compton Scatter Filter of each of FIGS. 4 and 9, wherein FIG. 10 is a schematic diagram of an inventive calibrating computer circuit operating according to methods of the invention;

FIG. 11 is a schematic diagram of further inventive circuitry including the memory of FIG. 5 for reducing scatter according to methods of the invention;

FIG. 12 is a schematic diagram of further circuitry of the invention for controlling the circuitry of FIG. 11 according to methods of the invention;

Corresponding reference characters indicate corresponding parts throughout the several views of the drawings.

DETAILED DESCRIPTION OF PREFERRED EMBODIMENTS

In FIG. 1 a photopeak 11 of radionuclide Tc-99m is centered around a center energy $e_o$. The observed spectrum is actually the sum of a bell-shaped spectrum 13 of light photon events corresponding to true photopeak photons (gamma rays) and a relatively broad spectrum 15 of Compton events resulting from Compton scattering of photopeak photons in the specimen to be imaged.

It is to be understood that gamma rays can be scattered at no more than 180°, which according to Compton scattering formula (1) is an energy of:

$$e_L = \frac{e_o}{1 + 2e_o/mc^2} \quad (2)$$

A typical scintillation material such as sodium iodide (NaI) produces scintillations of light which have an energy that is probabilistically related, according to an approximately bell-shaped curve, to the energy of any incident gamma ray, whether it be a true photopeak photon or a Compton scatter photon. As a result, Compton scatter photons are sometimes detected in the vicinity of the photopeak even when they have an energy outside a first energy range (e.g. with a range width of 25% or less of the center energy $e_o$). Therefore, a gamma camera having energy selection circuitry set to reject all photon events outside the first energy range does ordinarily pass Compton scatter. Such Compton scatter is both low angle scatter which produces a gamma ray with energy inside the first energy range itself, and higher angle scatter which produces a gamma ray outside the first energy range but which has some probability of being detected in the first energy range anyway, as just mentioned.

Figure 2:
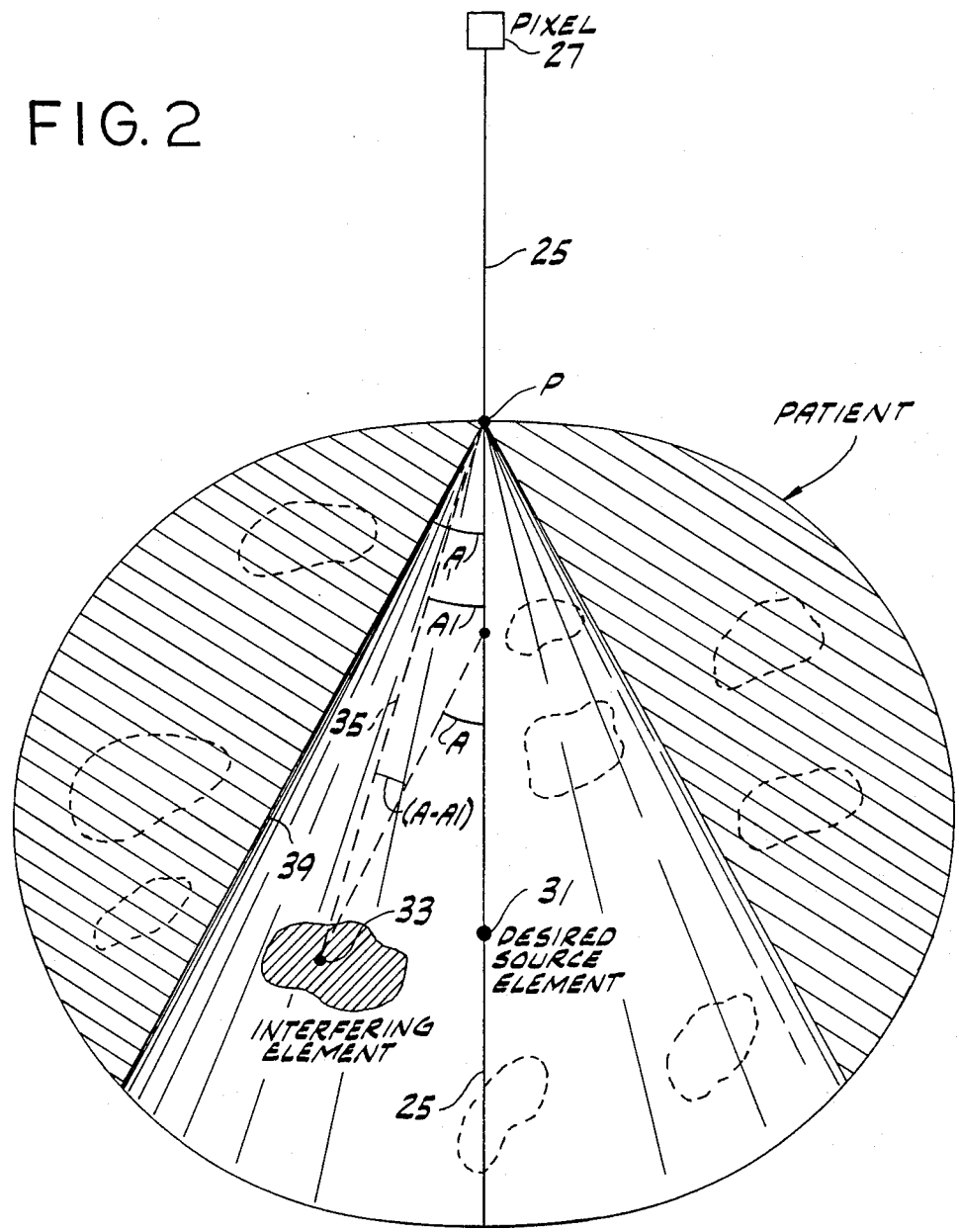
FIG. 2 is a pictorial diagram of a radioactive source element and a radioactive interfering element in the head of a patient with a cone drawn to show where most Compton scatter interference in a given image pixel would originate.

In FIG. 2, a head of a patient has a complex unknown source distribution of a radionuclide which has recently been administered. A camera such as in FIG. 1 of U.S. Pat. No. 4,755,680 produces an image comprising numerous pixels, only one pixel 27 being shown in FIG. 2 herein. For illustration a line 25 passes through pixel 27 in a direction of collimation of the camera. A source element 31 which it is desired to image emits radiation along the line 25. Unfortunately, an element 33 lying away from the line 25 emits radiation toward parts of the head lying on line 25 and produces Compton scattered photons which travel along line 25 into the camera and contribute interference to the pixel 27.

As shown in FIG. 3, a gamma camera utilizes a photopeak energy window S which is of limited width $e_w$ (12-25% of center energy $e_o$). Most of the interfering sources of Compton scattering are limited to a cone in FIG. 2 which has line 25 as its axis and its apex located where line 25 intersects the surface of the specimen. The cone has an apex angle A which is the angle determined from equation (1) at which Compton scattering produces gamma photons of energy $e_1$ equal to the low energy boundary of window S.

It is to be understood that Compton scattering can occur at any angle, and that the energy of the Compton scattered radiation may be regarded as broadened according to a Gaussian distribution a tail of which lies within the photopeak window. Therefore, some amount of Compton scattering that emanates from the specimen along the line 25 and reaches pixel 27 originates outside the cone. For qualitative purposes, the illustration shows a distinct cone, while it is to be understood that in actuality a fuzziness in the cone boundary allows some contribution to scatter from outside the cone.

In FIG. 2, the contribution of source distribution interfering areas or elements is maximum when the interfering areas are located at an angle A1 equal to about half the cone apex angle A. Angle A1 is defined as the angle of line 25 relative to a line segment 35 joining interfering element 33 with a point P where line 25 intersects the surface of the head or other specimen. This maximum contribution at half of angle A is due to two factors: first, that element 33 can scatter anywhere along line 25 through an angle A-A1, and second that the volume that interfering elements can occupy increases approximately with the square of the angle A1. Scatter image degradation does occur due to interfering regions of the radionuclide source distribution in the patient at very low angles of A1 (near line 25). However, this low angle scatter degradation is small notwithstanding that A-A1 is large because of the low volume at the low angles. The scatter image degradation due to interfering regions at high angles A1 (near cone surface 39) is also small, but because A-A1 is small. In contrast, interfering elements like element 33 can occur in a substantial volume and scatter into line 25 through a substantial angle A-A1 when angle A1 is about half of apex angle A.

The physical distribution in the specimen of numerous radiation sources such as element 33 theoretically has some effect on the shape of a tail 41 of the scatter spectrum 15 in FIG. 3. However, it is believed that the shape of tail 41 is substantially independent of source distribution for most practical purposes involving complex extended source distributions in specimens encountered in nuclear medicine and other applications. One reason is that the Compton scatter received at each pixel such as 27 is a volume integrated quantity to which elements such as 33 throughout the cone of FIG. 2 contribute. Accordingly, there is a volume averaging effect that tends to also keep the shape of the energy distribution 41 of Compton scatter interference in the photopeak window about the same regardless of pixel position.

Some of the inventive embodiments make advantageous use of the essentially source-independent property of the shape of the Compton scatter spectrum 41 (FIG. 3), as now discussed in further detail. One concept used in some of the embodiments uses a ratio R of total scatter "+SCATTER" above an energy L2 divided by total scatter "−SCATTER" below energy L2. Then for each pixel, R is multiplied by the number of events in window S below L2 whether they be scatter or not. The product is subtracted from the total of events in window S above L2. Because of the predictable shape of scatter spectrum 41, the scatter is advantageously cancelled in the process as indicated by "−" and "+" boxes 43 and 45. The remainder 47 represents true photopeak events, numerical values of which are output for each pixel to define a scatter-free image.

A theory of operation of some of the embodiments is next discussed. It is to be understood that the theory is presented to motivate some of the concepts and the utility of the embodiments to which it pertains and is not exhaustive or meant to necessarily pertain to all embodiments comprehended in the spirit and scope of the invention.

In a typical nuclear medicine imaging system the spectrum of pulse heights falling within a pulse height analyzer (PHA) window when the window encompasses a photopeak is composed of a mixture of scattered and nonscattered photons. The majority of scattered photons are from scattering events occurring in the specimen, and the non-scattered photons are those that have traveled from the site of emission with no interaction in the specimen, or in any collimator of the imaging apparatus. In a gamma camera, this mixed spectrum is present at all locations on the face of the detector crystal which receive any photons originating in the patient. At a typical location with rectangular coordinates X, Y (or angular and axial coordinates in a cylindrical camera of parent application Ser. No. 604,989), a mixture of photons cause electronic pulses to be sent to a PHA, or pulse height analyzer also known as a single channel analyzer 127 as in FIG. 6 of the parent application. The total number of photon events falling in a PHA window symmetrically positioned around the photopeak, is S for some time period T. Then number of events S can be represented in two parts:

$$S = a1S + b1S \quad (3)$$

where a1 is the fraction of events S that occur from scattered photons, and b1 is the fraction of events S which occurs from non-scattered photons. Constants a1 and b1 vary substantially over the pixels of an image of a complex source distribution. Note that:

$$a1 + b1 = 1 \quad (4)$$

Next consider a second PHA window A receiving a portion of the same spectrum of pulses as the entire photopeak window. Window A is narrower than the entire photopeak window, and positioned asymmetrically toward the high energy side of the photopeak as shown in FIG. 3. The number of events with pulses falling in window A is $$A = a2 a1 S + b2 b1 S \quad (5)$$

The first term a2a1S is the scattered photon pulses which fall within window A, and the second term b2b1S is the non-scattered photon pulses which fall in window A. The constant a2 is the fraction of scattered photons in the entire photopeak window that also occurs in window A. The constant a2 can be experimentally measured as discussed later hereinbelow. As discussed above regarding shape of spectrum 41, constant a2 is essentially independent of the total scatter fraction a1.

The second constant in equation (5), b2, is the fraction of non-scatter photons in the entire photopeak window that also appear in window A. Due to the predictable nature of bell-shaped photopeak spectrum 13, the value b2 can be measured by imaging a point source in air where no scatter occurs and the bell-shaped spectrum 13 can be isolated. Both a2 and b2 can be determined experimentally for any imaging system, and for a variety of selections of photopeak window S and window A. Since S, the number of counts at the typical location X, Y allowed by the photopeak window is a measured value, as is the number of counts A that correspond to window A (both S and A are measured during the same time interval T), Equations (3), (4), and (5) can be solved for the non-scattered events in the photopeak window by substituting $b1 = (1 - a1)$ from Equation (4) into Equation (5), solving for a1S and substituting for a1S in Equation (3) and solving for b1S with the result:

$$b1S = (A - a2S)/(b2 - a2) \quad (6)$$

Note that Equation (6) states the non-scattered photon portion of the events with pulses that fall in the photopeak window in terms of the experimentally measured constants a2 and b2, and the number of events S and A corresponding to the photopeak window and its included window A.

The previous discussion and the results for the non-scattered events described by Equation (6) are independent of the location on the camera crystal X,Y. Equations (3)–(6) can therefore be generalized to the entire image area and the variables A and S can represent two dimensional fields or matrices of pixels which are the same as digital images.

In summary, the above discussion indicates that by using two simultaneous subwindows A and C in the photopeak window S of FIG. 3 it is possible to filter out a separate image of the non-scatter photons that are originally mixed with scattered photons. Advantageously, the narrow C window substantially overlaps or is completely inside or totally encompassed by the entire photopeak window.

Several different inventive methods can be recognized for collecting the image data and calculating the non-scatter image as described by Equation (6). These methods are described below. Essentially, data is collected for images in the photopeak window or first energy range S and the lower subwindow C which is a second energy range included in S, where C is given by $$C = S - A \quad (7)$$

In words, equation (7) expresses the concept that the number of radiation counts in window C is equal to the number of counts in window S less the number of counts in window A.

The method for collecting an A image and a C image corresponds to collecting data for events that have pulse heights that fall anywhere in the upper, or higher energy, window part A, and data that correspond to pulse heights that fall in lower energy window part C. Using Equation (7) to eliminate S in the righthand side of Equation (6), the scatter-free image b1S is obtained as follows:

$$b1S = ((1 - a2)A - a2C)/(b2 - a2) \quad (8)$$

By factoring out the quantity $(1 - a2)$ and designating by R a characteristic ratio of scatter in A to scatter in C expressed by quantity $a2/(1 - a2)$, the following expression for scatter-free image b1S is obtained:

$$b1S = (1 - a2)(A - RC)/(b2 - a2) \quad (9)$$

Note that the factors $(1 - a2)/(b2 - a2)$ and R in Equation (9) are a function only of the imaging system and the windows A and C selected and can be determined in a separate calibration sequence prior to the normal imaging procedure. The factor that determines the scatter removal is $(A - RC)$.

Using Equation (7) to eliminate A in the right-hand side of Equation (6), the scatter-free image b1S is alternatively obtained as follows:

$$b1S = (1 - a2)(S - C(1 + R))/(b2 - a2) \quad (10)$$

Note that the factor that determines the scatter removal here is $(S-C(1+R))$.

By eliminating C, equation (10) is equivalently expressed as:

$$b1S=(1-a2)(A(1+R)-RS)/(b2-a2) \quad (11)$$

In Equation (11) the factor that determines the scatter removal is $(A(1+R)-RS)$.

The basic design of a scatter filter hardware embodiment described hereinbelow utilizes the signals generated by a typical gamma camera, or other ionizing radiation imaging apparatus. The particular hardware example advantageously performs in real-time the operation described in Equation (9) above as well as achieving other objects. In other words, the scatter is eliminated in a two-dimensional memory array that accumulates scatter-free information in electronics associated with the camera.

Figure 4:
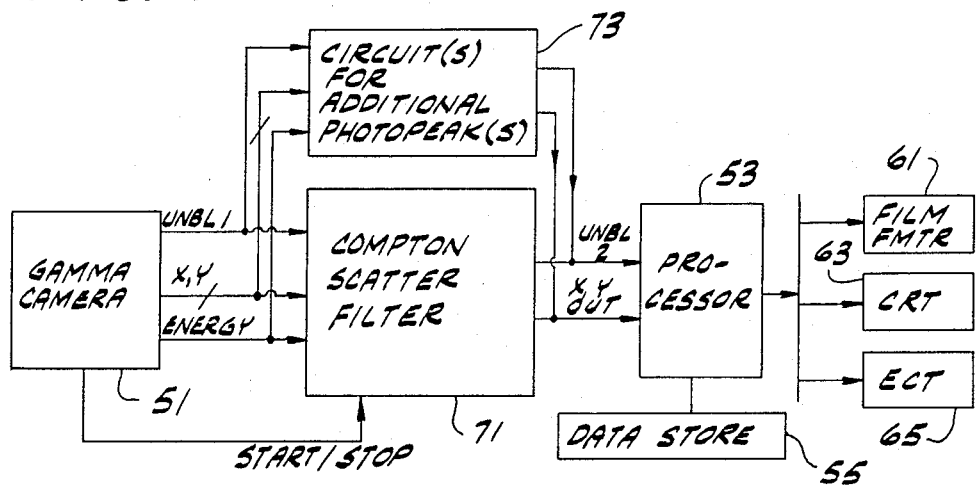
FIG. 4 is a block diagram of an improved radiation imaging system of the invention having a Compton Scatter Filter of the invention operating according to methods of the invention.

FIG. 4, for instance, shows an embodiment suitable for retrofit or with original equipment. In FIG. 4 the scatter is subtracted or filtered from the photopeak photon events as they are counted in real-time processing to obtain scatter-free data for each position or pixel in the image field of the imaging apparatus. A gamma camera 51 acts as a detector of ionizing radiation that is partly unscattered and partly Compton scattered. The detector produces an energy signal representing values of energy of the radiation and X,Y coordinate position information for the radiation. Gamma camera 51 in original equipment is used with a processor 53, a data store 55 for holding numerical values of accumulated radiation counts for each pixel of an image, and display equipment for displaying an image based on the numerical values in data store 55, including a film formatter 61, cathode ray tube (CRT) monitor 63 and ECT (emission computed tomography) computer and display. Processor 53 is suitably any commercially available nuclear medicine computer, for example.

By way of improvement in FIG. 4, an inventive Compton Scatter Filter 71 receives a Start/Stop signal from the gamma camera 51, as well as unblank pulses on a line UNBL1, analog signals indicative of X,Y coordinate positions of an occurrence of radiation, and an energy signal on an Energy line. Compton Scatter Filter 71 advantageously produces a lesser number of unblank pulses on an unblank line UNBL2, together with corresponding X,Y coordinate position information for processor 53 corresponding to the image of the specimen with the scatter events removed.

One or more circuits 73 identical to circuit 71 are added in parallel with circuit 71 and are tuned to one or more other photopeaks of the radionuclide in use, when it is desired to filter Compton scatter from the other photopeaks. Alternatively, simpler circuits are used to merely bypass circuit 71 when occurrences of energy pulses having a level indicative of other photopeaks occur. Circuit 73 may be dispensed with if the skilled worker elects not to filter scatter from other photopeaks.

In FIG. 4, the output signals of Compton Scatter Filter 71 are essentially the same shape and size as those produced by the gamma camera 51 so that compatible operation of processor 53 is achieved. The function of the Compton Scatter Filter 71 is thus to filter out at all positions in the image field of the gamma camera the fraction of events that are scatter radiation, and to pass through to the signal output connections the fraction of data corresponding to non-scattered events.

A scenario for processing a single event is as follows. When an ionizing event occurs in the camera crystal that causes an event signal of a height corresponding to an energy anywhere in the entire photopeak window, then camera output signals are generated. These signals are Energy, X position, Y position, Z or unblank, and are input to the Compton Scatter Filter 71 which determines whether the energy signal is in the A or C range for example. Event processing functions are then triggered. Since most cameras produce analog and not digital X and Y position signals, both the X and Y analog signals are fed to sample and hold circuits in Filter 71 followed by analog-to-digital converters (ADCs). The Z unblank pulse is used to enable the sample and hold circuits. For each event only one of two window signals A and C are active (high).

The X and Y ADCs determine a digital X and Y pair corresponding to a memory address or location in an image field memory 75 illustrated in FIG. 5. An electronic processor (implemented in hardware, firmware, or as a microprocessor programmed with appropriate software) in Filter 71 reads the X and Y digital values and the A and C logic levels.

FIG. 6 shows operations in Filter 71 depicted for a hypothetical series of events E which occur either in the A or C window. Only some of the events E cause an output OUT on line UNBL2, as indicated. The operations are discussed in more detail next.

All of the memory 75 locations corresponding to pixels are initialized to a preset value V0 such as zero, as indicated by reference line 81 of FIG. 6. If an event occurs with an energy in the A window of FIG. 3 in the particular pixel $(X_1, Y_1)$, then a Filter 71 output UNBL2 is generated because the preset value is already present in memory for this pixel.

Next in the FIG. 6 example, a C event 83 subsequently occurs at the same pixel, and the number stored in memory location X, Y is decreased by the value R in Equation (9). (The constant R is determined experimentally during prior calibration of the system.) For simplicity of illustration, it is assumed that amount R is unity in FIG. 6. No output signal is generated by the Compton Scatter filter 71 for C events. The X and Y ADCs, the X, Y and Z sample and hold circuits and the A and C event latches are reset and the system is ready to receive the next event from the gamma camera. Another C event 85 occurs at the same pixel, decreasing the number stored at the corresponding location by another amount R.

Next, an A event 87 occurs at the pixel, and the number stored in memory location X, Y is tested to determine if it has reached preset value V0, e.g. zero. If not, the stored number is increased by the value 1 (one) (see Equation (9)) since the value in memory is less than zero. In the example, another event 89 in window A in this pixel occurs until the value in memory for the pixel reached the preset value V0. Then on the next subsequent A event 91, an output unblank signal is generated by the scatter rejection filter apparatus and no addition occurs. The output signal representing scatter-free information is sent on to processor 53 for accumulation of a scatter free image. Again, the X and Y ADCs, the X, Y and Z sample and hold circuits and the A and C event latches are reset and the system is ready to receive the next event from the gamma camera.

Further operations in the example of FIG. 6 are also shown and should be apparent. In all, the example shows 7 A events and 3 C events. The Compton Scatter Filter in executing its operations correctly produces 4 UNBL2 unblank outputs representing the scatter free image intensity for that pixel.

It is to be understood that the operations of FIG. 6 are carried out for each pixel using the contents of memory locations of memory 75 of FIG. 5 as respective tabular values for keeping track of corresponding operations for every pixel in the image field. Further, as shown in FIG. 7, each pixel tabular value can be graphed on a number line with preset value V0 as starting point. When a C event occurs the tabular value is decreased by any amount proportional to constant R. When an A event occurs and V0 has not been reached, the tabular value should be increased, and the ratio which that amount of increase bears to unity should be the same as the ratio that the amount of decrease bears to R.

As shown in FIG. 8, the operations can be carried out in a reverse manner in which C events produce increases, and if the tabular value exceeds preset value V0, then a subsequent A event produces a decrease.

Figure 9:
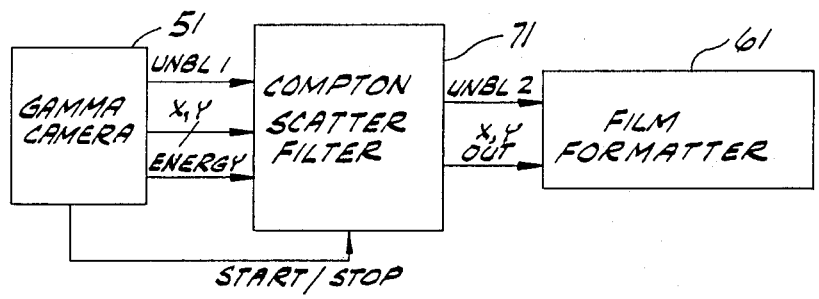
FIG. 9 is a block diagram of a Compton Scatter Filter of the invention combined with a gamma camera and a film formatter according to the invention.

FIG. 9 shows that when a display device such as film formatter 61 has a circuit that inherently accumulates or increments for counts of radiation in each pixel, then processor 51 of FIG. 4 can be omitted. As shown, gamma camera 51 is connected to Compton Scatter Filter 71, which in turn feeds the film formatter 61.

In some embodiments a gamma camera has at least two pulse height analyzers. If the two PHAs are set for windows S and A as shown in FIG. 3, then for pulses that fall within window A, many currently available cameras generate only a single output from the PHA circuitry, even though the pulse falls into both PHA windows. This is done to avoid double counting of single gamma ray events. The output from the PHA circuitry is usually a TTL (transistor-transistor-logic) or similar pulse used to increment a scaler, and to activate circuitry that produces X and Y position output signals. On the other hand, if a pulse is presented to the PHA circuitry which falls in window C, a different output pulse is generated by the PHA circuitry.

PHA outputs which correspond to events that fall in window A of FIG. 3 are designated A events, and events in window C are designated C events. Both A and C events trigger the X and Y position output signals even though they are separate and distinct as they emanate from the PHA circuitry, and can be separately monitored by devices outside of the camera.

Processing of output signals from gamma cameras and other ionizing radiation imaging systems as described above can be accomplished by a variety of different alternative embodiments. Real-time processing of each individual event as described above advantageously transfers image data, with scatter events removed, to any of the devices normally receiving camera output signals, and without appreciable delay.

Figure 10:
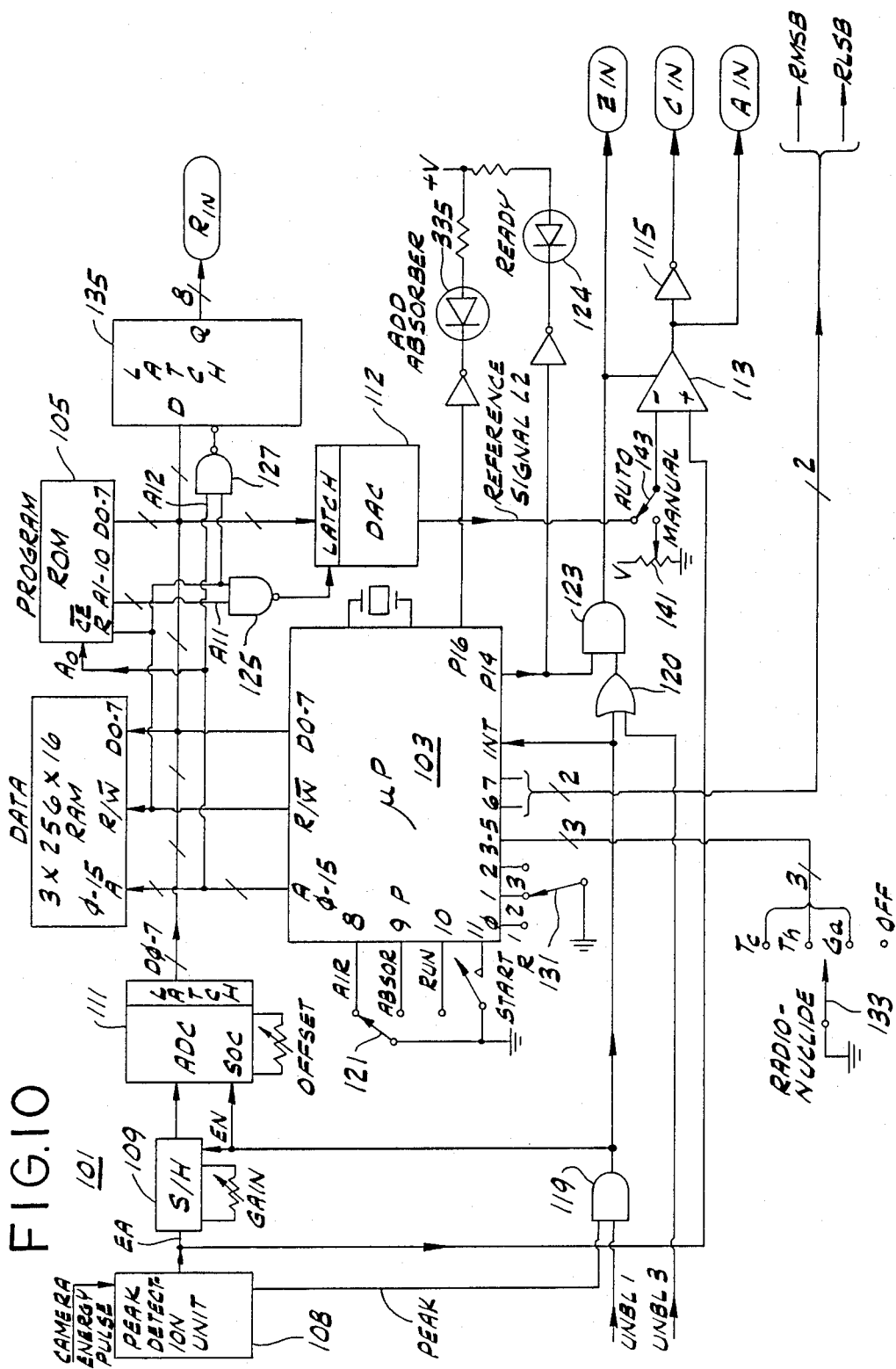

In FIG. 10, a Calibration Computer System 101 for use in Filter 71 has a microprocessor 103, associated ROM 105 for holding program software to operate it, a RAM 107 for holding energy spectra, a peak detection unit 108, sample-and-hold circuit S/H 109 and an analog-to-digital converter ADC 111 with output latch, and a digital-to-analog converter DAC 112 with an input latch. After a calibration procedure described later herein, a RUN mode is executed in which a comparator 113 compares the camera energy level, representing energy of an occurrence of the radiation, with an electrical reference signal determined by calibration to represent the energy L2 that separates the A and C windows in photopeak window S. When the camera pulse energy exceeds the energy L2, the comparator 113 output goes high, activating signal $A_{IN}$. An inverter 115 connected between the comparator 113 output and a line for $C_{IN}$ produces an output low at this time. When the camera pulse energy is less than the energy L2, the comparator 113 output goes low, deactivating signal $A_{IN}$ and activating signal $C_{IN}$ through inverter 115. In this way A events and C events are identified.

The signal representing camera pulse energy supplied to peak detector unit 108 should be the position corrected (Z axis correction) energy signal that is analyzed by the camera pulse height analyzer. Peak detection unit 108 receives and temporarily holds the voltage at the peak of the camera energy pulse. These functions are important because the peak voltage is the quantity that represents the energy of the radiation detected by the camera 51. Also, gating is performed in the circuit of FIG. 10 and unit 108 advantageously holds the energy pulse long enough to coincide with the slightly later-occurring unblank on a line UNLB1.

When an unblank pulse occurs line UNBL1 (corresponding to a photopeak from which scatter is to be removed) at the same time as a logic level output from unit 108, an AND gate 119 activates an interrupt pin INT at microprocessor 103 and enables S/H 109 and ADC 111 to digitize the energy information.

The camera unblank is usually a +5 volts by 1 microsecond square pulse (usually TTL) timed near the center of the X,Y position signal interval. In the RUN mode of a switch 121, microprocessor 103 is programmed to supply an output P14 to enable an AND-gate 123 to allow the unblank pulse to pass to line $Z_{IN}$. Output P14 also lights a LED 124 labeled "READY". In calibration, gate 123 is disabled. When an unblank pulse occurs on a line UNBL3 corresponding to a second higher energy photopeak which is passed without scatter removed, interrupt pin INT is not affected, thereby preventing the higher photopeak from affecting calibration. In RUN mode the energy pulse from the higher energy photopeak is fictitiously treated to contribute to the image as if it occurred in the A window of the lower photopeak, and since the higher energy photopeak always exceeds energy L2, there is never any C output produced in response to such higher photopeak occurrence. The unblank UNBL3 for the higher photopeak passes through an OR-gate 120 and AND gate 123 in RUN mode to activate output $Z_{IN}$.

A switch 131 is adjusted to a characteristic number R of 1, 2 or 3. In this way, the probable optimum value of R is preestablished by switch 131 when the FIG. 10 circuit is used with the circuits of FIGS. 11 and 12. A Radionuclide switch 133 is set to its OFF position when R is to be preset by switch 131 in this way. Switch 131 is an example of a means for selectively establishing this constant R. Microprocessor 103 provides a two-bit representation (RMSB, RLSB) of number R to a multiplexer 275 in FIG. 12 corresponding to the value of R selected on switch 131.

Microprocessor 103 also computes and provides a digital representation of energy L2 to define the appropriate C window corresponding to the preestablished R, which digital representation is converted to analog form and applied as the reference signal for comparator 113. Thus microprocessor 103 is an example of a means for varying the second energy range in width as a function of the constant selectively established and for supplying an electrical reference signal representing a predetermined energy (e.g., L2) in the first energy range and thereby defining the upper limit of the second energy range as a function of the proportionality constant. The reference level can also be manually adjusted by a potentiometer 141 selectable for comparator 113 by an AUTO-MANUAL switch 143.

As discussed hereinafter, R can conversely be computed for a preestablished window set by the Radionuclide switch 133, and output through a latch 135 to the circuitry of FIG. 29 in that embodiment. A pair of chip select AND-gates 125 and 127 respectively respond to signals on address lines A11 and A12 to enable DAC 112 or latch 135 on occurrence of a Write signal on a line R/W/under control of microprocessor 103. When Radionuclide switch 133 is not OFF, the value on R switch 131 is ignored by microprocessor 103.

Figure 11:
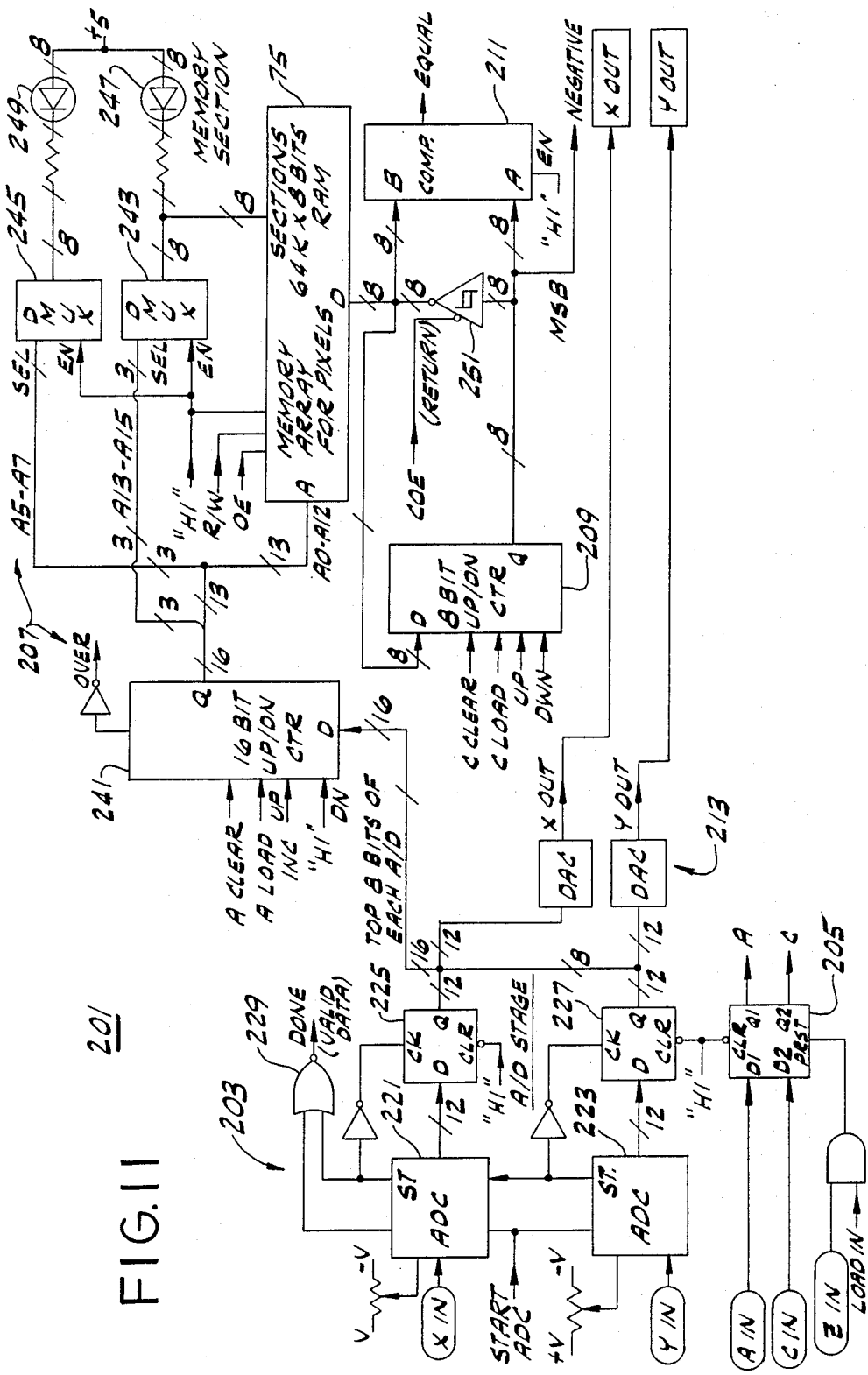
Figure 12:
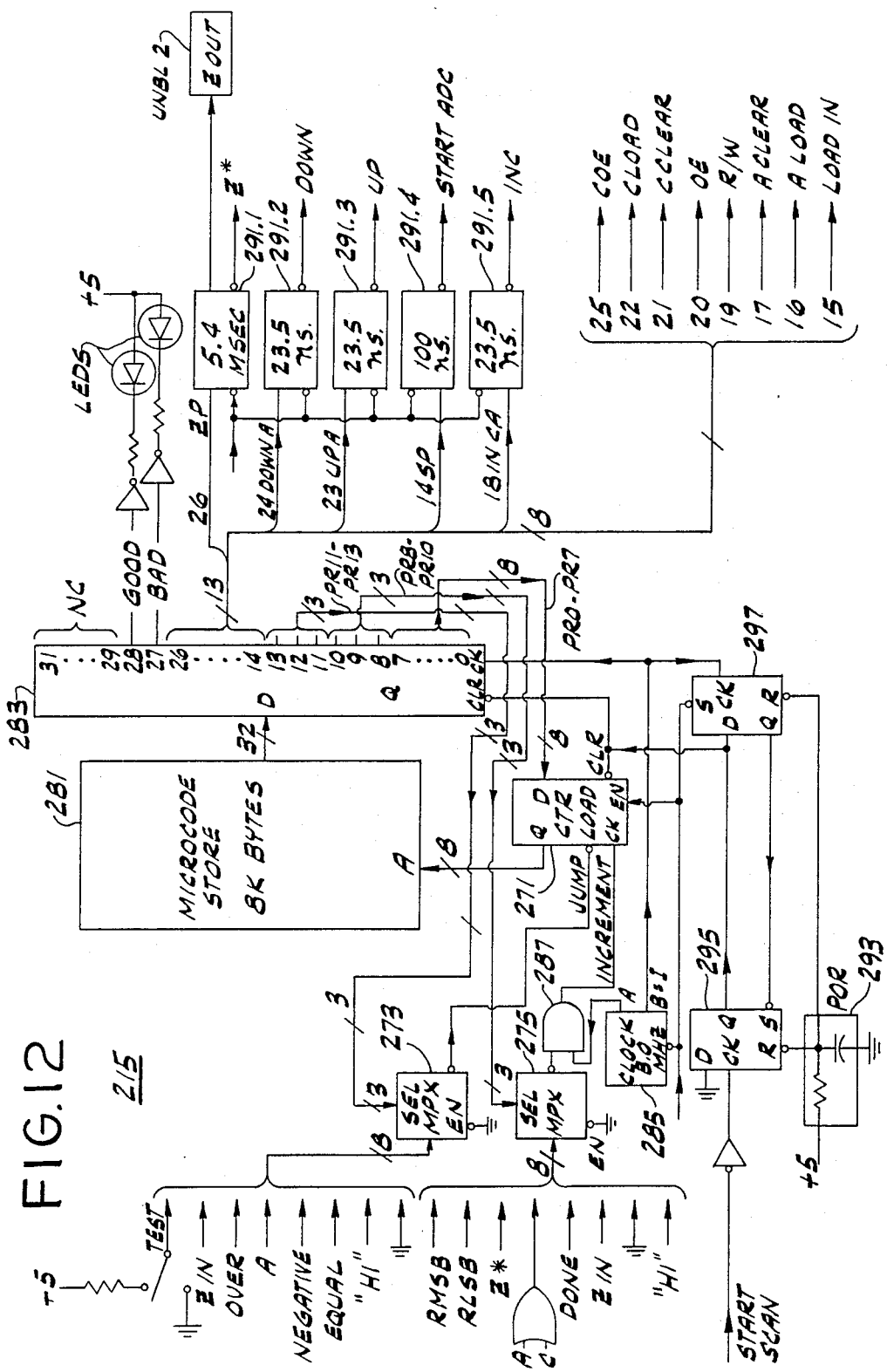

FIG. 11 shows a scatter filter interface 201 which has an analog-to-digital X,Y conversion stage 203, an A event/C event register 205, a memory address generating circuit 207, a memory array 75, an up/down counter 209, a digital comparator 211, and a digital-to-analog X,Y conversion stage 213. A microprogrammable controller 215 for interface 201 of FIG. 11 is shown in FIG. 12.

Analog-to-digital conversion stage 203 has two HAS 1204 analog to digital converters ADC 221 and 223 respectively feeding two 12 bit registers 225 and 227 and associated discrete logic. ADCs 221 and 223 convert X and Y event position signals, which are nominally square analog pulses 4 to 10 microseconds wide, which may be bipolar in some cameras. The HAS 1204 converts a 2.5 to −2.5 volt signal to 12 bits of digital data in 2 microseconds. The status signal ST. of each converter 221 and 223 is used to strobe the respective converter output into the registers 225 and 227. The status signals are also combined in a NOR gate 229 to inform the controller 215 of FIG. 12 when the converters 221 and 223 have valid data.

The A or C signals $A_{IN}$ and $C_{IN}$ from the circuit of FIG. 10 are strobed into an A/C event register 205 until needed. Register 205 is used because the $A_{IN}$ and $C_{IN}$ signals are only valid during the pulse $Z_{IN}$ and the controller 215 executes its operations in a time interval longer than that of 1 microsecond pulse $Z_{IN}$.

Address generation circuit 207 has a 16 bit counter 241 and a 3-to-8-line demultiplexer 243 for memory section selection. A demultiplexer 245 as well as demultiplexer 243 each drive 2 sets 247 and 249 of 8 light emitting diodes (LEDs), to indicate proper function of the interface 201. This combination creates enough address space for a 256 by 256 image in memory 75. Since only 16 bits are needed to create this address space only the top 8 bits of each ADC 221 and 223 are used. If more resolution is needed, then the address counter 241 length is increased and more bits of the ADCs 221 and 223 are used. Three control lines ACLEAR, ALOAD, and INC from controller 215 respectively clear, load, and increment counter 241. One output signal OVER from counter 241 indicates to the PROM controller 215 when and if the address counter 241 has overflowed.

RAM memory 75 is a memory array of eight 6264 (64K by 8 bit) memory chips. Two signals R/W and OE from controller 215 control the reading/writing and the output of the memory 75.

Up/down counter 209 is an 8 bit device with Q outputs fed to an 8-bit A input of comparator 211 and to the input of an 8-bit Schmitt input inverting tri-state buffer 251. Counter 209, comparator 211 and buffer 251 hold the output of the memory array 75, increment or decrement the counter 209, compare the counter contents to those of a memory location and route the counter output back to the memory array 75. The just-mentioned functions are controlled by five signals CCLEAR, CLOAD, UP, DWN AND COE from the PROM controller 215. Two signals EQUAL and NEGATIVE returned to the PROM controller 215 inform the controller of an equal comparator output or a negative value in the counter 209 respectively.

Digital-to-analog conversion stage 213 has two HDH1205 digital to analog converters which receive as input the 12 bit outputs from registers 225 and 227 and convert them into analog outputs Xout and Yout. The output signals UNBL2, Xout and Yout should have the same electrical characteristics and relative timing as signals from the device such as camera 51 with which the interface 201 is used.

In FIG. 12 PROM controller 215 controls interface 201 of FIG. 11. PROM controller 215 has an 8-bit counter 271, two 8-to-1-line multiplexers 273 and 275 and four 2716 EPROMs (350 nanosecond cycle time) acting as a single microcode store 281 with four registers acting as a single 32 bit microcode instruction register 283. Program counter 271 responds to JUMP and INCREMENT instructions respectively derived from multiplexers 273 and 275 which determine which status signal to use to make the control jump or increment. The microcoded program produces a 32 bit instruction word output based on the latest 8-bit Address input from program counter 271, and this 32 bit instruction word output is used to produce the status signals which determine via multiplexers 273 and 275 and program counter 271 the next instruction in the micro-program. In this way the microcode store 281 provides an intelligent control for interface 201 of FIG. 11.

A 3.0 MHz. clock 285 has an output for actuating or incrementing program counter 271 through an AND gate 287, and an inverse output for clocking register 283 to assure synchronization. The clock frequency is preferably in excess of 2.5 MHz so that filtering occurs in real-time using a cycle time interval less than 5 microseconds which is approximately an event processing cycle time for a scintillation camera.

Controller 215 thus has microcode store 281 having addresses and an output for microprogram instructions which supply an unblank signal $Z_{OUT}$ and operate address counter 241. At least one of the microprogram instructions includes a jump address (e.g., at bits PR0-PR7 of register 283) to which operations should jump if a predetermined output (e.g., NEGATIVE or EQUAL) of the comparing circuit 209, 251, 211 occurs. Program counter 271 increments addresses beginning with address $00_H$ and is connected to receive the jump address from the output PR0-PR7 of the microcode store 281 and in turn addresses the microcode store 281 with that jump address when the predetermined output of the comparing circuit occurs to activate a JUMP input of counter 271. In this way the program counter 271 and microcode store 281 cause cycles of operation involving incrementing, decrementing and unblanking. A maximum of 15 microprogram instructions can thus be executed in 5 microseconds, which is adequate for real-time operation with detectors which have event cycles of 5 microseconds or longer.

A set of one-shot circuits 291.1-0.5 provide pulses of desired length (as marked) in response to instruction register 283 outputs ZP, DOWNA, UPA, SP, and INCA. A power-on reset (POR) circuit 293 together with D flip-flops 295 and 297 responsive to a Start Scan input restart the microprogrammable controller 215 as appropriate. Start Scan is connected to the camera 51 Start/Stop line which depending on manufacturer is usually a logic line that is high when the camera is running, low when in stop condition. Upon camera Stop, memory 75 is reinitialized to make all tabular values equal the preset value V0 (e.g. zero) and any other operations needed to prepare for the next camera run are executed. Lines marked P5 are always at a logic high regardless of camera state.

The following Signal Table further describes particular signals used in the circuitry of FIGS. 11 and 12:

SIGNAL TABLE

INPUT SIGNALS
 Ain—signifies an A event
 Cin—signifies a C event
 Zin—signifies valid input data (driven by unblank 1)
 Xin—coordinate position information for X coordinate
 Yin—coordinate position information for Y coordinate
 Start Scan—indicates that camera is ready to start a scan

OUTPUT SIGNALS
 Xout—coordinate position information for scatter-free X coordinate
 Yout—coordinate position information for scatter-free Y coordinate
 Zout—signifies valid output data (unblank 2)

INFORMATIVE SIGNALS
 Done—Analog to digital converters (ADCs) have completed their conversions
 Over—Address register has overflowed
 Negative—Output of up/down counter is negative
 Test—enter test state
 Equal—memory location is equal to contents of up/down counter

CONTROLLING SIGNALS
 PR0–PR7—Address location for a jump instruction
 PR8–PR10—Select lines for program increment instructions
 PR11–PR13—Select lines for program jump instructions
 SP, START ADC—Signal to start ADCs
 LOADIN—Signal to capture the Ain and Cin data
 ALOAD—Signal to load the address register
 ACLEAR—Signal to clear the address register
 INCA, INC—Signal to increment the address register
 R/W—Signal to read or write memory
 OE—Signal to control output enable of memory chips
 CCLEAR—Signal to clear up/down counter
 CLOAD—Signal to load up/down counter
 UPA, UP—Signal to increment up/down counter
 DOWNA, DOWN—Signal to decrement up/down counter
 COE—Signal controlling up/down counter output to memory
 ZP—Signal to create Zout signal, Z* is inverse of Zout
 BAD—Signal to light "Bad" LED
 GOOD—Signal to light "Good" LED The microcoded program which is loaded into the microcode store 281 accomplishes the following flow of steps which are presented in a Microcode Flow Table.

MICROCODE FLOW TABLE

| Step | Description |
|---|---|
| A. | START |
| | BEGIN INITIALIZE MEMORY |
| B. | CLEAR ADDRESS REGISTER & UP/DOWN COUNTER |
| C. | CLEAR MEMORY LOCATION |
| D. | INCREMENT ADDRESS REGISTER |
| E. | ADDRESS OVERFLOW? NO: GO TO STEP C YES: GO TO STEP F |
| F. | CLEAR LAST MEMORY LOCATION |
| | END INITIALIZATION |
| G. | TEST? YES: GO TO STEP T NO: GO ON TO STEP H |
| | BEGIN DATA PROCESSING |
| H. | $Z_{IN}$? NO: GO TO STEP G YES: GO ON TO STEP I |
| I. | $Z_{OUT}$? YES: WAIT UNTIL NO NO: GO ON TO STEP J |
| J. | START ADCs |
| K. | ACDs DONE? NO: WAIT UNTIL YES YES: GO ONTO STEP L |
| L. | LOAD ADDRESS REGISTERS |
| M. | READ MEMORY AND LOAD INTO UP/DOWN COUNTER (DATA REGISTER) |
| N. | "A" EVENT? YES: GO TO STEP R NO: GO ON TO STEP O |
| O. | DECREMENT UP/DOWN COUNTER |
| P. | STORE UP/DOWN COUNTER BACK IN MEMORY |
| Q. | GO BACK TO STEP G |
| R. | NEGATIVE? NO: SEND $Z_{OUT}$, GO TO STEP G YES: GO ON TO STEP S |
| S. | INCREMENT UP/DOWN COUNTER AND GO TO STEP P |
| | END DATA PROCESSING |
| | BEGIN TEST |
| | BEGIN CLEAR |
| T. | CLEAR ADDRESS REGISTER AND UP/DOWN COUNTER |
| U. | CLEAR MEMORY LOCATION |
| V. | INCREMENT ADDRESS REGISTER |
| W. | ADDRESS OVERFLOW? NO: GO BACK TO STEP U YES: GO ON TO STEP X |
| X. | CLEAR LAST MEMORY LOCATION |
| | END CLEAR |
| | BEGIN ZERO READ |
| Y. | READ MEMORY LOCATION |
| Z. | ADDRESS OVERFLOW? YES: GO TO STEP A2 NO: GO ON TO STEP A1 |
| A1. | LOCATION EQUAL? NO: LIGHT BAD LED; END PROGRAM YES: INCR ADDRESS REGISTER AND GO BACK TO STEP Y |
| A2. | LOCATION EQUAL? NO: LIGHT BAD LED; END PROGRAM YES: DECREMENT UP/DOWN COUNTER AND GO TO STEP A3 |
| | END OF ZERO READ |
| | BEGIN ALL ONES TEST |
| | BEGIN ONES WRITE |
| A3. | STORE MEMORY LOCATION |
| A4. | INCREMENT ADDRESS REGISTER |

-continued
MICROCODE FLOW TABLE

| Step | Description |
|---|---|
| A5. | ADDRESS OVERFLOW? |
| | NO: GO BACK TO STEP A3 |
| | YES: GO ON TO STEP A6 |
| A6. | STORE LAST MEMORY LOCATION |
| | END ONES WRITE |
| | BEGIN ONES READ |
| A7. | READ MEMORY LOCATION |
| A8. | ADDRESS OVERFLOW? |
| | YES: GO TO STEP B1 |
| | NO: GO ON TO STEP A9 |
| A9. | LOCATION EQUAL? |
| | NO: LIGHT BAD LED; END OF PROGRAM |
| | YES: INCREMENT ADDRESS REGISTER AND GO BACK TO STEP A7 |
| B1. | LOCATION EQUAL? |
| | NO: LIGHT BAD LED; END OF PROGRAM |
| | YES: LIGHT GOOD LED; END OF PROGRAM |
| | END READ |
| | END TEST |

The apparatus of FIGS. 11 and 12 acts as an example of a means for incrementing or decrementing the tabular value for a particular coordinate position depending on whether the energy signal produced by an occurance of the radiation at that coordinate position satisfies a first or a second predetermined energy condition respectively, and if the tabular value at that coordinate position has reached a preset value then instead producing an unblank signal to actuate the incrementing circuit, whereby that circuit increments the numerical value for that coordinate position in producing numerical values over a period of time for display purposes. The apparatus of FIGS. 11 and 12 also acts together with processor 53 of FIG. 4 as an example of a means responsive to the first and second signals and the coordinate position information for generating numerical values for each coordinate position and storing them in the data storage means, the numerical values being a function of the difference of the number of occurrences of radiation in the first energy range at each coordinate position less a second number proportional to the number of occurrences of radiation in the second energy range at that coordinate position.

The function of Compton Scatter Filter 71 is divided into phases: Calibration modes I and II (AIR and ABSORBER on switch 121 of FIG. 10) to determine first energy range and scatter spectrum respectively, and then an operational mode (RUN). In the RUN mode, camera signals are analyzed "on the fly" (in real-time) and some events are eliminated on the basis of scattering considerations as discussed herein.

Figure 13:
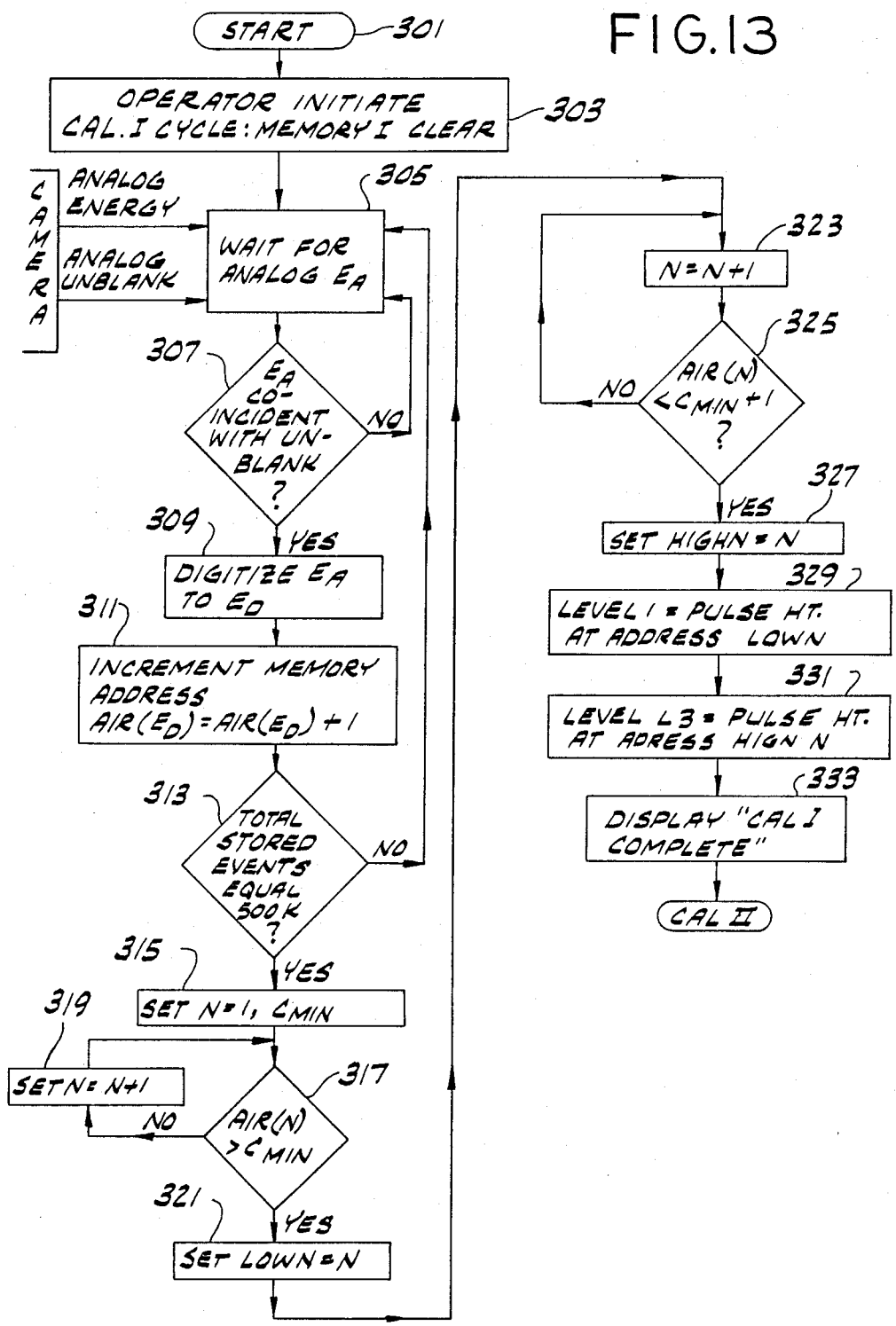
FIG. 13 is a flowchart of operations in the calibrating computer circuit of FIG. 10 according to a method of the invention for measuring a bell-shaped photopeak spectrum of a radioactive test source in air and establishing the first energy range S.

Referring to FIG. 13, operations in a calibration method for calibrating Compton scatter filter 71 and operating microprocessor 103 of FIG. 10 commence with a START 301 when an operator inserts a scatter-free radioactive source in air (e.g., supported on a plastic stand, no scattering medium) into the field of view of gamma camera 51, sets camera 51 for a 20% window on the 140 kev photopeak of Tc-99m for example, selects the camera manual stop mode, starts the camera running, sets mode switch 121 to AIR (Calibration I) and a START switch of FIG. 10 is momentarily depressed. (The camera settings, including the camera manual stop mode are maintained unchanged throughout both Calibration I and II.) Then in a step 303, all spectra in RAM 107 are cleared from areas designated Memory I and II (or AIR and ABR), and in a step 305, the microprocessor 103 waits for an unblank UNBL1 and an energy pulse in commencing to premeasure or collect a new bell-shaped photopeak spectrum like 13 of FIGS. 1 and 3.

Filter 71 now goes into a multichannel analysis (MCA) of the energy signal received from the camera 51 "corrected energy" output. When a peak pulse PEAK from unit 108 is found by AND-gate 119 to be coincident with an unblank from camera 51 in a step 307, operations proceed to step 309 in which each energy event pulse $E_A$ is digitized by ADC 111 to determine a digital pulse height representative of energy level. Also, the memory 107 address AIR($E_D$) which corresponds to the energy pulse height from ADC 111 is incremented by one (1) in a step 311 by interrupt processing of microprocessor 103.

After a predetermined number of events that fall within the camera PHA window (unblank in coincidence with energy pulse) the Calibration I cycle stops the MCA analysis in a step 313 and proceeds to set a memory address index N to 1 in a step 315. Until a predetermined number of events such as 500,000 events occurs, however, operations loop back from step 313 to step 305.

In step 315, a minimum significant number of events $C_{MIN}$ is determined by scanning the photopeak spectrum AIR(N) in memory to determine its peak number $P_N$ of events and then multiplying that peak number by a predetermined fraction or fractions representing the boundaries of the photopeak energy range which was established on the camera 51. Preferably the ratio $C_{MIN}/P_N$ is about one-tenth (0.1) or lies in the range 0.01 to 0.30, so that at least 75% and preferably 90% or more of the actual photopeak events are detected in the S window. For many embodiments the C window is included in the S window, although it is useful in some C-overlap embodiments to allow as much as half or more of the C window to extend to energies below lower energy boundary $e_1$. It is noted that the use of adjacent C and A windows is for the present purposes the same as using an S window equal to the sum of the widths of the C and A windows. Since the shape of the photopeak is based on fundamental properties of the detector material, the boundary fractions are readily predetermined. Also in step 315 any desired smoothing is executed on the photopeak spectrum derived from the raw data.

A search logic searches the memory 107 for channels in the photopeak energy range, as performed by a step 317 which compares memory cell AIR(N) with minimum event number $C_{MIN}$, and incrementing of memory address N in a step 319 until AIR(N) exceeds $C_{MIN}$. When the test of step 317 is met, the memory address corresponding to the low energy boundary $e_1$ of photopeak spectrum 13 of FIG. 3 is thus determined, and the value of N at such time is stored as a number LOWN in a step 321.

Then a procedure searches for the upper energy boundary or limit $e_h$ of the photopeak spectrum of FIG. 3. In a step 323 address index N is incremented by 1 and then a step 325 compares memory 107 contents AIR(N) with $C_{MIN}+1$ and loops back to step 323 until the bell-shaped spectrum falls below $C_{MIN}+1$, whence the value of N is stored as a number HIGHN in a step 327. In some embodiments it is also useful to store values L1 and L3 in a pair of steps 329 and 331 as functions of LOWN and HIGHN to represent the heights of the energy pulses corresponding to lower and upper energy boundaries $e_1$ and $e_h$ respectively. The system has now completed the first calibration cycle Calibration I, and is ready to proceed to the second cycle Calibration II. Accordingly, in a step 333 microprocessor 103 optionally outputs a display message "Cal I Complete" or causes one of the LEDs in FIG. 10 to blink and reaches a point CALII where operations proceed to execute the steps of FIG. 14.

Figure 14:
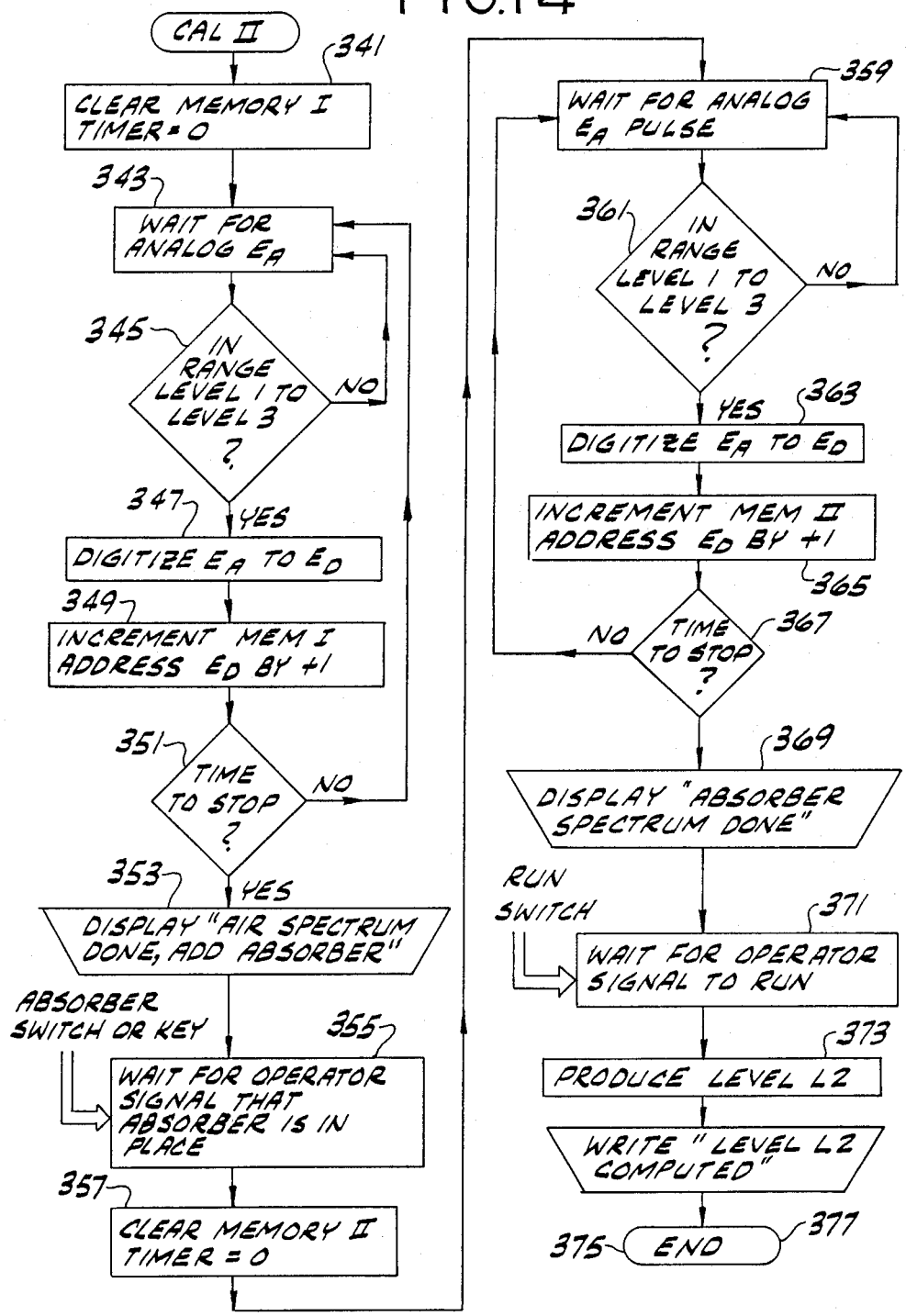
FIG. 14 is a flowchart of further operations in the calibrating computer circuit of FIG. 10 according to a method of the invention for measuring a spectrum of the radioactive test source with an aluminum scattering plate added to produce a spectrum which is the sum of the bell-shaped spectrum and the scatter spectrum in the first energy range S and then producing a signal representing an energy level L2 in the first energy range to establish the dividing line between the A and C windows.
Figure 15:
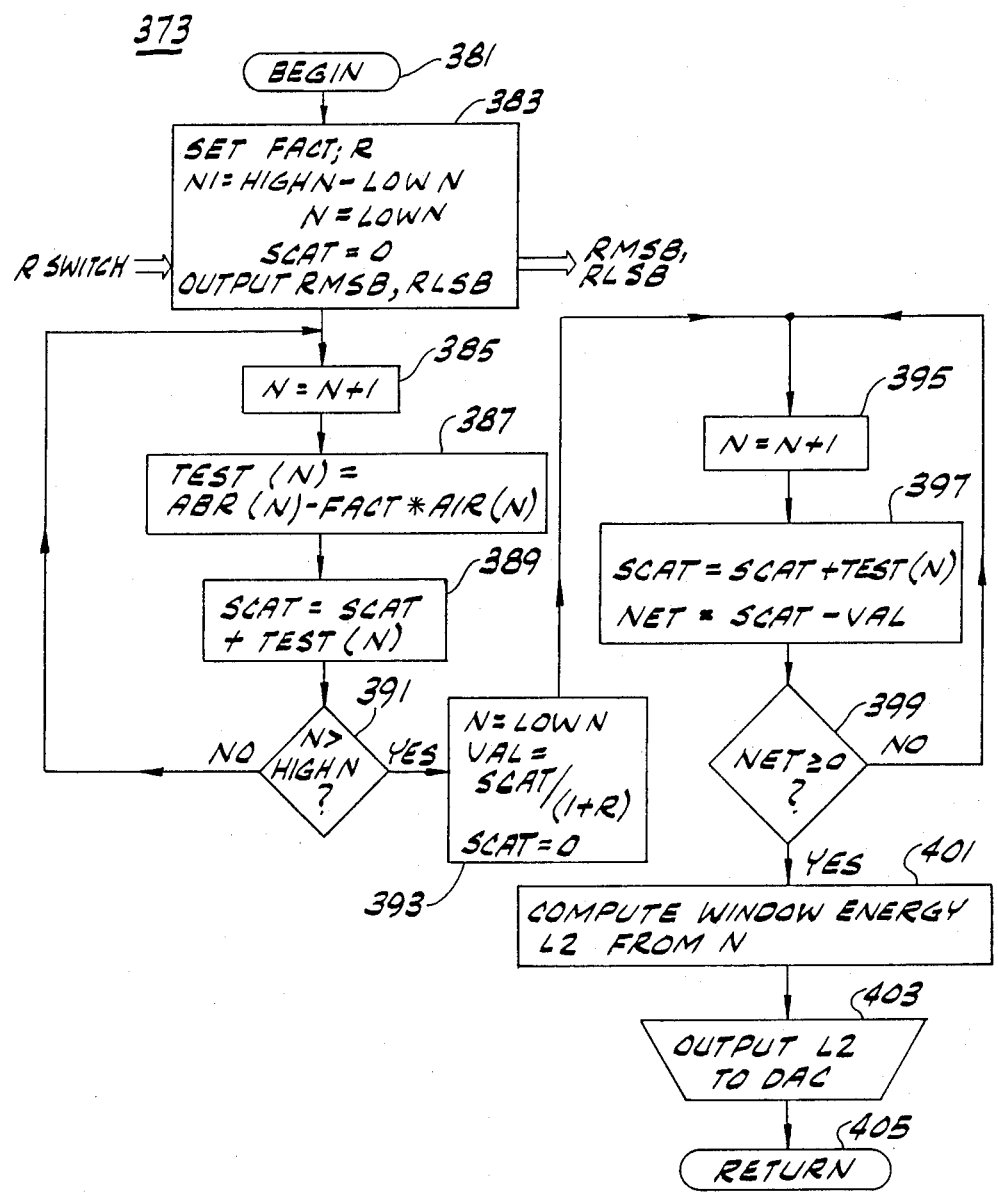
FIG. 15 is a flowchart of further operations in the calibrating computer circuit of FIG. 10 according to a method of the invention for showing in greater detail an inventive method of determining energy level L2 between the A and C windows.

Generally speaking, the Calibration II cycle of FIG. 14 first premeasures or collects the scatter-free photopeak spectrum over a predetermined period of time T, then tells operator to put an aluminum scattering plate in front of any planar camera or in the cylindrical camera 51 between the radioactive source and the detector without disturbing the source, and premeasures or collects a separate spectrum ABR of photopeak plus scatter for the same predetermined period of time T. The predetermined period of time is suitably in the range 1 to 5 minutes, with 4 minutes preferred. Operations are completed by subtracting the scatter-free spectrum from the second spectrum to obtain the scatter spectrum itself. Computations according to FIG. 15 on the scatter spectrum obtained in FIG. 14 determine the level L2 dividing line between the A and C windows of FIG. 3. The steps of FIGS. 14 and 15 are now discussed in step-by-step detail.

In FIG. 14, operations proceed from point CALII to a step 341 to clear the area called Memory I (AIR) in memory 107 which was used in CALI to obtain the photopeak spectrum. A Timer is initialized and set running in microprocessor 103. In a step 343 operations wait for a latest analog energy pulse and if such pulse is in the first energy range L1 to L3 (photopeak range) as indicated by analog unblank on line UNBL1 as determined by AND-gate 119 in a step 345, then a step 347 digitizes the energy $E_A$ pulse to determine an address $E_D$. Then in a step 349 the Memory I location corresponding to address $E_D$ is incremented by 1 and operations continue through a timer test 351 to loop back to step 343 until the timer times out the predetermined time and a spectrum AIR(I) is thus premeasured or collected. Then after step 351, microprocessor 103 outputs a high on line P16 to light a LED 335 labeled "Add Absorber" whence a step 355 is reached.

In step 355 microprocessor 103 waits for the operator to insert the aluminum scattering plate into the camera 51 and to signal that this has been performed by operator selecting the Absorber mode of switch 121. When the Absorber mode is selected, operations proceed to a step 357 to clear the second memory 107 area called Memory II (ABR) and restart the Timer. Then in a series of steps 359, 361, 363, 365 and 367 which exactly correspond to steps 343, 345, 347, 349 and 351, a second spectrum ABR(I) of photopeak plus scatter is collected or premeasured and stored in Memory II. Next, in a step 369, microprocessor 103 outputs an indication of "Absorber Spectrum Done, Remove Absorber" such as by blinking the READY LED 124.

In a next step 371, microprocessor 103 waits for the operator to select RUN on switch 121 to indicate that the aluminum scattering plate absorber is removed. Operations proceed to a step 373 to compute and produce level L2 of FIG. 3 from the spectra AIR and ABR. A step 375 optionally outputs an indication as by illuminating an additional LED that this computation is completed, whence an END 377 is reached. Level L2 is thus output and latched into DAC 112, which operates self-sufficiently after microprocessor 103 reaches END 377.

In FIG. 15 a detail of operations in step 373 of FIG. 14 commences with a BEGIN 381 and proceeds to a step 383 to set a constant FACT. Also in step 383, the setting of switch 131 is read for the value of R, which in turn is output as more and less significant bits RMSB and RLSB. A width of the first energy range in address space is computed as N1 equal to the difference of values HIGHN and LOWN. Address index N is set equal to LOWN. A scatter sum SCAT is initialized to zero.

Then in a loop, the scatter spectrum is computed and the scatter sum in the photopeak window is computed. First in a step 385 index N is incremented by one. Then in a step 387, a scatter spectrum value TEST(N) in a third section of memory 107 is computed as the weighted difference of ABR(N) less the product of AIR(N) with constant FACT. The constant FACT is prestored according to the formula $e^{-ux}$ from the tabulated absorption constant for the scattering plate material at the photopeak energy and the plate thickness x, where e is the base of natural logarithms. For example, FACT is 0.476 for a 1.9 centimeter thick aluminum plate at 140 Kev.

In step 389, the running total of scatter SCAT is increased by the value TEST(N), and in step 391, address index N is tested to determine whether it has exceeded the number HIGHN. If not, operations loop back to step 385, otherwise they proceed to a step 393. In step 393, index N is reset to LOWN. A predetermined fraction $1/(1+R)$ is multiplied by the scatter SCAT and stored as a value VAL of C window scatter. SCAT is reset to zero.

A loop 395, 397, 399 determines the value of N for which the running total of scatter equals the value VAL. In step 395 index N is incremented by one. In step 397 SCAT is increased by the scatter spectrum value TEST(N) and a quantity NET is computed as the difference of SCAT and VAL. If in step 399 the value of NET is less than zero, operations loop back to step 395, otherwise they proceed to a step 401 where they set the window energy number L2 equal to index N just reached in step 395 or compute L2 as a function of N for DAC 112 purposes. Channels LOWN through N for which NET was determined to be negative define the C window portion of the PHA window, and channels N+1 through HIGHN define the A window portion of the S window of FIG. 3.

In a step 403 the value L2 is output and latched to DAC 112 of FIG. 10 which establishes an analog reference level corresponding to L2 for purposes of comparator 113. A RETURN 405 is now reached in FIG. 15. This completes the Calibration II procedure, and the Scatter Filter 71 is ready for operation. A and C events are then determined by comparator logic without microprocessor intervention.

It is useful to recognize that any two of the three lines $Z_{IN}$, $A_{IN}$, and $C_{IN}$ can be used to identify the location of an occurrence of radiation when the scatter window C is contained in S. For example, with C being the lower part of S as in FIG. 3, $Z_{IN}$ indicates whether each value of energy represented by the energy signal at a given time is anywhere in the first energy range S and the $C_{IN}$ signal indicates whether each value of energy represented by the energy signal at a given time is in the lower energy part C of the first energy range S. $Z_{IN}$ and $A_{IN}$ can be analogously used where $A_{IN}$ indicates the higher energy part of the first energy range.

In this way, the circuitry of FIG. 10 acts as an example of a memory means for holding a spectrum of intensity values representing a scatter spectrum together with a means for supplying an electrical reference level representing a predetermined energy in the first energy range of the radiation by premeasuring the scatter spectrum in the first energy range and predetermining the energy at which the total scatter in the first energy range below said energy is substantially equal to a predetermined fraction of the scatter in the first energy range, and means for producing a signal indicating when the energy signal is below or above the electrical reference level. In the RUN mode, the circuitry of FIG. 10 also acts as an example of a means responsive to the energy signal from the detector for producing first and second signals which indicate whether each value of energy represented by the energy signal at a given time is in a first energy range or in a second energy range less than half as wide as the first energy range and having at least some energies in common with the first energy range.

Figure 16:
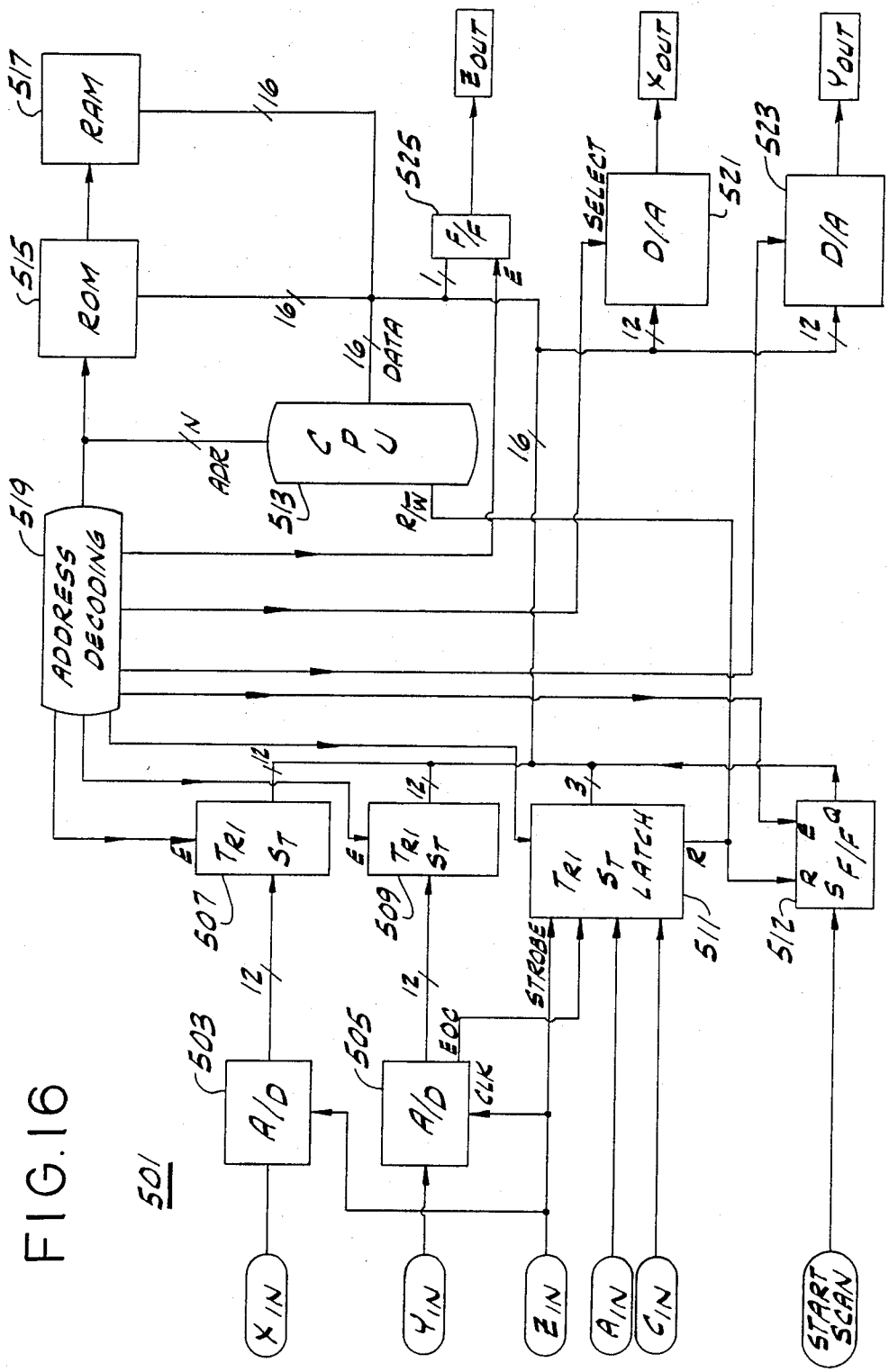
FIG. 16 is a block diagram of an inventive microprocessor-based circuit operating according to inventive methods in substitution for the circuits of FIGS. 11 and 12 in a Compton Scatter Filter of the invention.

In FIG. 16, a microprocessor-based interface and control 501 is an alternative circuit to the interface 201 and control 215 of FIGS. 11 and 12. Inputs $X_{IN}$, $Y_{IN}$, $Z_{IN}$, $A_{IN}$, and $C_{IN}$ are processed to produce outputs $X_{OUT}$, $Y_{OUT}$ and $Z_{OUT}$. Inputs $X_{IN}$ and $Y_{IN}$ are converted to digital form by 12-bit A/Ds 503 and 505, which in turn supply 12-bit tri-state latches 507 and 509. Inputs $A_{IN}$, and $C_{IN}$ are directly connected to another tri-state latch 511 which is strobed by input $Z_{IN}$ and End of Convert EOC from A/D 505. The camera Start Scan input sets a flip-flop 512 which has a tri-state output. Outputs from latches 507, 509 and 511 and flip-flop 512 are coupled onto a data bus of a microprocessor CPU 513, which has associated ROM and RAM memories 515 and 517. An address bus ADR from CPU 513 is connected to ROM 515, RAM 517, and an address decoder 519. CPU 513 produces outputs $X_{OUT}$ and $Y_{OUT}$ by selecting a pair of D/A converters 521 and 523 through decoder 519. $Z_{OUT}$ is clocked out through a flip-flop 525 under control of CPU 513 and decoder 519. CPU 513 is preferably selected to be of a type which is fast enough to process the incoming events in real-time.

Figure 17:
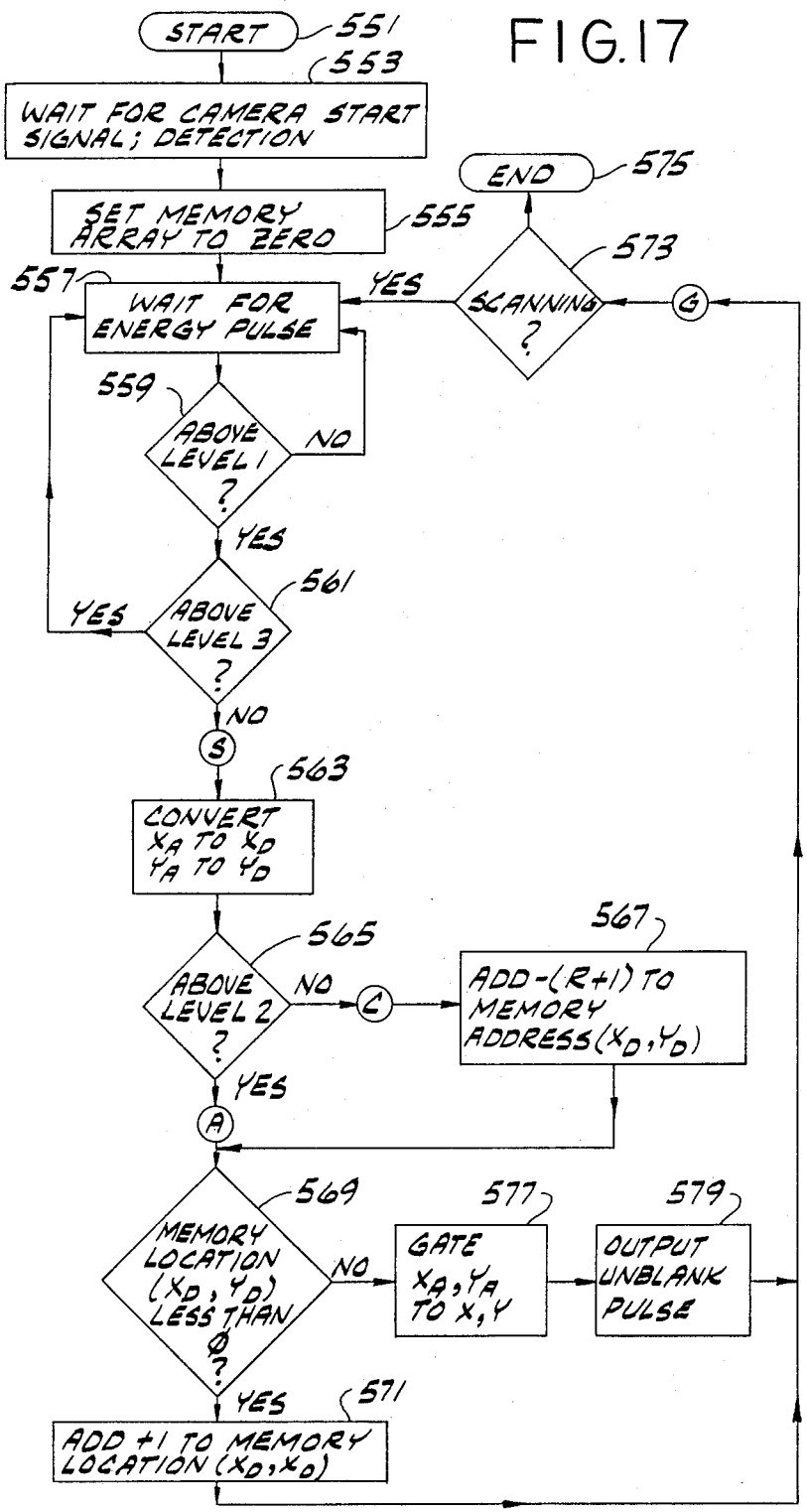
FIGS. 17, 18 and 19 are flowcharts of three alternative inventive methods of operating the apparatus of FIG. 16 for Compton scatter filtering purposes.

In FIG. 17 operations of a filter including CPU 513 of FIG. 16 commence with a START 551 and proceed to a step 553 to wait for the camera Start signal and detection of events. In a step 555 the RAM 517 of FIG. 16 has a section corresponding to the memory of FIG. 5 initialized to zero. Steps 557, 559, 561 wait and screen out all pulses except those in the S window of FIG. 3 which amounts to waiting for a pulse $Z_{IN}$ since these steps are hardware related to camera UNBL1 unblank. When a pulse in the S window occurs, a step 563 converts the coordinate position values X, Y to digital form $X_D, Y_D$ by A/Ds 503 and 505.

In a step 565 CPU 513 determines whether the latest energy pulse is above level L2 by checking $A_{IN}$ and $C_{IN}$. If the energy pulse is in the C window, a step 567 decreases the tabular value at RAM memory address $X_D, Y_D$ by R+1, i.e. adds a negative value $(-(R+1))$. Operations proceed from either step 565 or step 567 to a step 569 to determine whether the value at memory address $X_D, Y_D$ is less than zero. If so, then a step 571 adds a plus one to that memory location, whence a step 573 checks the Start Scan flip-flop 512 to see if it is still set, indicating that the camera 51 is still scanning. If so, operations loop back to step 557, otherwise they reach an END 575.

If in step 569, the value at memory address $X_D, Y_D$ is not less than zero, then operations branch to a step 577 to gate the coordinate position values to outputs $X_{OUT}$ and $Y_{OUT}$ by selecting D/A converters 521 and 523. Next in step 579 an unblank pulse $Z_{OUT}$ is produced by selecting flip-flop 525 whence step 573 is reached.

Operations of FIG. 17 implement the equation S−(R+1)C, and they are designated as a filter method embodiment by the letters S,C.

Figure 18:
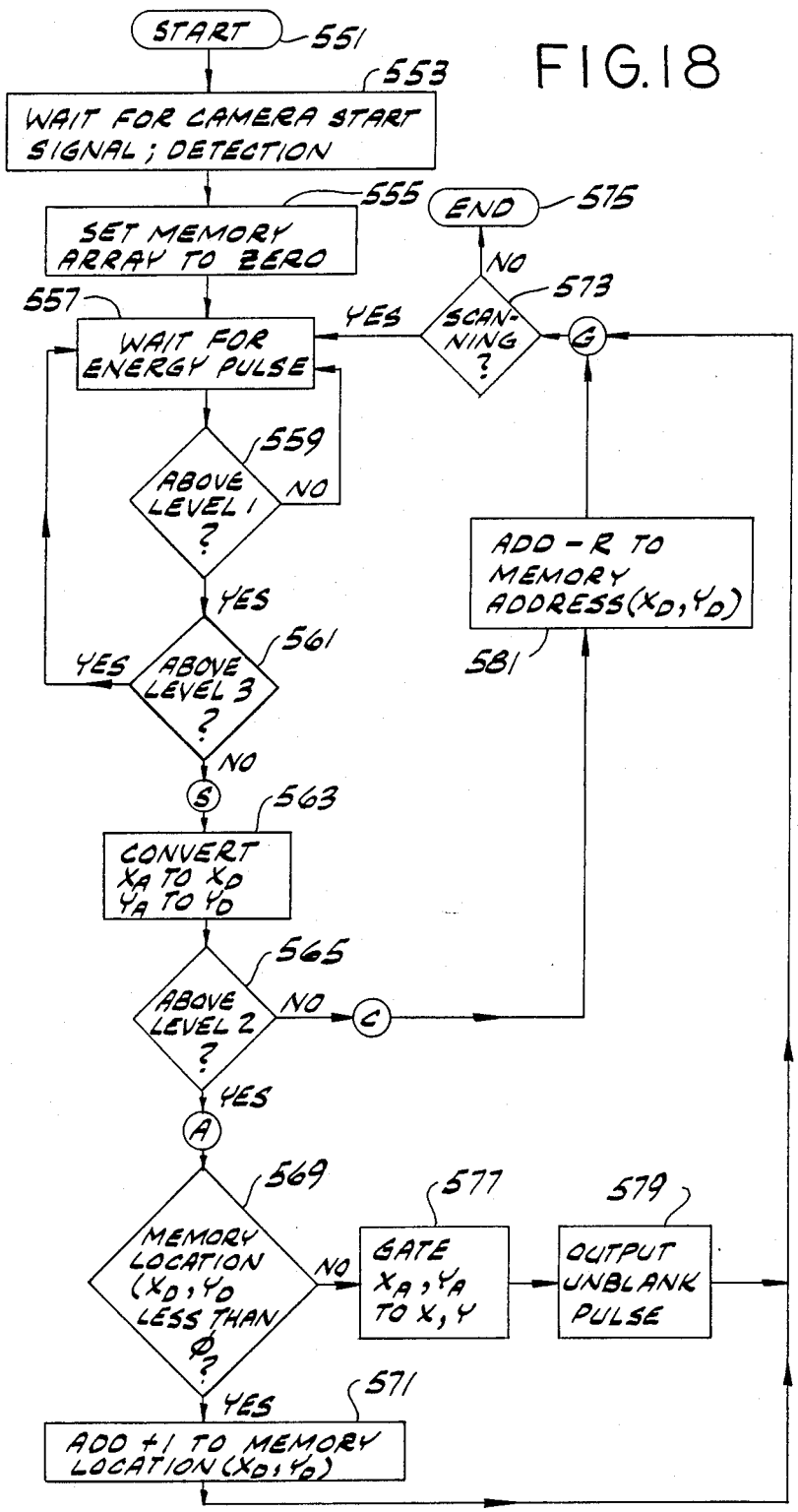

In FIG. 18 an alternative set of operations for microprocessor 513 differs from those of FIG. 17 in that step 567 is omitted and a step 581 is inserted between step 565 and step 573 to subtract R (add (−R)) at memory address $X_D, Y_D$. Operations of FIG. 18 implement the equation A-RC, and they are designated as a filter method embodiment by the letters A,C.

Figure 19:
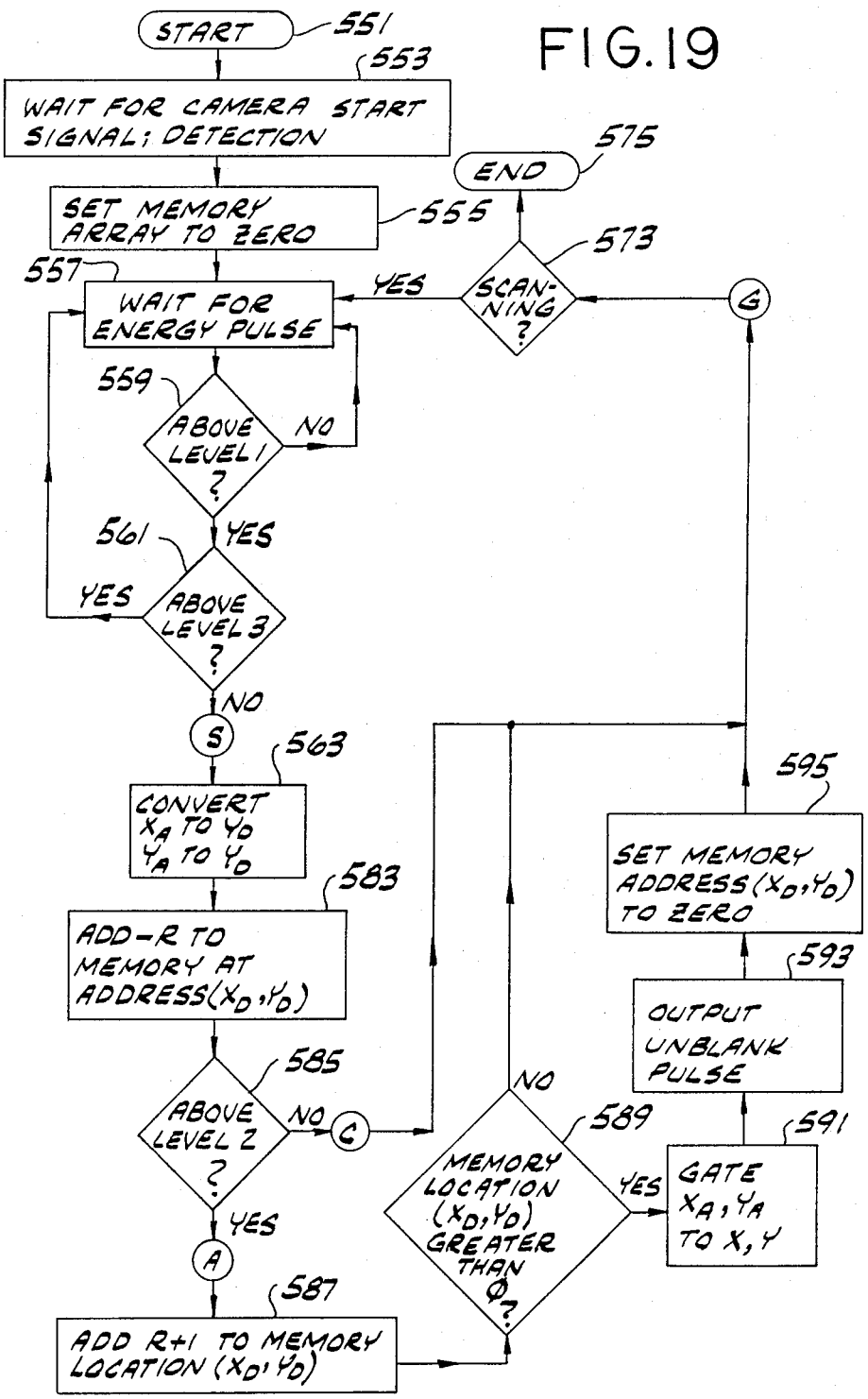

In FIG. 19 another alternative set of operations for microprocessor 513 is the same as described in connection with FIG. 17 for all identically numbered steps. However, upon completion of step 563, operations go to a step 583 to subtract R (add (−R)) at memory address $X_D, Y_D$. Then a step 585 determines whether the latest energy pulse is above level L2 by checking $A_{IN}$ and $C_{IN}$. If the energy pulse is in the C window, operations loop back to SCANNING-test 573. If the energy pulse is in the A window, operations proceed to a step 587 to increase the tabular value at memory address $X_D, Y_D$ by R+1, i.e. adds a positive value $(+(R+1))$. Operations proceed from step 587 to a step 589 to determine whether the value at memory address $X_D, Y_D$ is greater than zero. If not, operations loop back to step 573. Otherwise, a step 591 gates the coordinate position values to outputs $X_{OUT}$ and $Y_{OUT}$ by selecting D/A converters 521 and 523. Next in step 593 an unblank pulse $Z_{OUT}$ is produced by selecting flip-flop 525. Then a step 595 sets the contents of RAM memory address $X_D, Y_D$ equal to zero, whence step 573 is reached.

Operations of FIG. 19 implement the equation (R+1)A-RS, and they are designated as a filter method embodiment by the letters S,A.

In each of FIGS. 4 and 16–19 as well as FIGS. 10–12, the Compton Scatter Filter 71 acts as an example of a combination of means and steps for replacing a value already stored at a particular address in the memory means (e.g., 75 or 517) with a latest value which is the sum of the already-stored value plus a first predetermined value having a first sign, when the energy signal represents a value of energy in a second energy range having at least some energies in common with the first range and less than half as wide as the first range and the radiation occurs at a coordinate position corresponding to that particular address; means for comparing the latest value at the particular address with a preset value when radiation subsequently occurs at the coordinate position corresponding to said address and the energy signal represents a value of energy in a part of the first range outside the second range; and means for supplying the unblank signal and coordinate position information for the radiation to the data storage means (e.g., 55) when the comparing means indicates that the latest value at said address is not less than the preset value when the first sign is negative or when the comparing means indicates that the value at said address is not greater than the preset value when the first sign is positive, and otherwise replacing the latest value at said address with another value equal to the sum of the latest value and a second predetermined value having a second sign opposite to that of the first predetermined value.

Figure 20:
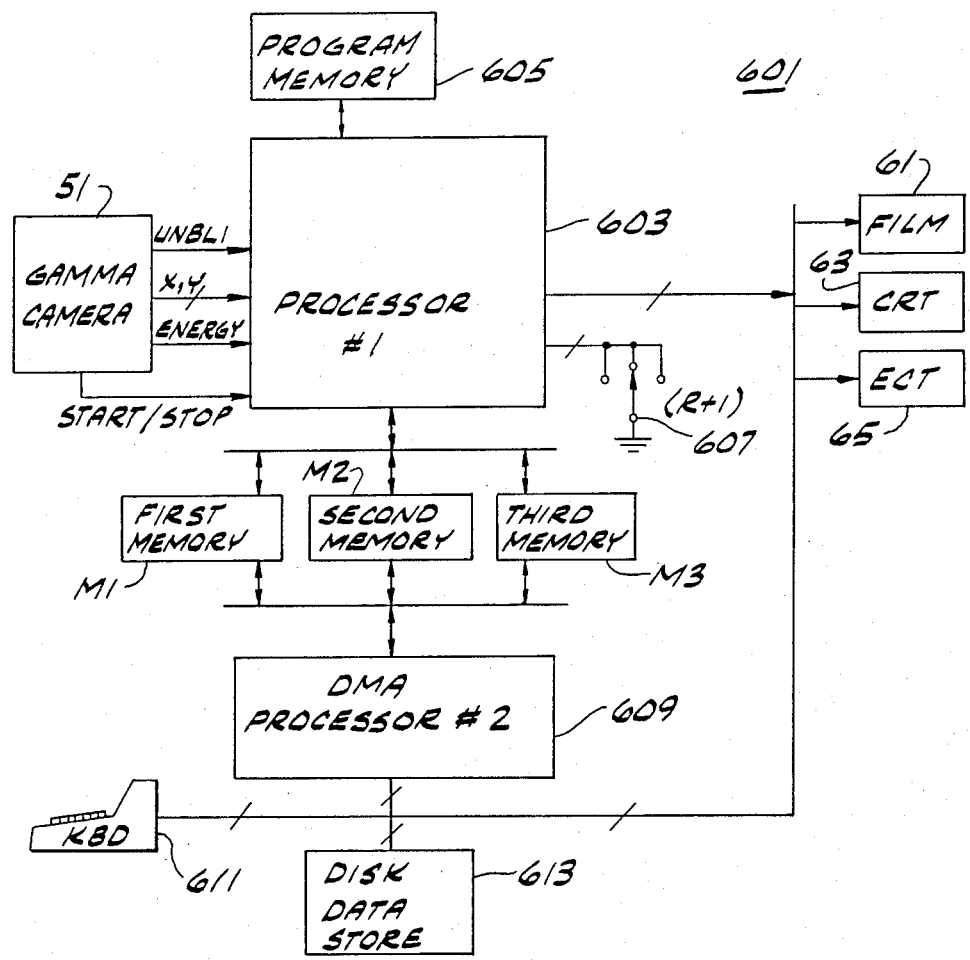
FIG. 20 is a block diagram of an inventive accumulating computer circuit operating according to methods of the invention for reducing Compton scatter in radiation imaging without the use of a separate Compton Scatter Filter apparatus.

In FIG. 20 another system embodiment 601 utilizing one of various accumulation methods now-discussed for scatter reduction according to the invention has a gamma camera 51 and film formatter 61, CRT 63, and ECT 65 as in FIG. 4. Interposed, however, between the camera and the display devices is an improved first processor 603 and program memory 605. Processor 603 is also associated with one, two, or all of three RAM memory areas M1, M2 and M3 for holding arrays of pixel-related data. A multiposition switch 607 sets values of characteristic ratio R+1 for processor 603. A DMA (direct memory access) second processor 609 advantageously accesses memory areas M1, M2 and M3 and performs scatter reduction image processing in some method embodiments while processor 603 is subsequently accumulating more data on a different specimen for example. On command from a terminal keyboard KBD 611, DMA processor 609 stores a scatter-free image in a hard-disk data store 613 and displays the image on one or more of the display devices 61, 63 and 65.

Figure 21:
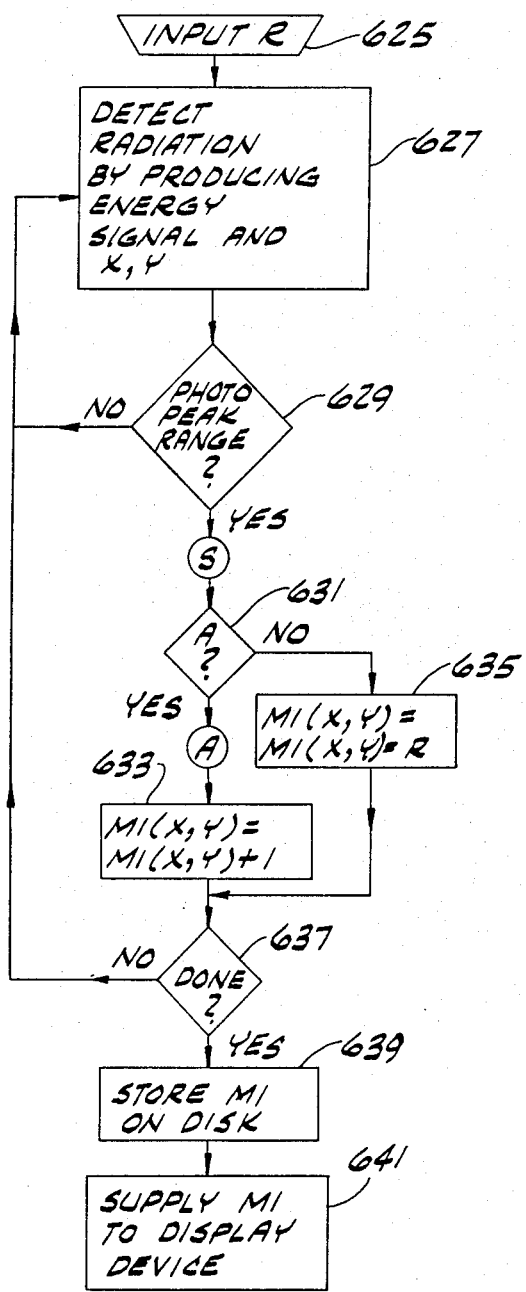
FIGS. 21, 22 and 23 are flowcharts of three alternative inventive methods of operating the accumulating computer circuit of FIG. 20 for reducing Compton scatter in a single memory space M1.

In one A,C method embodiment of FIG. 21 implemented in the processor(s) of FIG. 20, one of the memories M1 collects running computations of A-RC from the camera signals. In this embodiment the determination of A event or C event is entirely digital in processor 603. Operations begin with a step 625 to input a value of characteristic number R. Then camera 51 detects radiation by producing an energy signal and coordinate position information X,Y in a step 627. Camera pulse height analysis determines whether the energy pulse is in the photopeak range, see step 629. If so, operations proceed to a step 631 where processor 603 digitally determines by comparison with the digital value L2 whether an A event or C event has occurred. If an A event occurred then memory M1 is incremented by one at an address corresponding to coordinate position X,Y of the radiation event. If a C event occurred then memory M1 is decremented by characteristic number R at that address corresponding to coordinate position X,Y. Steps 633 and 635 together operate over many events to reduce scatter with image arithmetic according to Equation (9). After either step 633 or 635 operations proceed to a test 637 to determine whether a predetermined time period or other condition is satisfied. If not, then a loop is made back to step 627. Otherwise, operations proceed to a step 639 to store the accumulated scatter free image in memory area M1 onto the disk 613 and to supply the image to one or more of the display devices in a step 641.

Figure 22:
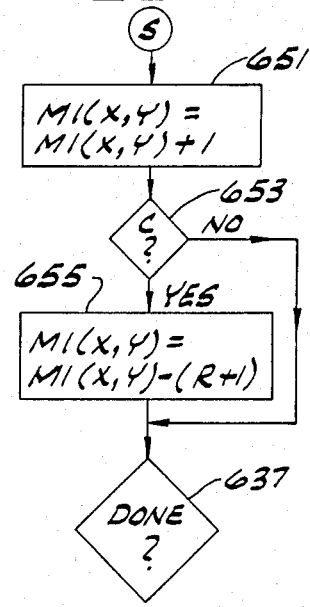

In an S,C method embodiment of FIG. 22 implemented in the processor(s) of FIG. 20, one of the memories M1 collects running computations of S−(R+1)C from the camera signals. In this embodiment the determination of whether a C event occurred is entirely digital in processor 603. Operations are the same as in FIG. 21 except between point S and DONE test step 637. After point S, M1 is incremented by one in a step 651 at an address corresponding to coordinate position X,Y of the radiation event. If a C event occurred per a test step 653, then memory M1 is decremented in a step 655 by characteristic ratio R+1 at that address corresponding to coordinate position X,Y. If there is no C event in step 653 or when step 655 is completed, then test 637 is reached. The steps of FIG. 22 operate over many events to reduce scatter with image arithmetic according to Equation (10).

Figure 23:
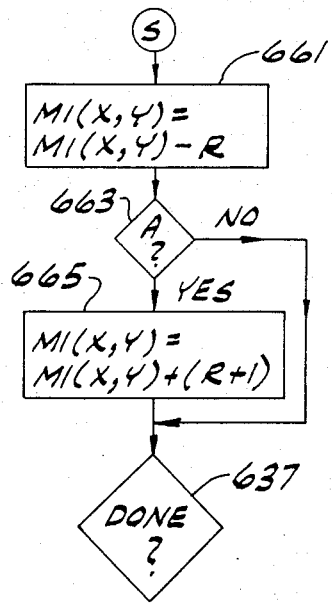

In an S,A method embodiment of FIG. 23 implemented in the processor(s) of FIG. 20, one of the memories M1 collects running computations of (R+1)A-RS from the camera signals. In this embodiment the determination of whether a A event occurred is entirely digital in processor 603. Operations are the same as in FIG. 21 except between point S and DONE test step 637. After point S, M1 is decremented by characteristic number R in a step 661 at an address corresponding to coordinate position X,Y of the radiation event. If an A event occurred per a test step 663, then memory M1 is incremented in a step 665 by characteristic ratio R+1 at that address corresponding to coordinate position X,Y. If there is no A event in step 663 or when step 665 is completed, then test 637 is reached. The steps of FIG. 23 operate over many events to reduce scatter with image arithmetic according to Equation (11).

Figure 24:
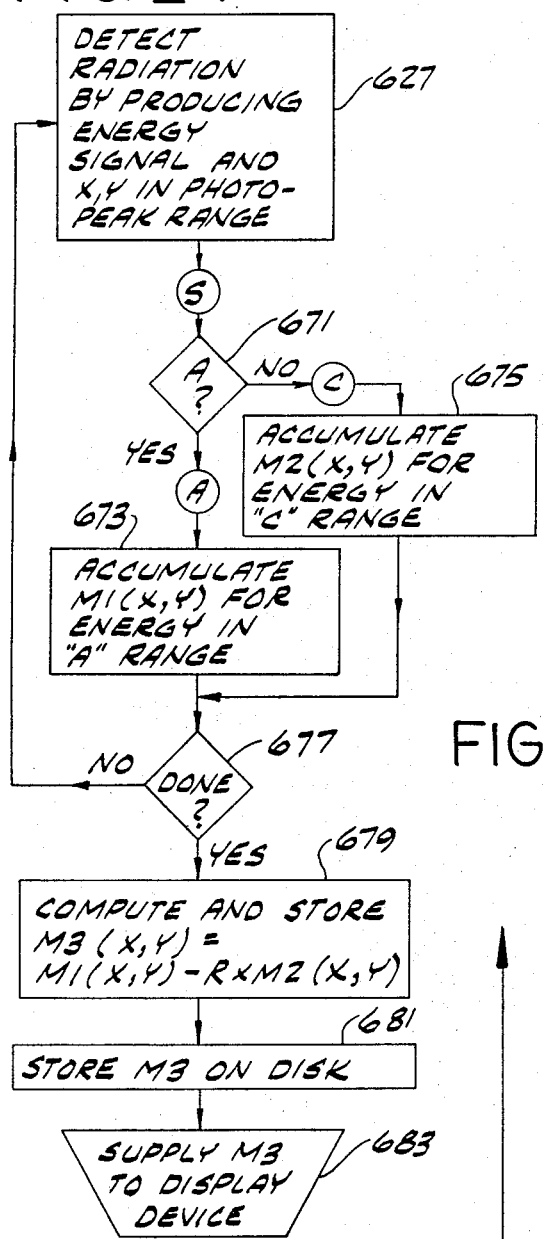
FIGS. 24, 25 and 26 are flowcharts of three alternative inventive methods of operating the accumulating computer circuit of FIG. 20 for reducing Compton scatter using plural memory spaces M1, M2 and M3.

In a further A,C embodiment of FIG. 24 implemented in the system of FIG. 20, two different digital image memories M1 and M2 collect A and C image signals. In this embodiment A and C events are segregated in a test step 671 and used in respective steps 673 and 675 to accumulate a given event in one memory M1 as by incrementing by one at M1(X,Y) if A is high, and to accumulate the event in the other memory M2 as by incrementing by one at M2(X,Y) if C is high. After the imaging or accumulation sequence is complete as determined by a DONE test 677, then a composite scatter free image is formed in a step 679 either by writing over M2 or writing into an additional memory area M3 with image arithmetic for each pixel according to Equation (9) by the formula $M3(X,Y) = M1(X,Y) - R \times M2(X,Y)$. Then a step 681 stores memory area M3 on disk, and a step 683 supplies M3 to a display device.

Figure 25:
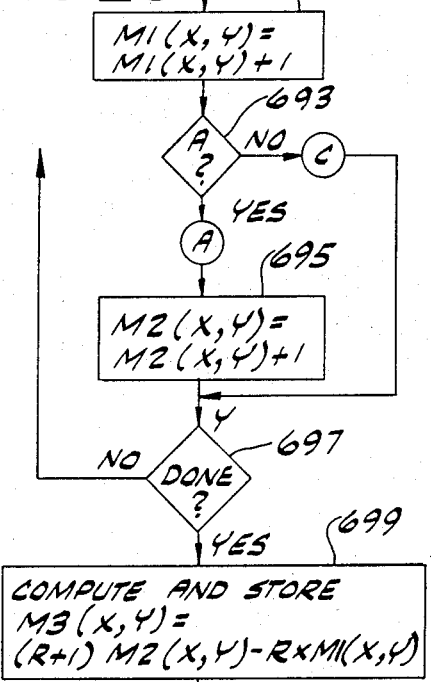

In a further S,A embodiment of FIG. 25 implemented in the system of FIG. 20, two different digital image memories M1 and M2 collect S and A image signals. In FIG. 25 only those steps which differ from FIG. 24 are explicitly shown, the earlier and later identical steps as in FIG. 24 being presumed. After point S is reached in this embodiment the S event is accumulated in memory M1 by incrementing by one in a step 691. Then a step 693 determines whether the S event was also an A event. If so, a step 695 is executed to accumulate the A event in memory M2 by incrementing it by one and going to a DONE test 697 identical to test 677. If there is no A event in step 693 then a branch to DONE test 697 is made. After operations are done they pass from step 697 to a step 699 where a scatter-free image is formed either by writing over M2 or writing into an additional memory area M3 with image arithmetic for each pixel according to Equation (11) by the formula $M3(X,Y) = -R \times M1(X,Y) + (R+1) \times M2(X,Y)$.

Figure 26:
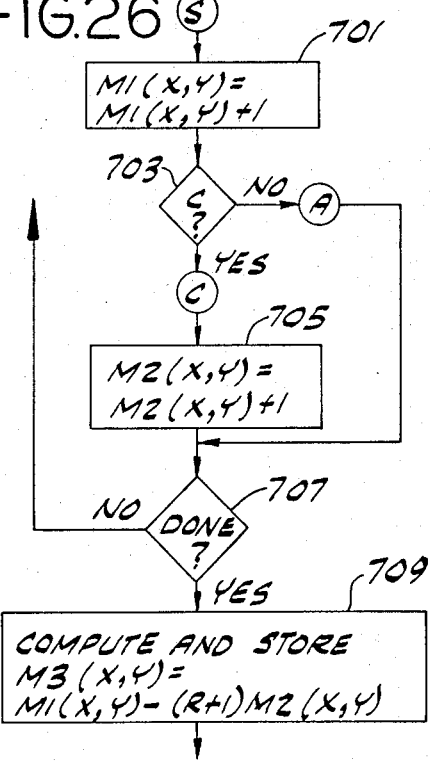

In yet another S,C embodiment of FIG. 26 implemented in the system of FIG. 20, two different digital image memories M1 and M2 collect S and C image signals. In FIG. 26 only those steps which differ from FIG. 24 are explicitly shown, the earlier and later identical steps as in FIG. 24 being presumed. After point S is reached in this embodiment the S event is accumulated in memory M1 by incrementing by one in a step 701. Then a step 703 determines whether the S event was also a C event. If so, a step 705 is executed to accumulate the C event in memory M2 by incrementing it by one and going to a DONE test 707 identical to test 677. If there is no C event in step 703 then a branch to DONE test 707 is made. After operations are done they pass from step 707 to a step 709 where a scatter-free image is formed either by writing over M2 or writing into an additional memory area M3 with image arithmetic for each pixel according to Equation (10) by the formula $M3(X,Y) = M1(X,Y) - (R+1) \times M2(X,Y)$.

Corresponding to each of these just-discussed accumulation embodiments is a scatter filter embodiment (A,C; S,C; or S,A) for either retrofit or original inclusion in camera and nuclear medicine computer electronics already having an image memory ordinarily intended for accumulating S image signals. The scatter filter has an auxiliary memory 75 (like the memory of a multichannel analyzer (MCA)) which removes events imputed to scatter before they reach the main image memory. The auxiliary memory holds the results of image arithmetic done by the scatter filter circuitry in real-time or "on the fly" as the pulses arrive from the camera.

For example, an A,C scatter filter embodiment is described at length in FIG. 18 herein and performs a subtraction by R for each C event and addition by one for an A event except when an unblank is issued because the preset value is already reached, to implement Equation (9). A scatter filter embodiment of FIG. 17 corresponding to the S,C embodiment performs subtraction by R+1 for every C event and addition by one (1) for an S event except when an unblank is issued because the preset value is already reached, to implement Equation (10). A scatter filter embodiment of FIG. 19 corresponding to the S,A embodiment performs subtraction by R for each S event and addition by R+1 for an A event except when an unblank is issued because the preset value is already reached, to implement Equation (11).

The scatter filter embodiments described are each an example of a memory means for storing first and second values corresponding to each coordinate position and means for incrementing or decrementing the first value for a particular coordinate position depending on whether an occurrence of the radiation at that coordinate position satisfies a first or a second predetermined energy condition respectively, and if the first value has reached a preset level then instead incrementing the second value in magnitude and producing the numerical values as a function of the second values resulting over a period of time. The ratio of amounts of decrementing and incrementing is a function of characteristic number R.

It should be readily understood that it is possible to adapt the scatter rejection apparatus and methods into gamma camera and other ionizing radiation imaging systems by changes and additions to the electronics already used in these devices for detection, energy analysis and signal processing and output. However, some of the inventive methods and systems can be practiced by adding the inventive software to an available nuclear medicine computer and setting energy windows on an associated camera by instructions according to the disclosure herein, and without any rewiring of hardware. The system is automatically reconfigured to the inventive form by the software itself. Various embodiments are also readily adapted to cameras with digital electronics that directly provides digital position signals rather than analog, digital PHA output, digital Z/unblank, and digital Start and Stop signals from the imaging device. In such systems the scatter filter embodiments are also readily adapted to produce corresponding digital signals as outputs.

The scatter filter apparatus is in some embodiments advantageously provided as a separate stand-alone device utilized in conjunction with any of many existing gamma camera imaging systems. No additional accessories or computer programming of the existing system is required, and the scatter filter allows all of the existing imaging peripheral devices such as image formatters, computers, real-time displays, etc., to function with no alterations or additional devices.

A further advantage of the scatter filter embodiment is its relative simplicity and speed. In the preferred embodiment shown in FIGS. 10–12 for example, only a few microseconds delay time occurs for any event, and all processing is in real time so that regardless of the type of image acquisition, scatter corrections are always accomplished. Moreover, various calibration and microprogram controlled embodiments disclosed herein are advantageous alternative means of implementing some scatter reduction approaches involving a wide nonoverlapping scatter energy window for which R is less than unity, as elected by the skilled worker.

Yet another advantage of various embodiments is that the function and design are flexible, and can be adapted to almost any kind of ionizing photon imaging procedure, and can be incorporated into the mainframe structure of imaging devices in original equipment manufacture and other circumstances.

Advantageously, various embodiments differentiate the scatter photon flux from the non-scatter photon flux for the pulses created by both types of photons in sodium iodide and other scintillation crystal detectors in the near vicinity of a photopeak portion of the pulse height spectrum. Use of the scatter reduction apparatus and methods is also contemplated with radiation detectors that do not operate by any scintillation principle but provide sufficient imaging information to do scatter reduction.

In some of the embodiments, one or more of the following characteristics are advantageously implemented:

(A) a second scatter window is contained within the photopeak window, i.e. the photopeak window encompasses a second scatter window.

(B) a second scatter window is contained within the photopeak window and has the same lower energy boundary as the photopeak window.

(C) a second scatter window which has a width which is less than half the width of the photopeak window is contained within the photopeak window or at least overlaps the lower energy boundary of the photopeak window.

(D) a second scatter window that is both narrower than and overlapping the photopeak window, is utilized for high correlation of scatter events in both windows.

(E) a second scatter window is used for scatter subtraction with a ratio R not less than unity.

(F) Two adjacent or contiguous windows are used, the upper energy one of which brackets or encompasses a primary energy photopeak, with the lower window receiving some photopeak photons and having a width not greater than the width of the upper window.

Some embodiments simultaneously use two (and perhaps more) similar PHA windows with finite differences in width and in some cases a different central position, but with one PHA window entirely contained in the other, and both PHA windows essentially encompassing a photopeak in the spectrum of energies emitted from the source region, e.g., S and A windows. As a result, the fraction of photon detection events within a measurement sequence that is due to scatter photons is substantially completely separated from the total number of events in each image location, leaving only the fraction that is due to non-scatter photons when the scattered and non-scattered photons are of essentially similar energy ranges in an ionizing photon imaging procedure using sodium iodide crystal detectors or other similar detectors with relatively poor energy resolution.

Also, some embodiments of the invention advantageously recognize that in addition to the photopeak window, a second window should be used which is relatively narrow because the narrow window detects low angle Compton scatter which has a relatively higher correlation with the low angle Compton scatter which is to be eliminated. The approach of these embodiments of the invention is compatible with known gamma cameras and is also advantageous with high signal-to-noise cameras such as the cylindrical camera disclosed in parent application Ser. No. 604,989. It is believed that prior art approaches have proposed in effect to detect higher angle Compton scatter which has a low correlation with the low angle Compton scatter which is to be eliminated. Consequently, the subtraction of such higher angle Compton scatter from the lower angle Compton scatter has unsatisfactorily left a considerable disadvantageous residue of uncorrelated Compton scatter.

In some embodiments of the invention the characteristic number R is advantageously in excess of unity, while it is believed that the subtraction procedures of the prior art have used a factor much less than unity for weighting the scatter. In this further way, the scatter is inventively weighted and subtracted from the scatter in the photopeak frequency range for more effective scatter reduction as a practical matter and importantly without overcompensating the scatter in the image.

Also in some embodiments, the characteristic ratio or constant of proportionality $R+1$ is at least 2 so that numerical values for imaging are produced as a function of a first number of occurrences of radiation in a first energy range less a second number which is at least twice (e.g., $(R+1)$ times) the number of occurrences of radiation in the second energy range at each coordinate position. In a particularly uncomplicated type of embodiment, R is unity, $R+1$ is exactly two, and the imaging calculation is a function of S-2C, A-C, or 2A-S. The use of the word "function" covers methods involving further addition of data from other photopeaks, or background cancellation or other post-processing after the scatter reduction procedures described herein.

A further analysis based on image pixel intensity ratio considerations supports the validity of the present approach as contrasted with a deemphasizer approach.

Inequality (12) below expresses the concept that adding Compton scatter contributions C1 and C2 to true pixel intensities A and B respectively cannot in general produce corresponding pixel intensities $A+C1$ and $B+C2$ which bear the same ratio to each other as true intensity A does to true intensity B:

$$(A+C1)/(B+C2) \text{ not} = A/B \quad (12)$$

Using a scatter window which overlaps or is contained in the photopeak window captures relatively low angle Compton events. These low angle Compton events are more highly correlated with other low angle Compton events in the rest of the photopeak window than high angle Compton events which originate elsewhere in the specimen radioactive source distribution and occupy the wide lower energy spectrum 15 of FIG. 1. However, such a scatter window in the photospeak area in the photopeak area also captures some true photopeak events. The photopeak has width due to variations in electronic structure in scintillation material, for example. A fraction q of true photopeak events in the overlapping or contained subwindow C is independent of source distribution. Consequently, subtracting this fraction q of true photopeak events along with substantially all of the scatter in each pixel suffices to recover an image with pixel intensities in substantially true ratio according to the equation:

$$(A+C1-(C1+qA))/(B+C2-(C2+qB))=A/B \quad (13)$$

By contrast, a deemphasizer approach subtracts a fraction q' of events whether they are Compton events or true photopeak events, and in general no equality with the true ratio A/B can be achieved, as expressed by the inequality $$q'(A+C1)/(q'(B+C2)) \text{ not} = A/B \quad (14)$$

The scatter window is set relatively narrow to be less than half of the width of the photopeak window, and with the characteristic ratio R greater than or equal to unity. It is believed that there is an optimum value of R which results from a balance of at least two competing considerations. First, the C window (scatter window) should be as narrow as possible at the lower end of the photopeak window in order to capture as few true photopeak photons as possible while capturing scatter photons. Also, the C window should be as narrow as possible in order to capture scatter photons which have the greatest amount of correlation with the scatter in the rest of the photopeak window. However, an opposing consideration is that an extremely narrow C window will capture relatively few photons, and statistical fluctuations will introduce a noise which varies inversely with C window width when the A-RC image arithmetic is performed. While a theoretical basis for determining the optimum value of R is not presently available, qualitative considerations indicate that R should be about one or two at a 140 kev photopeak. It is believed that R should be two to four at a 70 kev photopeak of thallium-201 where the energy resolution of a typical scintillator sodium iodide (NaI) is relatively low and Compton scatter in the photopeak window is greater relative to the photopeak photon flux.

The concept of correlation as used herein to describe effectiveness of scatter subtraction is necessarily qualitative in view of the extremely complex actual source distributions of radionuclide encountered in real specimens and patients to be imaged. The correlation concept is derived from the statistical consideration that subtracting one random variable from another random variable only achieves a perfect zero difference when the two random variables are perfectly correlated, i.e. one random variable is a predictable function of the other, as through proportionality or some linear or other relationship generally. When the two random variables with the same average are not perfectly correlated, their difference is a random variable in its own right, with a mean of zero. In the scatter reduction area, this means that unless there is perfect correlation, there will be some pixels that are overcompensated for scatter, some pixels that are undercompensated for scatter, and many pixels that are essentially correctly compensated to eliminate the scatter. If there is perfect correlation, all pixels will be correctly compensated for scatter. Therefore, the correlation between the scatter in the photopeak window and the correlation in the narrow scatter window, which has at least some energies in common with the photopeak window, should be as high as possible in order to correctly compensate the scatter in as many pixels as possible. Using the narrow scatter window and characteristic ratio R in excess of unity as proposed herein appears to provide a substantially improved correlation and consequent scatter reduction which was hitherto unknown and unrecognized by the prior art.

A number of radionuclides emit radiation of more than one energy, and therefore have multiple photopeaks. Advantageously, embodiments of the invention accommodate the multiple photopeaks. This is achieved in one of at least three ways: (1) perform scatter reduction relative to each photopeak; (2) perform scatter rejection for the photopeak with the most Compton scatter and ignore radiation at all other photopeaks; or (3) perform scatter rejection for the photopeak with the most Compton scatter and utilize radiation at one or more other photopeaks for imaging purposes also, since Compton scatter for those photopeaks is relatively less of a problem. Although each of the three approaches is feasible using one or another embodiment of the invention, it is believed that the third approach is relatively inexpensive and provides the highest signal to noise ratio.

Figure 27:
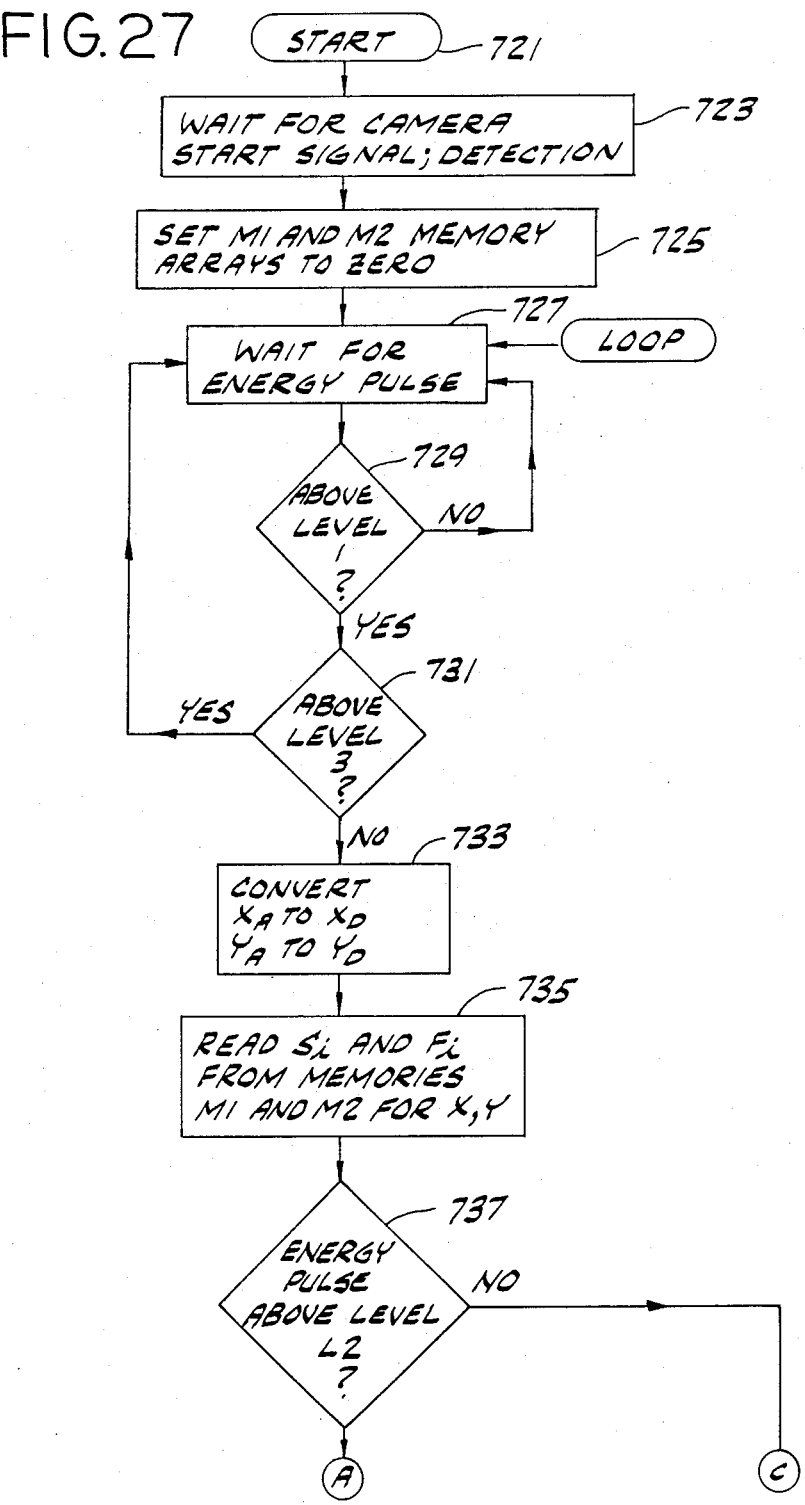
FIGS. 27 and 28 are both halves of a flowchart of a fraction memory process for a further alternative method embodiment to operate the accumulating computer circuit of FIG. 20 for reducing Compton scatter using plural memory spaces M1, M2 and M3.

In a further embodiment of FIG. 27 implemented in the system of FIG. 20, two different digital image memories M1 and M2 collect an image signal and a fraction quantity respectively. Accordingly, this embodiment is called a fraction memory embodiment and operates by recursive computing.

In FIG. 27 operations commence with a START 721 and proceed to a step 723 to wait for the camera Start signal and detection of events. In a step 725 the RAM areas M1 and M2 of FIG. 20 are both initialized to zero. A value in area M1 represents a running total of S events. A value in area M2 represents a latest recursively computed value of a fraction which represents the ratio of scatter-free events to the S events. Steps 727, 729, 731 wait and screen out all pulses except those in the S window of FIG. 3. When a pulse in the S window occurs, a step 733 converts the coordinate position values X, Y to digital form $X_D$, $Y_D$.

Figure 28:
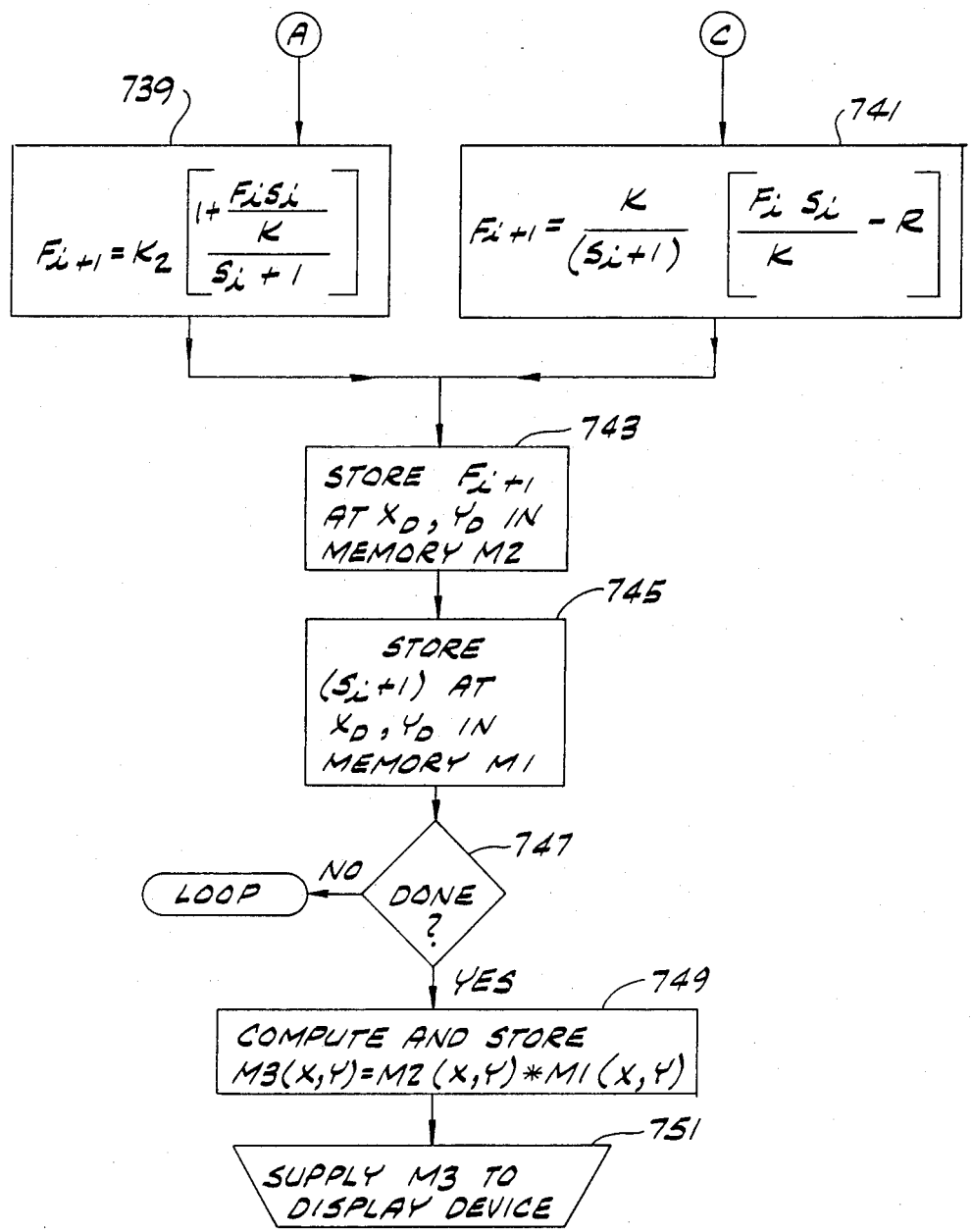

Then in a step 735, latest values of S and the scatter-free fraction F (herein $S_i$ and $F_i$) are read from memory areas M1 and M2 into an electronic scratch-pad. A step 737 determines whether the latest event is in the A or C window and branches to point A or C respectively whereupon a respective recursive computation step 739 or 741 of FIG. 28 is executed to recursively compute a new scatter-free fraction value. It is to be emphasized that no scatter-free count is maintained on a running basis at this point. After either step 739 or step 741, a step 743 stores the new value of $F_{i+1}$ at the address $X_D$, $Y_D$ in memory M2 corresponding to the position of the latest radiation event. Next in a step 745, the count of S events is incremented by 1 and stored at the address $X_D$, $Y_D$ in memory M1 corresponding to the position of the latest radiation event.

A step 747 determines whether a predetermined time period has elapsed for data gathering. If not, operations branch to LOOP of FIG. 27 and step 727. Otherwise, in FIG. 28 operations proceed to a step 749 to compute and store a set of image values corresponding to actual scatter-free counts at the conclusion of data gathering by the product equation $M1(X,Y) = M1(X,Y) \times M2(X,Y)$. Then in a step 751 the scatter-free image data is supplied to one or more display devices of FIG. 20.

A close analysis of the fraction memory concept reveals that at least a dozen different method embodiments are discernible as candidates for software, as set forth in the following Fraction Embodiment Table:

FRACTION EMBODIMENT TABLE

| Fraction | Type | Mnemonic | Arithmetic | Comments |
| --- | --- | --- | --- | --- |
| F1 | C/A | A; C = F1(A) | $A(1 - R \times F1)$ | A, C |
| F2 | C/S | S; C = F2(S) | $S(1 - (R + 1)F2)$ | S, C |
| F3 | A/S | S; A = F3(S) | $S(-R + (R + 1)F3)$ | S, A |
| F4 | A/C | A = F4(C); C | $C(F4 - R)$ | F4 = 1/F1 |
| F5 | S/C | S = F5(C); C | $C(F5 - R + 1)$ | F5 = 1/F2 |
| F6 | S/A | S = F6(A); A | $A(-R \times F6 + (R + 1))$ | F6 = 1/F3 |
| F7 | Scatter-Free | A; F7(A) | $F7 \times A$ | F7 = b1S/A |
| F8 | Scatter-Free | S; F8(S) | $F8 \times S$ | F8 = b1 |
| F9 | Scatter-Free | C; F9(C) | $F9 \times C$ | F9 = b1S/C |
| F10 | Scatter | A; F10(A) | $(1 - F10) \times A$ | F10 = 1 - F7 |
| F11 | Scatter | S; F11(S) | $(1 - F11) \times S$ | F11 = $a_1$ = 1 - F8 |
| F12 | Scatter | C; F12(C) | $(1 - F12) \times C$ | F12 = 1 - F9 |

Some illustrative recursive computation formulas for embodiments F1, F2, F3, F7, F8 and F9 are provided in the following table entitled Fraction Formulas:

FRACTION FORMULA TABLE

| | | | | | |
| --- | --- | --- | --- | --- | --- |
| F1 | IF | A | THEN | $F1_{i+1} =$ | $F1_i A_i/(A_i + 1)$ |
| | IF | C | THEN | $F1_{i+1} =$ | $(1 + F1_i A_i)/A_i$ |
| F2 | IF | A | THEN | $F2_{i+1} =$ | $(1 + F2_i S_i)/(S_i + 1)$ |
| | IF | C | THEN | $F2_{i+1} =$ | $(1 + F2_i S_i)/(S_i + 1)$ |
| F3 | IF | A | THEN | $F3_{i+1} =$ | $(1 + F3_i S_i)/(S_i + 1)$ |
| | IF | C | THEN | $F3_{i+1} =$ | $F3_i S_i/S_i + 1)$ |
| F7 | IF | A | THEN | $F7_{i+1} =$ | $K \dfrac{1 + F7_i A_i/K}{A_i + 1}$ |
| | IF | C | THEN | $F7_{i+1} =$ | $K \dfrac{-R + F7_i A_i/K}{A_i}$ |
| F8 | IF | A | THEN | $F8_{i+1} =$ | $K \dfrac{1 + F8_i S_i/K}{S_i + 1}$ |

FRACTION FORMULA TABLE-continued

|  |  |  |  |  |
|---|---|---|---|---|
|  | IF | C | THEN | $F8_{i+1} = K \dfrac{-R + F8_i S_i/K}{S_i + 1}$ |
| F9 | IF | A | THEN | $F9_{i+1} = K \dfrac{1 + F9_i C_i/K}{C_i}$ |

From inspection of the Fraction Embodiment Table it is apparent that the flowchart of FIGS. 27 and 28 corresponds to the embodiment F8. Embodiment F8 is an example of a means and method for accumulating a first number of occurrences of the radiation at each coordinate position satisfying a predetermined energy condition, and recursively computing a second set of numbers which represents a scatter-related fraction (e.g., a scatter-free fraction or a fraction which represents scatter itself) of each first number. The numerical values are computed as a function of the two numbers so accumulated.

Constant K is discussed later hereinbelow.

A categorization of various embodiments by their scatter reduction arithmetics is set forth in an Arithmetics Table as follows:

ARITHMETICS TABLE

| Linear Embodiment | Accum. FIG. | Filter FIG. | Arithmetic | Mnemonic |
|---|---|---|---|---|
| L1 | 21, 24 | 18 | A − RC | A, C |
| L2 | 22, 26 | 17 | S − (R + 1)C | S, C |
| L3 | 23, 25 | 19 | −RS + (R + 1)A | S, A |

A categorization of various accumulation embodiments by their usage of various memory areas and arithmetics is set forth in an Accumulation Embodiments Table as follows:

ACCUMULATION EMBODIMENTS TABLE

| Accumulation Embodiment | Figures | M1 | M2 | M3 |
|---|---|---|---|---|
| A1 | 21, 22, 23 | Incr., Decr. | — | — |
| A2 | 24, 25, 26 | Incr. | Incr. | Linear Comb. |
| A3 | 27, 28 | Incr. | Fraction | Product Arith. |
| A4 | — | Incr. | Incr.; Linear Comb. | — |
| A5 | — | Incr. | Fraction; Product Arith. | — |

Note:
For each embodiment there are numerous arithmetics for software.

All of the above embodiments are regarded as defining means and methods for recursively computing a first set of numbers in response to occurrences of the radiation at each coordinate position satisfying a first predetermined energy condition, recursively computing a second set of numbers in response to occurrences of the radiation at each coordinate position satisfying a second predetermined energy condition, for subsequently computing the numerical values as a function of the numbers recursively computed and storing the numerical values in the data storing means. Accumulating respective counts of occurrences of the radiation at each coordinate position is regarded herein as a species of recursive computation since each subsequent value is related to a previous value by a given procedure. The fraction updating procedures of steps 739 and 741 of FIG. 28 are of course more complex types of recursive computation than incrementing by one in a counting procedure. The first and second energy conditions are respectively any pair of the three S, C, or A window conditions, for example. "Function" as used in this context includes sums, differences, products, ratios, linear combinations, nonlinear functions, truncations and other mathematical procedures.

To calibrate the imaging system for a2 and b2, the position and width of the photopeak window and its subwindows A and C are selected to optimize the statistical properties of the imaging process, that is to obtain minimal value of a2 and a maximal value of b2.

The constant b2 is determined by imaging a point source in air with each of the two PHA windows separately. The constant a2 is measured by imaging a source in air and also attenuated by one or more known thicknesses of an attenuating medium which has a known attenuation coefficient for the energy of photons emitted by the source. By imaging in air and through the attenuation medium with each of the two PHA windows separately, and using the theoretical attenuation factor to relate the in-air total counts, and the attenuated counts, the constant a2 is then determined. The calibration process is automated by an embodiment of microprocessor-based circuitry, shown in FIG. 10.

Describing the calibration for constant $K = (1 - a_2)/(b_2 - a_2)$, $a_2$ is the fraction of scatter in the S window that falls in the A window. Constant $b_2$ is the non-scatter fraction in the S window that falls in the A window. The following further quantities are defined where their measurements are all made in identical measurement time intervals:

Aair is counts from calibration source in A without absorber.

Sair is counts from calibration source in S window without absorber.

Cair is counts from calibration source in C window without absorber.

Ascatter is counts from calibration source through absorber.

Sscatter is counts from calibration source through absorber.

Constants $a_2$ and $b_2$ are calculated by the formulas $$a_2 = (Ascatter - Aair \times FACT)/(Sscatter - Sair \times FACT) \quad (15)$$

$$b_2 = Aair/Sair = Aair/(Aair + Cair) \quad (16)$$

Since $R = a_2/(1 - a_2)$ by definition, then $$a_2 = R/(R + 1). \quad (17)$$

Figure 29:
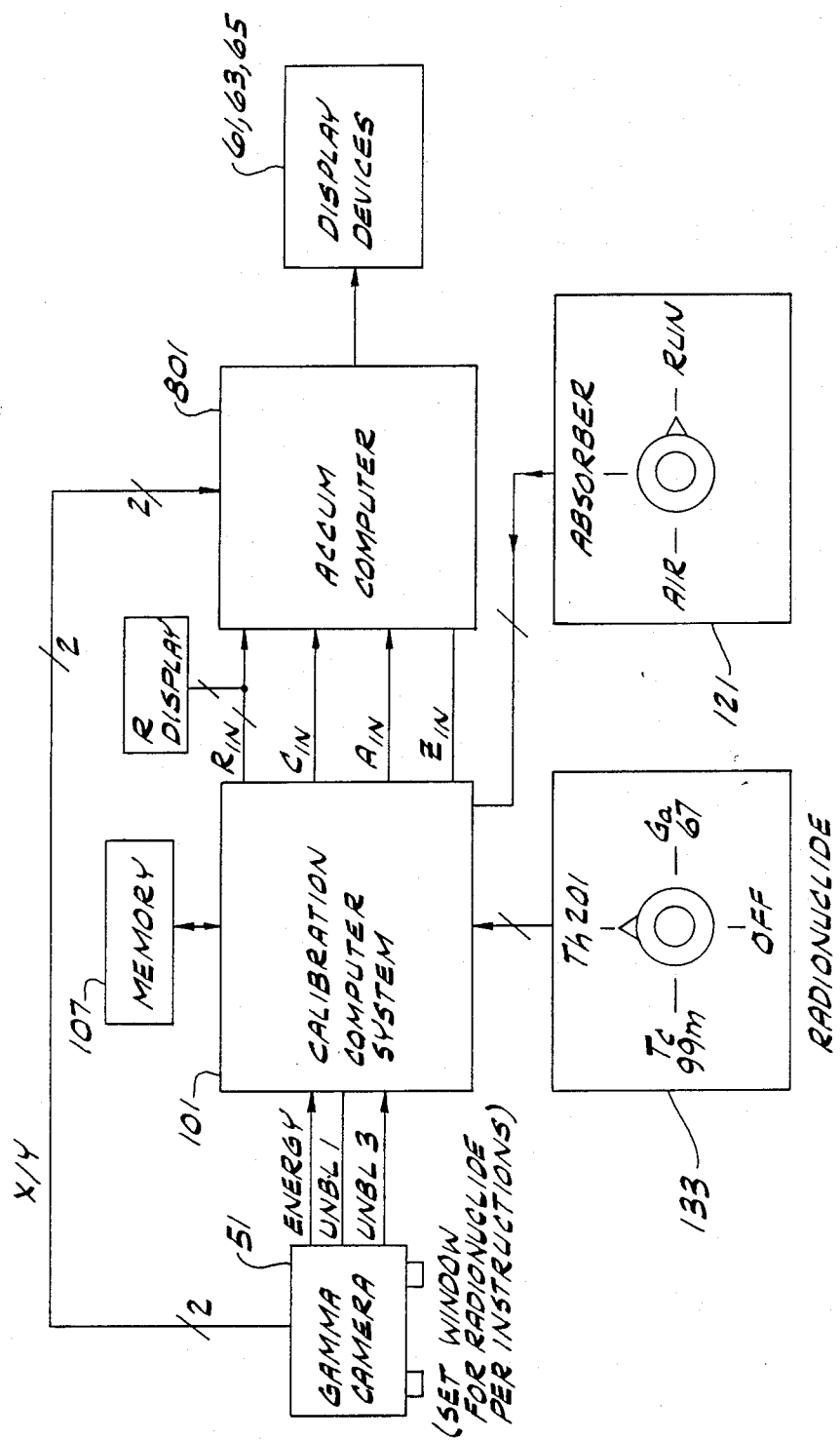
FIG. 29 is a block diagram of a further apparatus embodiment of the invention operating according to methods of the invention and utilizing a Calibration Computer System of FIG. 10 providing computed values of a characteristic ratio R to an accumulating computer operating according to any of flowcharts 21-28.

An accumulating computer 801 in another type of embodiment shown in FIG. 29 receives X,Y coordinate position output signals from gamma camera 51, and the A and C signals from a calibration computer 101 having a memory 107. Computer 801 is a system that operates according to any of the accumulation methods set forth in the Accumulation Embodiments Table hereinabove. Calibration Computer System 101 is identical in circuitry to the same system in FIG. 10 and is programmed to execute the same operations except to the extent discussed in FIG. 30 hereinbelow.

Calibration Computer System 101 receives unblank signals on a line UNBL1 for a photopeak from which scatter is to be removed, and unblank signals on another line UNBL3 from camera 51 for a higher energy photopeak. System 101 produces unblank pulses for computer 801 on a line ($Z_{IN}$). For example, in the parent application Ser. No. 604,989 position coordinates X and Y are output from FIG. 1 processor 31 therein and FIG. 15 processor 517. The unblank, or Z, signal is obtained from the low-active interrupt line INT/ of FIGS. 1 and 15.

In System 101 of FIG. 29, characteristic number R is computed for a preestablished window fraction. The window fraction is preestablished equal to a ratio of the C window width to the A window width, or (L2−L1)/(L3−L1), set by the Radionuclide switch 133. The computed value of R is output through latch 135 of FIG. 10 (or by RS-232 serial line not shown) to the accumulation computer 801. When Radionuclide switch 133 is not OFF, the value on R switch 131 is ignored by microprocessor 103. Radionuclide switch 133 is thus an example of a means for selectively establishing a predetermined fraction (e.g., the window fraction) corresponding to each of a plurality of radionuclides.

The following Radionuclide Table lists relevant data for various radionuclides:

| Radionuclide | RADIONUCLIDE TABLE | | | | |
|---|---|---|---|---|---|
| | Photopeak for Scatter Rej. | (cm$^{-1}$) Al. u | Other Photopeaks | Window Fraction | R |
| Tc-99m | 140 kev. | 0.390 | | 0.3 | 1 |
| Tl-201 | 70 kev | 0.725 | 167 kev | 0.1 | 3 |
| Ga-67 | 93 kev | 0.492 | 185, 300 kev | 0.2 | 2 |

Figure 30:
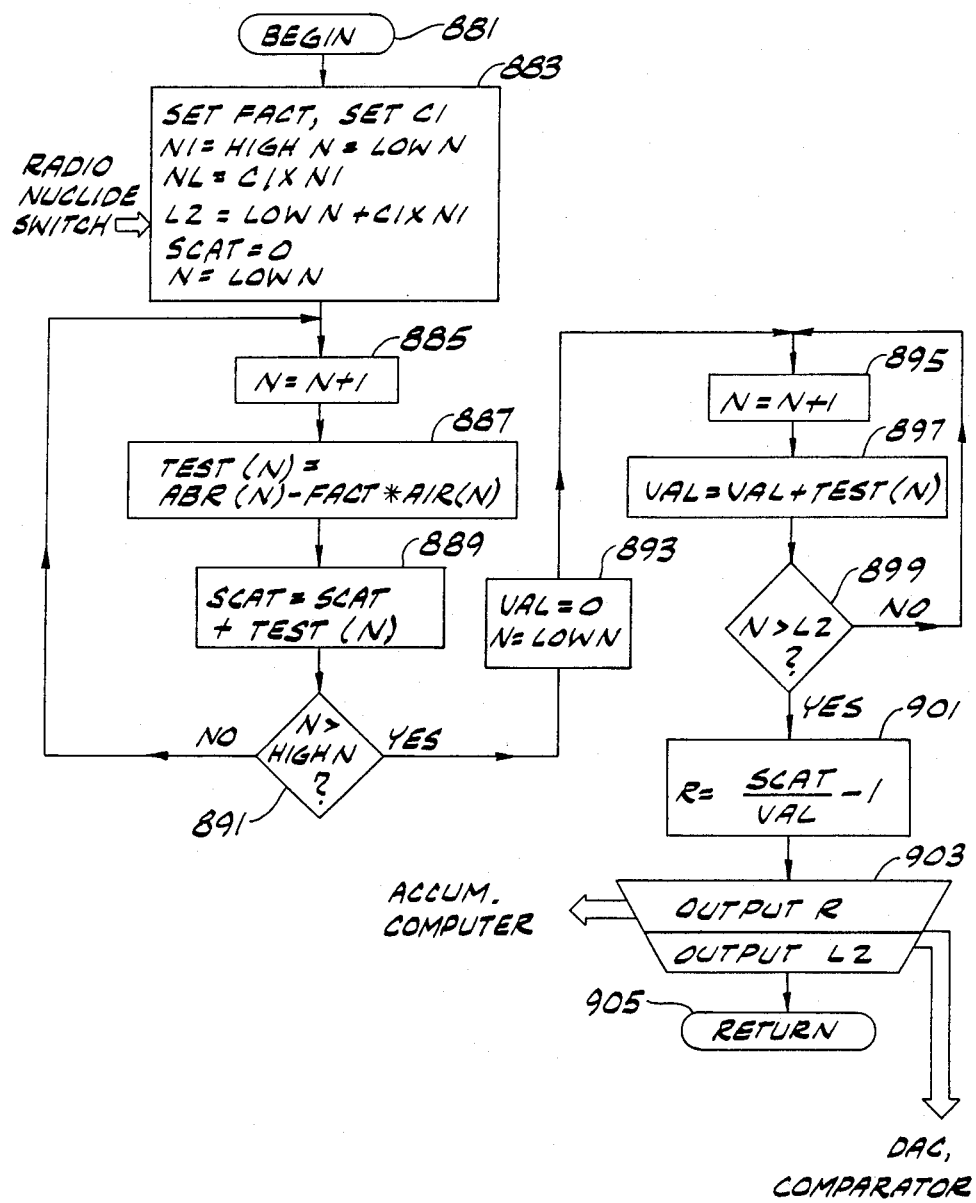
FIG. 30 is a flowchart of operations of the Calibration Computer System of FIG. 10 for use in the apparatus of FIG. 29 in order to compute the values of R.

The setting of Radionuclide switch 133 tells System 101 to utilize the tabulated window fraction in computing R according to FIG. 30.

In FIG. 30 operations as shown are substituted for step 373 of FIG. 14 and entirely replace those of FIG. 15. Operations commence with a BEGIN 881 and proceed to a step 883 to set FACT and address width N1=HIGHN-LOWN as discussed hereinabove for step 383. Index N is set to LOWN. An address width of the C window is computed as the product of width N1 times the tabulated window fraction C1 rom the Radionuclide Table and called for by switch 133. The energy L2 is predetermined by the formula L2=LOWN+C1×N1 rather than being determined from a scatter spectrum as in FIG. 15. Running total SCAT is initialized to zero. Then the scatter spectrum and S window scatter SCAT are computed in a loop 885, 887, 889, 891 which is identical to the loop 385, 387, 389, 391 already discussed in FIG. 15.

After step 891 tests YES, operations proceed to a step 893 to set VAL to zero and reset N equal to LOWN. Next, a loop 895, 897, 899 keeps a running total of scatter as address index N is increased across the C window only. Then operations proceed from step 899 to a step 901 to measure R by computing it as one less than the ratio of total S window scatter SCAT divided by total C window scatter VAL. Then in a step 903 the computed value of R is output through latch 135 to the Accumulation Computer 801, and the value of energy L2 is output to DAC 112 and comparator 113 of FIG. 10, whence a RETURN 905 is reached.

In this way, the Calibration Computer System of FIG. 29 acts as an example of a means for premeasuring the scatter spectrum in the first energy range and producing an electrical signal representing a characteristic number from the scatter spectrum as a function of the ratio of the scatter in the first energy range to the total of the scatter in a predetermined lower energy fraction of the first energy range. Also, the Accumulation Computer 801 acts as an example of a means responsive to the energy signal and the coordinate position information for generating numerical values for each coordinate position and storing them in the data storage means, the numerical values being a function of the difference of the number of occurrences of radiation in the first energy range at each coordinate position less a second number proportional to the number of occurrences of radiation at that coordinate position in a second energy range less than half as wide as the first energy range and having at least some energies in common with the first energy range.

It is apparent that the scatter reducing apparatus and methods can be implemented in numerous alternative embodiments entirely in hardware, in hardware with firmware components, in a computer programmed with software and having associated input and output hardware, and in a microcomputer programmed with software and connected to a radiation detector and display devices with relatively little outboard hardware.

The exposition of a theory of operation with formulas hereinabove describes or motivates some of the preferred embodiments and is not provided to limit or further define the spirit and scope of the invention Illustration of the invention used with a gamma scintillation camera is but one of the combinations contemplated. The invention is also intended for use with positron annihilation cameras, bone mineral densitometry equipment, cameras utilizing radiation detectors that do not operate on a scintillation principle, and for use with display devices and imaging apparatus of numerous different designs and operating principles.

In view of the above, it will be seen that the several objects of the invention are achieved and other advantageous results attained.

As various changes could be made in the above constructions and method steps without departing from the scope of the invention, it is intended that all matter contained in the above description or shown in the accompanying drawings shall be interpreted as illustrative and not in a limiting sense.

What is claimed is:

1. Apparatus for use in reducing scatter in radiation imaging for use with a detector of ionizing radiation, where the ionizing radiation is partly unscattered and partly Compton scattered, the detector producing an energy signal representing values of energy of the ionizing radiation and producing coordinate position information for the ionizing radiation, and where the apparatus is for use with both data storage means for holding numerical values and with means for displaying an image based on the numerical values in the data storage means, the apparatus comprising:

means responsive to the energy signal from the detector for producing first and second signals which indicate whether each value of energy represented by the energy signal at a given time is in a first energy range or in a second energy range less than half as wide as the first energy range and having at least some energies in common with the first energy range; and means responsive to the first and second signals and the coordinate position information for generating numerical values for each coordinate position and storing them in the data storage means, the numerical values being a function of the difference of the number of occurrences of ionizing radiation in the first energy range at each coordinate position less a second number proportional to the number of occurrences of ionizing radiation in the second energy range at that coordinate position.

2. Apparatus as set forth in claim 1 wherein the second energy range is included in the first energy range.

3. Apparatus as set forth in claim 1 wherein the first energy range has a higher energy part and a lower energy part and the second energy range is the lower energy part.

4. Apparatus as set forth in claim 3 wherein the first signal indicates whether each value of energy represented by the energy signal at a given time is in the higher energy part of the first energy range and the second signal indicates whether each value of energy represented by the energy signal at a given time is in the lower energy part of the first energy range.

5. Apparatus as set forth in claim 3 wherein the first signal indicates whether each value of energy represented by the energy signal at a given time is anywhere in the first energy range and the second signal indicates whether each value of energy represented by the energy signal at a given time is in the lower energy part of the first energy range.

6. Apparatus as set forth in claim 3 wherein the first signal indicates whether each value of energy represented by the energy signal at a given time is anywhere in the first energy range and the second signal indicates whether each value of energy represented by the energy signal at a given time is in the higher energy part of the first energy range.

7. Apparatus as set forth in claim 1 wherein the second number is at least twice the number of occurrences of radiation in the second energy range at each coordinate position.

8. Apparatus as set forth in claim 1 wherein the second number is equal to twice the number of occurrences of radiation in the second energy range at each coordinate position.

9. Apparatus as set forth in claim 1 wherein the second number is related by a constant of proportionality to the number of occurrences of radiation in the second energy range at each coordinate position and the apparatus further comprises means for selectively establishing the constant for the generating means.

10. Apparatus as set forth in claim 9 wherein said means for producing the first and second signals includes means for varying the second energy range in width as a function of the constant selectively established.

11. Apparatus as set forth in claim 1 wherein said means for producing the first and second signals includes means for supplying an electrical reference signal representing a predetermined energy in the first energy range, and means for comparing the energy signal with the electrical reference signal to produce the first and second signals respectively depending on whether the energy signal represents an energy which is greater or less than the predetermined energy.

12. Apparatus as set forth in claim 1 wherein the second number is related by a proportionality constant to the number of occurrences of radiation in the second energy range at each coordinate position and said means for producing includes means for supplying an electrical reference signal for comparison with the energy signal, the electrical reference signal representing a predetermined energy in the first energy range to define an upper limit of the second energy range as a function of the proportionality constant.

13. Apparatus as set forth in claim 12 further comprising means connected to said means for producing for adjustably establishing the proportionality constant.

14. Apparatus as set forth in claim 1 wherein the second number is related by a proportionality constant to the number of occurrences of radiation in the second energy range at each coordinate position and said means for producing further includes means for supplying an electrical reference signal for comparison with the energy signal, the electrical reference signal representing a predetermined energy in the first energy range as a function of the proportionality constant, by premeasuring a scatter spectrum in the first energy range and predetermining the energy at which the total scatter in the first energy range below said energy is substantially equal to the scatter in the first energy range divided by the proportionality constant.

15. Apparatus as set forth in claim 1 wherein said means for generating includes means for recursively computing a first set of numbers in response to occurrences of the radiation at each coordinate position satisfying a first predetermined energy condition, recursively computing a second set of numbers in response to occurrences of the radiation at each coordinate position satisfying a second predetermined energy condition, for subsequently computing the numerical values as a function of the numbers recursively computed and storing the numerical values in the data storing means.

16. Apparatus as set forth in claim 1 wherein said means for generating includes means for accumulating respective counts of occurrences of the radiation at each coordinate position satisfying a first predetermined energy condition, recursively computing a set of numbers corresponding to each coordinate position in response to occurrences of the radiation at each coordinate position satisfying a second predetermined energy condition, for subsequently computing the numerical values as a function of the accumulated counts and of the numbers recursively computed and storing the numerical values in the data storing means.

17. Apparatus as set forth in claim 1 wherein said means for generating includes means for accumulating first and second counts of occurrences of the radiation at each coordinate position satisfying first and second predetermined energy conditions respectively, subsequently computing the numerical values as a function of the first and second counts and storing the numerical values in the data storing means.

18. Apparatus as set forth in claim 1 wherein said means for generating includes memory means for storing values corresponding to each coordinate position and means for incrementing or decrementing the value for a particular coordinate position depending on whether an occurrence of the radiation at that coordinate position satisfies a first or a second predetermined energy condition respectively, and for producing the numerical values as a function of the values resulting from the incrementing and decrementing over a period of time.

19. Apparatus as set forth in claim 1 wherein said means for generating the numerical values includes a memory and means connected to said producing means and said memory for accumulating a first set of numbers of occurrences of the radiation at each coordinate position when the energy signal represents a value of energy in the first energy range, and a second set of numbers of occurrences of the radiation at each coordinate position for which occurrences the energy signal represents a value of energy in the second energy range; said accumulating means including means for computing the numerical values as a function of the two numbers so accumulated for each particular coordinate position and storing the numerical values in the data storage means.

20. Apparatus as set forth in claim 1 wherein said means for generating the numerical values includes a memory and means connected to said producing means and said memory for accumulating a first set of numbers of occurrences of the radiation at each coordinate position for which occurrences the energy signal represents a value of energy in the second energy range, and a second set of numbers of occurrences of the radiation at each coordinate position for which occurrences the energy signal represents a value of energy in the first energy range and not the second energy range; said accumulating means including means for computing the numerical values as a function of the two numbers so accumulated for each particular coordinate position and storing the numerical values in the data storage means.

21. Apparatus as set forth in claim 1 wherein said means for generating the numerical values includes a memory and means connected to said producing means and said memory for accumulating a first set of numbers of occurrences of the radiation at each coordinate position when the energy signal represents a value of energy in the first energy range, a second set of numbers of occurrences of the radiation at each coordinate position for which occurrences the energy signal represents a value of energy in the first energy range and not the second energy range, said accumulating means including means for computing the numerical values as a function of the two numbers so accumulated for each particular coordinate position and storing the numerical values in the data storage means.

22. Apparatus as set forth in claim 1 wherein said means for generating includes memory means for storing first and second values corresponding to each coordinate position and means for incrementing or decrementing the first value for a particular coordinate position depending on whether an occurrence of the radiation at that coordinate position satisfies a first or a second predetermined energy condition respectively, and if the first value has reached a preset level then instead incrementing the second value in magnitude and producing the numerical values as a function of the second values resulting over a period of time.

23. Apparatus as set forth in claim 1 wherein said means for generating includes memory means for storing first and second values corresponding to each coordinate position and means for incrementing or decrementing the first value for a particular coordinate position depending on whether the energy signal for an occurrence of radiation at that coordinate position represents an energy that is respectively greater or less than a predetermined energy in the first energy range, and if the first value has reached a preset level then instead incrementing the second value in magnitude and producing the numerical values as a function of the second values resulting over a period of time.

24. Apparatus as set forth in claim 1 wherein said means for generating includes:
  memory means for storing values at respective addresses corresponding to coordinate positions of the radiation;
  means for replacing a value already stored at a particular address in the memory means with a latest value which is the sum of the already-stored value plus a first predetermined value having a first sign, when the energy signal represents a value of energy in the second energy range and the radiation occurs at a coordinate position corresponding to that particular address;
  means for comparing the latest value at the particular address with a preset value when radiation subsequently occurs at the coordinate position corresponding to said address and the energy signal represents a value of energy in a part of the first range outside the second range;
  means for supplying an unblank pulse and coordinate position information for the radiation when the comparing means indicates that the latest value at said address is not less than the preset value when the first sign is negative or when the comparing means indicates that the value at said address is not greater than the preset value when the first sign is positive, and otherwise replacing the latest value at said address with another value equal to the sum of the latest value and a second predetermined value having a second sign opposite to that of the first predetermined value; and
  means connected to said supplying means for accumulating counts of the occurrences of the unblank pulse corresponding to each coordinate position and storing a function of the counts as the numerical values.

25. Apparatus as set forth in claim 1 further comprising a memory having addresses and stored contents corresponding to particular coordinate positions of the radiation and wherein said means for generating the numerical values includes means responsive to the coordinate position information and to the first and second signals for decrementing the contents of the memory at a particular address when radiation having an energy value in the second energy range occurs at a coordinate position corresponding to that address, for incrementing the contents of the memory at that particular address when radiation having an energy value in the first range occurs at a coordinate position corresponding to that particular address, and when the memory contents exceed a preset value, supplying an unblank pulse and coordinate position information for the radiation; and further comprising means for accumulating a function of the number of occurrences of the unblank pulse corresponding to each particular coordinate position as the numerical values.

26. Apparatus as set forth in claim 25 wherein each instance of incrementing increases the contents at the particular address by a first amount and each instance of decrementing decreases the contents at the particular address by a second amount which is at least twice the first amount.

27. Apparatus as set forth in claim 1 further comprising a memory having addresses and stored contents corresponding to particular coordinate positions of the radiation and wherein said means for generating the numerical values includes means responsive to the coordinate position information and to the first and second signals for decrementing the contents of the memory at a particular address when radiation having an energy value in the second energy range occurs at a coordinate position corresponding to that address, for incrementing the contents of the memory at that particular address when radiation having an energy value in the first range and not the second range occurs at a coordinate position corresponding to that particular address, and when the memory contents exceed a preset value, supplying an unblank pulse and coordinate position information for the radiation; and further comprising means for accumulating a function of the number of occurrences of the unblank pulse corresponding to each particular coordinate position as the numerical values.

28. Apparatus as set forth in claim 27 wherein each instance of incrementing increases the contents at the particular address by a first amount and each instance of decrementing decreases the contents at the particular address by a second amount which is at least equal to the first amount.

29. Apparatus as set forth in claim 1 further comprising a memory having addresses and stored contents corresponding to particular coordinate positions of the radiation and wherein said means for generating the numerical values includes means responsive to the coordinate position information and to the first and second signals for incrementing the contents of the memory at a particular address when radiation having an energy value in the first energy range but not the second energy range occurs at a coordinate position corresponding to that address, for decrementing the contents of the memory at that particular address when radiation having an energy value in the first range occurs at a coordinate position corresponding to that particular address, and when the memory contents exceed a preset value, supplying an unblank pulse and coordinate position information for the radiation; and further comprising means for accumulating a function of the number of occurrences of the unblank pulse corresponding to each particular coordinate position as the numerical values.

30. Apparatus as set forth in claim 1 wherein said means for generating the numerical values includes a memory and means connected to said producing means and to said memory for accumulating a first set of numbers of occurrences of the radiation at each coordinate position satisfying a predetermined energy condition, and recursively computing a second set of numbers which represents a scatter-related fraction of each first number, said accumulating means including means for computing the numerical values as a function of the two numbers so accumulated for each particular coordinate position and storing the numerical values in the data storing means.

31. Apparatus as set forth in claim 30 wherein said scatter-related fraction is a scatter-free fraction.

32. Apparatus as set forth in claim 30 wherein said scatter-related fraction is a fraction which represents scatter itself.

33. Apparatus as set forth in claim 30 wherein said first set of numbers represents the number of occurrences of radiation in the first energy range for each coordinate position.

34. Apparatus as set forth in claim 30 wherein said first set of numbers represents the number of occurrences of radiation in the second energy range for each coordinate position.

35. Apparatus as set forth in claim 30 wherein said first set of numbers represents the number of occurrences of radiation in the first energy range and not the second energy range for each coordinate position.

36. Apparatus as set forth in claim 1 wherein said means for generating the numerical values includes a memory and means connected to said producing means and said memory for accumulating the first number of occurrences of the radiation at each coordinate position when the energy signal represents a value of energy in the first energy range, and recursively computing another number representing a fraction of the first number which represents that part of the first number of occurrences at each coordinate position which is the number of occurrences of the radiation with a value of energy in the second energy range at each same coordinate position, said accumulating means including means for computing the numerical values as a function of the two numbers so accumulated and computed for each coordinate position and storing the numerical values.

37. Apparatus as set forth in claim 1 wherein said means for generating the numerical values includes a memory and means connected to said producing means and to said memory for accumulating a number of occurrences of the radiation at each particular coordinate position when the energy signal represents a value of energy in the first energy range and not the second energy range, and a second number representing a fraction with respect to the accumulated number for occurrences of the radiation with a value of energy in the second energy range at each same coordinate position, said accumulating means including means for computing the numerical values as a function of the accumulated number and the fraction for each particular coordinate position and storing the numerical values in the data storage means.

38. Apparatus for use in reducing scatter in radiation imaging of ionizing radiation where the ionizing radiation has a photopeak in a first energy range and where the apparatus is for use with data storage means for holding numerical values and with means for displaying an image based on the numerical values in the data storage means, the apparatus comprising:
  means for detecting ionizing radiation that is partly unscattered and partly Compton scattered to produce an energy signal representing values of energy of the ionizing radiation in the first energy range and to produce coordinate position information for the ionizing radiation; and
  means responsive to the energy signal and the coordinate position information for generating numerical values for each coordinate position and storing them in the data storage means, the numerical values being a function of the difference of the number of occurrences of ionizing radiation in the first energy range at each coordinate position less a second number proportional to and at least two times the number of occurrences of ionizing radiation at that coordinate position in a second energy range.

39. Apparatus as set forth in claim 38 wherein the second energy range is included in the first energy range.

40. Apparatus as set forth in claim 38 wherein the first energy range has a higher energy part and a lower energy part and the second energy range is the lower energy part.

41. Apparatus as set forth in claim 38 wherein the second energy range is less than half as wide as the first energy range and has at least some energies in common with the first energy range.

42. Apparatus as set forth in claim 38 wherein the second number is related by a constant of proportionality to the number of occurrences of radiation in the second energy range at each coordinate position and the apparatus further comprises means for selectively establishing the constant for the generating means.

43. Apparatus as set forth in claim 42 wherein said means for generating includes means for varying the second energy range in width as a function of the constant selectively established.

44. Apparatus as set forth in claim 38 wherein said means for generating includes means for recursively computing a first set of numbers in response to occurrences of the radiation at each coordinate position satisfying a first predetermined energy condition, recursively computing a second set of numbers in response to occurrences of the radiation at each coordinate position satisfying a second predetermined energy condition, for subsequently computing the numerical values as a function of the numbers recursively computed and storing the numerical values in the data storing means.

45. Apparatus as set forth in claim 38 wherein said means for generating includes means for accumulating respective counts of occurrences of the radiation at each coordinate position satisfying a first predetermined energy condition, recursively computing a set of numbers corresponding to each coordinate position in response to occurrences of the radiation at each coordinate position satisfying a second predetermined energy condition, for subsequently computing the numerical values as a function of the accumulated counts and of the numbers recursively computed and storing the numerical values in the data storing means.

46. Apparatus as set forth in claim 38 wherein said means for generating includes means for accumulating first and second counts of occurrences of the radiation at each coordinate position satisfying first and second predetermined energy conditions respectively, subsequently computing the numerical values as a function of the first and second counts and storing the numerical values in the data storing means.

47. Apparatus as set forth in claim 38 wherein said means for generating includes memory means for storing values corresponding to each coordinate position and means for incrementing or decrementing the value for a particular coordinate position depending on whether an occurrence of the radiation at that coordinate position satisfies a first or a second predetermined energy condition respectively, and for producing the numerical values as a function of the values resulting from the incrementing and decrementing over a period of time.

48. Apparatus as set forth in claim 38 wherein said means for generating includes memory means for storing first and second values corresponding to each coordinate position and means for incrementing or decrementing the first value for a particular coordinate position depending on whether an occurrence of the radiation at that coordinate position satisfies a first or a second predetermined energy condition respectively, and if the first value has reached a preset level then instead incrementing the second value in magnitude, and producing the numerical values as a function of the second values resulting over a period of time.

49. Apparatus as set forth in claim 38 wherein said detecting means has an event processing cycle time and said means for generating includes memory means for storing first and second values corresponding to each coordinate position and means for incrementing or decrementing the first value for a particular coordinate position depending on whether the energy signal for an occurrence of radiation at that coordinate position represents an energy that is respectively greater or less than a predetermined energy in the first energy range, and if the first value has reached a preset level then instead incrementing the second value in magnitude, and producing the numerical values in real time within a cycle time interval less than the event processing cycle time of said detecting means and as a function of the second values resulting over a period of time.

50. Apparatus as set forth in claim 49 wherein said means for generating further includes means for supplying an electrical reference signal representing the predetermined energy in the first energy range, and means connected to the means for incrementing or decrementing for comparing the energy signal with the electrical reference signal.

51. Apparatus as set forth in claim 49 wherein the second number is related by a proportionality constant to the number of occurrences of radiation in the second energy range at each coordinate position and said means for generating further includes means for supplying an electrical reference signal representing the predetermined energy in the first energy range as a function of the proportionality constant.

52. Apparatus as set forth in claim 51 further comprising means connected to said means for generating for adjustably establishing the proportionality constant.

53. Apparatus as set forth in claim 49 wherein the second number is related by a proportionality constant to the number of occurrences of radiation in the second energy range at each coordinate position and said means for generating further includes means for supplying an electrical reference signal representing the predetermined energy in the first energy range as a function of the proportionality constant by premeasuring a scatter spectrum in the first energy range and predetermining the energy at which the total scatter in the first energy range below said energy is substantially equal to the scatter in the first energy range divided by the proportionality constant.

54. Apparatus for use in reducing scatter in ionizing radiation imaging comprising:
   means for detecting ionizing radiation that is partly unscattered and partly Compton scattered by producing an energy signal representing values of energy of the ionizing radiation and producing coordinate position information for the ionizing radiation;
   means responsive to the energy signal from the means for detecting ionizing radiation for producing first and second signals which indicate whether each value of energy represented by the energy signal at a given time is in a first energy range or in a second energy range which is less than half as wide as the first energy range and which has at least some energies in common with the first energy range;
   data storage means for holding numerical values;
   means responsive to the first and second signals and the coordinate position information for generating numerical values for each coordinate position and storing them in the data storage means, the numerical values being a function of the difference of the number of occurrences of ionizing radiation in the first energy range at each coordinate position less a second number proportional to the number of occurrences of ionizing radiation in the second energy range at that coordinate position; and means for displaying an image based on the numerical values in the data storage means.

55. Apparatus for use in reducing scatter in radiation imaging for use with a detector of ionizing radiation, where the ionizing radiation is partly unscattered and partly Compton scattered, the detector producing an energy signal representing values of energy of the ionizing radiation and producing coordinate position information for the ionizing radiation, and where the apparatus to be used with data storage means for holding numerical values corresponding to each coordinate position, with a circuit for incrementing each corresponding numerical value in response to an unblank signal and the coordinate position information, and with means for then displaying an image based on the numerical values in the data storage means, the apparatus comprising:

memory means for storing tabular values corresponding to each coordinate position;

means for incrementing or decrementing type tabular value for a particular coordinate position depending on whether the energy signal produced by an occurrence of the ionizing radiation at that coordinate position satisfies a first or a second predetermined energy condition respectively, and if the tabular value at that coordinate position has reached a preset value then instead producing an unblank signal to actuate the incrementing circuit, whereby that circuit increments the numerical value for that coordinate position in producing numerical values over a period of time for display purposes.

56. Apparatus as set forth in claim 55 wherein the memory means is initialized to the preset value for each of the coordinate positions.

57. Apparatus as set forth in claim 55 wherein the first and second predetermined energy conditions relate to a first energy range having a center energy value and a width less than one fourth of the center energy value and the first predetermined energy condition comprises the energy signal representing an energy in the first energy range above a predetermined energy value in that range, and the second predetermined energy condition comprises the energy signal representing an energy in the first energy range less than the predetermined energy value.

58. Apparatus as set forth in claim 57 wherein said means for incrementing or decrementing decrements by an amount which exceeds the amount by which it increments at each coordinate position.

59. Apparatus as set forth in claim 55 wherein said means for incrementing or decrementing includes:

counter means having an input connected to said memory means and an output for communicating to said memory means, means for supplying an address to said memory means corresponding to the coordinate position information in response to an occurrence of the radiation to cause said memory means to supply said counter means with a tabular value from the address, means for comparing the tabular value with the preset value, and means for supplying the unblank signal when the comparing means indicates that the tabular value is equal to the preset value if the energy signal represents an energy in a first energy range above a predetermined energy in that range, and otherwise operating said counter means to decrement the tabular value when the energy is less than the predetermined energy or increment the tabular value when the energy is greater than the predetermined energy, and storing the result from said counter means in said memory means as an updated tabular value at the address for that coordinate position.

60. Apparatus as set forth in claim 59 wherein said means for supplying and operating includes microcode store means having addresses and an output for microprogram instructions which supply the unblank signal and operate said counter means, at least one of the microprogram instructions including a jump address to which operations should jump if a predetermined output of said comparing means occurs, and program counter means for incrementing addresses and connected to receive the jump address from the output of said microcode store means and for addressing said microcode store means with the jump address when the predetermined output of said comparing means occurs, and clock circuit means connected to said program counter means for actuating said program counter means and said microcode store means to execute cycles of operation in the incrementing or decrementing means at a rate in excess of one million cycles per second.

61. Apparatus as set forth in claim 55 wherein said means for incrementing or decrementing includes electronic circuit means for supplying the unblank signal and for executing operations on the tabular values in less than five millionths of a second in order to reduce the scatter as rapidly as occurrences of radiation are detected in the detector.

62. Apparatus as set forth in claim 55 wherein the means for decrementing and incrementing has a characteristic ratio of amount of each decrementing to amount of each incrementing and the apparatus further comprises means for supplying an electrical reference level representing a predetermined energy in a first energy range of the radiation by premeasuring a scatter spectrum in the first energy range and predetermining the energy at which the total scatter in the first energy range below said energy is substantially equal to the scatter in the first energy range divided by a number which is a function of the characteristic ratio, and means for signalling the means for decrementing or incrementing when the energy signal is below or above the electrical reference level.

63. Apparatus for use in reducing scatter in radiation imaging for use with a detector of ionizing radiation, where the ionizing radiation is partly unscattered and partly Compton scattered, the detector producing an energy signal representing values of energy of the ionizing radiation in a first energy range around a photopeak for the radiation and producing coordinate position information for the radiation, and where the apparatus is for use with data storage means for accumulating numerical values representing a number of occurrences of an unblank signal corresponding to each coordinate position, and means for displaying an image based on the numerical values from the data storage means, the apparatus comprising:

memory means for storing values at respective addresses corresponding to coordinate positions of the ionizing radiation;

means for replacing a value already stored at a particular address in the memory means with a latest value which is the sum of the already-stored value plus a first predetermined value having a first sign, when the energy signal represents a value of energy in a second energy range having at least some energies in common with the first range and less than half as wide as the first range and the ionizing radiation occurs at a coordinate position corresponding to that particular address;

means for comparing the latest value at the particular address with a preset value when ionizing radiation subsequently occurs at the coordinate position corresponding to said address and the energy signal represents a value of energy in a part of the first range outside the second range; and means for supplying the unblank signal and coordinate position information for the ionizing radiation to the data storage means when the comparing means indicates that the latest value at said address is not less than the preset value when the first sign is negative or when the comparing means indicates that the value at said address is not greater than the preset value when the first sign is positive, and otherwise replacing the latest value at said address with another value equal to the sum of the latest value and a second predetermined value having a second sign opposite to that of the first predetermined value.

64. Apparatus for scatter reduction in radiation imaging for use with a detector of ionizing radiation that is partly unscattered and partly Compton scattered, the detector producing an energy signal representing values of energy of the radiation in a first energy range around a photopeak for the radiation and producing coordinate position information for the radiation, the apparatus comprising:

memory means for holding a spectrum of intensity values representing a scatter spectrum;

means for supplying an electrical reference level representing a predetermined energy in the first energy range of the radiation by premeasuring the scatter spectrum in the first energy range and predetermining the energy at which the total scatter in the first energy range below said energy is substantially equal to a predetermined fraction of the scatter in the first energy range; and means for producing a signal indicating when the energy signal is below or above the electrical reference level.

65. Apparatus as set forth in claim 64 wherein said means for supplying the electrical reference level includes a digital computer and said means for producing the signal includes means for comparing the energy signal with the electrical reference level.

66. Apparatus for use in reducing scatter in radiation imaging of ionizing radiation where the ionizing radiation has a photopeak in a first energy range and where the apparatus is for use with data storage means for holding numerical values and with means for displaying an image based on the numerical values in the data storage means, the apparatus comprising:

means for detecting ionizing radiation that is partly unscattered and partly Compton scattered to produce an energy signal representing values of energy of the ionizing radiation in the first energy range and to produce coordinate position information for the ionizing radiation; and means responsive to the energy signal and the coordinate position information for generating numerical values for each coordinate position and storing them in the data storage means, the numerical values being a function of the difference of the number of occurrences of ionizing radiation in the first energy range at each coordinate position less a second number proportional to the number of occurrences of ionizing radiation at that coordinate position in a second energy range which is less than half as wide as the first energy range and having at least some energies in common with the first energy range.

67. Apparatus for scatter reduction in radiation imaging for use with a detector of ionizing radiation that is partly unscattered and partly Compton scattered, the detector producing an energy signal representing values of energy of the radiation in a first energy range around a photopeak for the radiation and producing coordinate position information for the radiation, the apparatus comprising:

memory means for holding a spectrum of intensity values representing a scatter spectrum; and means for premeasuring the scatter spectrum in the first energy range and producing an electrical signal representing a characteristic number from the scatter spectrum as a function of the ratio of the scatter in the first energy range to the total of the scatter in a predetermined lower energy fraction of the first energy range.

68. Apparatus as set forth in claim 67 wherein said premeasuring and predetermining means includes means for producing a reference signal representing a particular energy value in the first energy range that separates the lower energy fraction from the rest of the first energy range.

69. Apparatus as set forth in claim 68 further comprising means for comparing the reference signal with the energy signal to produce an electrical identification signal indicating whether the energy signal represents an energy value that is greater or less than the particular energy value.

70. Apparatus as set forth in claim 69 further comprising means responsive to the electrical identification signal, to the electrical signal representing the characteristic number and to the coordinate position information for generating numerical values for each coordinate position and storing them for display purposes, the numerical values being a function of the difference of the number of occurrences of radiation in the first energy range at each coordinate position less a second number which is a function of the characteristic number and the number of occurrences of radiation at that coordinate position in the predetermined lower energy fraction of the first energy range.

71. Apparatus as set forth in claim 67 further comprising means for selectively establishing the predetermined fraction corresponding to each of a plurality of radionuclides.

72. Apparatus as set forth in claim 67 further comprising means responsive to the electrical signal representing the characteristic number and to the coordinate position information for generating numerical values for each coordinate position and storing them for display purposes, the numerical values being a function of the difference of the number of occurrences of radiation in the first energy range at each coordinate position less a second number which is a function of the characteristic number and the number of occurrences of radiation at that coordinate position in a second energy range.

73. A method for scatter reduction in radiation imaging for use with a detector of ionizing radiation that is partly unscattered and partly Compton scattered, the detector producing an energy signal representing values of energy of the radiation and producing coordinate position information for the radiation, and for use with data storage means for holding numerical values and means for displaying an image based on the numerical values in the data storage means, the method comprising the steps of:
  producing first and second signals which indicate whether each value of energy represented by the energy signal at a given time is in a first energy range or in a second energy range less than half as wide as the first energy range and having at least some energies in common with the first energy range; and
  generating numerical values for each coordinate position and storing them in the data storage means, the numerical values being a function of the difference of the number of occurrences of radiation in the first energy range at each coordinate position less a second number proportional to the number of occurrences of radiation in the second energy range at that coordinate position.

74. A method for scatter reduction in radiation imaging of ionizing radiation that has a photopeak in a first energy range and for use with data storage means for holding numerical values and means for displaying an image based on the numerical values in the data storage means, the method comprising the steps of:
  detecting ionizing radiation that is partly unscattered and partly Compton scattered to produce an energy signal representing values of energy of the radiation in the first energy range and to produce coordinate position information for the radiation; and
  generating numerical values for each coordinate position and storing them in the data storage means, the numerical values being a function of the difference of the number of occurrences of radiation in the first energy range at each coordinate position less a second number proportional to and at least two times the number of occurrences of radiation at that coordinate position in a second energy range.

75. A method for scatter reduction in radiation imaging for use with a detector of ionizing radiation that is partly unscattered and partly Compton scattered, the detector producing an energy signal representing values of energy of the radiation and producing coordinate position information for the radiation, and for use with data storage means for holding numerical values corresponding to each coordinate position, a circuit for incrementing each corresponding numerical value in response to an unblank signal and the coordinate position information, and means for then displaying an image based on the numerical values in the data storage means, the method comprising the steps of:
  storing tabular values corresponding to each coordinate position;
  incrementing or decrementing the tabular value for a particular coordinate position depending on whether the energy signal produced by an occurrence of the radiation at that coordinate position satisfies a first or a second predetermined energy condition respectively, and if the tabular value at that coordinate position has reached a preset value then instead producing an unblank signal to actuate the incrementing circuit, whereby that circuit increments the numerical value for that coordinate position in producing numerical values over a period of time for display purposes.

76. A method for scatter reduction in radiation imaging for use with a detector of ionizing radiation that is partly unscattered and partly Compton scattered, the detector producing an energy signal representing values of energy of the radiation in a first energy range around a photopeak for the radiation and producing coordinate position information for the radiation, and for use with data storage means for accumulating numerical values representing a number of occurrences of an unblank signal corresponding to each coordinate position, and means for displaying an image based on the numerical values from the data storage means, the method comprising the steps of:
  storing values at respective addresses corresponding to coordinate positions of the radiation;
  replacing a value already stored at a particular address with a latest value which is the sum of the already-stored value plus a first predetermined value having a first sign, when the energy signal represents a value of energy in a second energy range having at least some energies in common with the first range and less than half as wide as the first range and the radiation occurs at a coordinate position corresponding to that particular address;
  comparing the latest value at the particular address with a preset value when radiation subsequently occurs at the coordinate position corresponding to said address and the energy signal represents a value of energy in a part of the first range outside the second range; and
  supplying the unblank signal and coordinate position information for the radiation to the data storage means when the comparing means indicates that the latest value at said address is not less than the preset value when the first sign is negative or when the comparing means indicates that the value at said address is not greater than the preset value when the first sign is positive, and otherwise replacing the latest value at said address with another value equal to the sum of the latest value and a second predetermined value having a second sign opposite to that of the first predetermined value.

77. A method for scatter reduction in radiation imaging for use with a detector of ionizing radiation that is partly unscattered and partly Compton scattered, the detector producing an energy signal representing values of energy of the radiation in a first energy range around a photopeak for the radiation and producing coordinate position information for the radiation, the method comprising the steps of:
  electronically storing a spectrum of intensity values representing a scatter spectrum;
  electronically determining the energy at which the total scatter in the scatter spectrum in the first energy range below said energy is substantially equal to a predetermined fraction of the scatter in the first energy range;
  supplying an electrical reference level representing the energy so determined; and producing a signal indicating when the energy signal is below or above the electrical reference level for different occurrences of the radiation.

78. A method for scatter reduction in radiation imaging for use with memory means for storing numerical values at respective addresses, and means for displaying an image based on the numerical values in the memory means, the method comprising the steps of:

detecting ionizing radiation wherein some of the radiation is unscattered and some Compton scattered by producing an energy signal representing values of energy of the radiation and producing coordinate position information for the radiation when the energy signal represents a value of energy in a first energy range;

accumulating in the memory means a first number of occurrences of the radiation at each particular coordinate position when the energy signal represents a value of energy in a second energy range less than half as wide as the first energy range and having at least some energies in common with the first energy range and a second number of occurrences of the radiation at each particular coordinate position when the energy signal represents a value of energy in the first energy range and not in the second energy range; storing at respective addresses in the memory means corresponding to each particular coordinate position numerical values which are a function of the first and second numbers so accumulated for each particular coordinate position; and supplying the numerical values to the displaying means for each particular coordinate position.

79. A method for scatter reduction in radiation imaging for use with memory means for storing numerical values at respective addresses, and means for displaying an image based on the numerical values in the memory means, the method comprising the steps of:

detecting ionizing radiation wherein some of the radiation is unscattered and some Compton scattered by producing an energy signal representing values of energy of the radiation and producing coordinate position information for the radiation when the energy signal represents a value of energy in a first energy range;

accumulating in the memory means a first number of occurrences of the radiation at each particular coordinate position when the energy signal represents a value of energy in a second energy range less than half as wide as the first energy range and having at least some energies in common with the first energy range and a second number of occurrences of the radiation at each particular coordinate position when the energy signal represents a value of energy anywhere in the first energy range;

storing at respective addresses in the memory means corresponding to each particular coordinate position numerical values which are a function of the first and second numbers so accumulated for each particular coordinate position; and supplying the numerical values to the displaying means for each particular coordinate position.

80. A method for scatter reduction in radiation imaging for use with memory means for storing numerical values at respective addresses, and means for displaying an image based on the numerical values in the memory means, the method comprising the steps of:

detecting ionizing radiation wherein some of the radiation is unscattered and some Compton scattered by producing an energy signal representing values of energy of the radiation and producing coordinate position information for the radiation when the energy signal represents a value of energy in a first energy range;

accumulating in the memory means a first number of occurrences of the radiation at each particular coordinate position when the energy signal represents a value of energy anywhere in the first energy range and a second number of occurrences of the radiation at each particular coordinate position when the energy signal represents a value of energy in a higher energy part of the first energy range;

storing at respective addresses in the memory means corresponding to each particular coordinate position numerical values which are a function of the first and second numbers so accumulated for each particular coordinate position; and supplying the numerical values to the displaying means for each particular coordinate position.

81. A method for scatter reduction in radiation imaging of ionizing radiation that has a photopeak in a first energy range and for use with data storage means for holding numerical values and means for displaying an image based on the numerical values in the data storage means, the method comprising the steps of:

detecting ionizing radiation that is partly unscattered and partly Compton scattered to produce an energy signal representing values of energy of the radiation in the first energy range and to produce coordinate position information for the radiation; and generating numerical values for each coordinate position and storing them in the data storage means, the numerical values being a function of the difference of a number of occurrences of radiation in the first energy range at each coordinate position less a second number proportional to and at least two times a number of occurrences of radiation at that coordinate position in a second energy range.

82. A method for scatter reduction in radiation imaging for use with a detector of ionizing radiation that is partly unscattered and partly Compton scattered, the detector producing an energy signal representing values of energy of the radiation in a first energy range around a photopeak for the radiation and producing coordinate position information for the radiation, the method comprising the steps of premeasuring a scatter spectrum in the first energy range and producing an electrical signal representing a characteristic number from the scatter spectrum as a function of the ratio of the scatter in the first energy range to the total of the scatter in a predetermined lower energy fraction of the first energy range.

* * * * *